(12) United States Patent
Moaddeb et al.

(10) Patent No.: US 7,722,668 B2
(45) Date of Patent: May 25, 2010

(54) CARDIAC VALVE IMPLANT WITH ENERGY ABSORBING MATERIAL

(75) Inventors: Shahram Moaddeb, Irvine, CA (US); Emanuel Shaoulian, Newport Beach, CA (US); Samuel M. Shaolian, Newport Beach, CA (US)

(73) Assignee: Micardia Corporation, Irvine, CA (US)

( * ) Notice: Subject to any disclaimer, the term of this patent is extended or adjusted under 35 U.S.C. 154(b) by 0 days.

(21) Appl. No.: 12/032,476

(22) Filed: Feb. 15, 2008

(65) Prior Publication Data

US 2008/0215145 A1 Sep. 4, 2008

Related U.S. Application Data

(63) Continuation of application No. 11/124,409, filed on May 6, 2005, now Pat. No. 7,396,364.

(60) Provisional application No. 60/584,432, filed on Jun. 29, 2004.

(51) Int. Cl.
A61F 2/06 (2006.01)
(52) U.S. Cl. .................................... 623/2.36
(58) Field of Classification Search ........ 623/2.36–2.42
See application file for complete search history.

(56) References Cited

U.S. PATENT DOCUMENTS

| | | | |
|---|---|---|---|
| 3,868,956 A | 3/1975 | Alfidi et al. | |
| 4,233,690 A | 11/1980 | Akins | |
| 4,489,446 A | 12/1984 | Reed | |
| 4,507,115 A | 3/1985 | Kambara et al. | |
| 4,556,050 A | 12/1985 | Hodgson et al. | |

(Continued)

FOREIGN PATENT DOCUMENTS

| | | |
|---|---|---|
| CA | 2132730 | 6/1994 |
| WO | WO 94/12101 | 6/1994 |
| WO | WO 96/34211 | 10/1996 |
| WO | WO 2004/103223 A1 | 12/2004 |
| WO | WO 2005/062931 A2 | 7/2005 |

OTHER PUBLICATIONS

PCT International Search Report and Written Opinion mailed Dec. 20, 2005, Application No. PCT/US05/25044.

(Continued)

*Primary Examiner*—Suzette J Gherbi
(74) *Attorney, Agent, or Firm*—Knobbe, Martens, Olson & Bear, LLP

(57) ABSTRACT

Methods and devices are provided for support of a body structure. The devices can be adjusted within the body of a patient in a minimally invasive or non-invasive manner such as by applying energy percutaneously or external to the patient's body. The energy may include, for example, acoustic energy, radio frequency energy, light energy and magnetic energy. Thus, as the body structure changes size and/or shape, the size and/or shape of the annuloplasty rings can be adjusted to provide continued reinforcement. In certain embodiments, the devices include a body member including a shape memory material, and an energy absorption enhancement material configured to absorb energy in response to an activation energy. The energy absorption enhancement material is in thermal communication with said shape memory material. The body member has a first size of a dimension in a first configuration and a second size of the dimension in a second configuration, and is configured to be implanted in the first configuration into a heart. The body member is configured to transform from the first configuration to the second configuration in response to the activation energy. The second configuration is configured to reduce a dimension of a cardiac valve annulus in the heart.

5 Claims, 29 Drawing Sheets

U.S. PATENT DOCUMENTS

| | | | |
|---|---|---|---|
| 4,574,782 A | 3/1986 | Borrelli et al. | |
| 4,602,911 A | 7/1986 | Ahmadi et al. | |
| 4,633,875 A | 1/1987 | Turner | |
| 4,665,906 A | 5/1987 | Jervis | |
| 4,805,618 A | 2/1989 | Ueda et al. | |
| 4,917,698 A | 4/1990 | Carpentier et al. | |
| 5,010,897 A | 4/1991 | Leveen | |
| 5,061,277 A | 10/1991 | Carpentier et al. | |
| 5,064,431 A | 11/1991 | Gilbertson et al. | |
| 5,099,576 A | 3/1992 | Shinmura | |
| 5,104,407 A | 4/1992 | Lam et al. | |
| 5,171,252 A | 12/1992 | Friedland | |
| 5,201,880 A * | 4/1993 | Wright et al. | 623/2.37 |
| 5,290,300 A | 3/1994 | Cosgrove et al. | |
| 5,350,413 A | 9/1994 | Miller | |
| 5,415,623 A | 5/1995 | Cherubini | |
| 5,509,888 A | 4/1996 | Miller | |
| 5,843,178 A | 12/1998 | Vanney et al. | |
| 5,850,837 A | 12/1998 | Shiroyama et al. | |
| 5,882,302 A | 3/1999 | Driscoll, Jr. et al. | |
| 5,888,240 A * | 3/1999 | Carpentier et al. | 623/2.36 |
| 5,979,456 A | 11/1999 | Magovern | |
| 6,039,759 A | 3/2000 | Carpentier | |
| 6,045,497 A | 4/2000 | Schweich, Jr. et al. | |
| 6,093,883 A | 7/2000 | Sanghvi et al. | |
| 6,160,084 A | 12/2000 | Langer et al. | |
| 6,167,313 A | 12/2000 | Gray et al. | |
| 6,273,908 B1 | 8/2001 | Ndondo-Lay | |
| 6,361,559 B1 | 3/2002 | Houser et al. | |
| 6,388,043 B1 | 5/2002 | Langer et al. | |
| 6,391,054 B2 * | 5/2002 | Carpentier et al. | 623/2.37 |
| 6,406,493 B1 | 6/2002 | Tu et al. | |
| 6,425,867 B1 | 7/2002 | Vaezy et al. | |
| 6,454,698 B1 | 9/2002 | Forsell | |
| 6,503,274 B1 * | 1/2003 | Howanec et al. | 623/2.37 |
| 6,565,603 B2 | 5/2003 | Cox | |
| 6,569,198 B1 | 5/2003 | Wilson et al. | |
| 6,599,234 B1 | 7/2003 | Gray et al. | |
| 6,676,702 B2 | 1/2004 | Mathis | |
| 6,718,985 B2 | 4/2004 | Hlavka et al. | |
| 6,720,402 B2 | 4/2004 | Langer et al. | |
| 6,726,716 B2 * | 4/2004 | Marquez | 623/2.36 |
| 6,730,118 B2 | 5/2004 | Spenser et al. | |
| 6,740,094 B2 | 5/2004 | Maitland et al. | |
| 6,764,510 B2 | 7/2004 | Vidlund et al. | |
| 6,786,904 B2 | 9/2004 | Doscher et al. | |
| 6,805,710 B2 | 10/2004 | Quijano et al. | |
| 7,101,395 B2 | 9/2006 | Tremulis et al. | |
| 7,144,363 B2 | 12/2006 | Pai et al. | |
| 7,361,190 B2 * | 4/2008 | Shaoulian et al. | 623/2.36 |
| 7,396,364 B2 | 7/2008 | Moaddeb et al. | |
| 7,510,577 B2 * | 3/2009 | Moaddeb et al. | 623/2.37 |
| 2002/0095167 A1 | 7/2002 | Liddicoat et al. | |
| 2002/0133223 A1 | 9/2002 | Vito et al. | |
| 2002/0133225 A1 | 9/2002 | Gordon | |
| 2002/0151961 A1 | 10/2002 | Lashinski et al. | |
| 2002/0183837 A1 | 12/2002 | Streeter et al. | |
| 2002/0183838 A1 | 12/2002 | Liddicoat et al. | |
| 2003/0055198 A1 | 3/2003 | Langer et al. | |
| 2003/0069570 A1 | 4/2003 | Witzel et al. | |
| 2003/0130731 A1 | 7/2003 | Vidlund et al. | |
| 2003/0135267 A1 | 7/2003 | Solem et al. | |
| 2003/0139787 A1 | 7/2003 | Eggers et al. | |
| 2003/0144732 A1 | 7/2003 | Cosgrove et al. | |
| 2003/0191528 A1 | 10/2003 | Quijano et al. | |
| 2003/0199974 A1 | 10/2003 | Lee et al. | |
| 2003/0233142 A1 | 12/2003 | Morales et al. | |
| 2004/0087899 A1 | 5/2004 | Weber et al. | |
| 2004/0093017 A1 | 5/2004 | Chanduszki | |
| 2004/0098116 A1 | 5/2004 | Callas et al. | |
| 2004/0102841 A1 | 5/2004 | Langberg et al. | |
| 2004/0106949 A1 | 6/2004 | Cohn et al. | |
| 2004/0138744 A1 | 7/2004 | Lashinski et al. | |
| 2004/0139975 A1 | 7/2004 | Nelson et al. | |
| 2004/0153147 A1 | 8/2004 | Mathis | |
| 2004/0181242 A1 | 9/2004 | Stack et al. | |
| 2004/0210304 A1 | 10/2004 | Seguin et al. | |
| 2004/0243227 A1 | 12/2004 | Starksen | |
| 2004/0243230 A1 | 12/2004 | Navia et al. | |
| 2004/0249453 A1 | 12/2004 | Cartledge et al. | |
| 2004/0250820 A1 | 12/2004 | Forsell | |
| 2004/0260393 A1 | 12/2004 | Rahdert et al. | |
| 2005/0004417 A1 | 1/2005 | Nelson et al. | |
| 2005/0033446 A1 | 2/2005 | Deem et al. | |
| 2005/0038506 A1 | 2/2005 | Webler et al. | |
| 2005/0043792 A1 | 2/2005 | Solem et al. | |
| 2005/0055087 A1 | 3/2005 | Starksen | |
| 2005/0055089 A1 | 3/2005 | Macoviak et al. | |
| 2005/0060030 A1 | 3/2005 | Lashinski et al. | |
| 2005/0065601 A1 | 3/2005 | Lee et al. | |
| 2005/0080483 A1 | 4/2005 | Solem et al. | |
| 2005/0119733 A1 | 6/2005 | Wiliams et al. | |
| 2005/0288776 A1 | 12/2005 | Shaoulian et al. | |
| 2005/0288777 A1 | 12/2005 | Rhee et al. | |
| 2005/0288778 A1 | 12/2005 | Shaoulian et al. | |
| 2005/0288779 A1 | 12/2005 | Shaoulian et al. | |
| 2005/0288780 A1 | 12/2005 | Rhee et al. | |
| 2005/0288781 A1 | 12/2005 | Moaddeb et al. | |
| 2005/0288782 A1 | 12/2005 | Moaddeb et al. | |
| 2005/0288783 A1 | 12/2005 | Shaoulian et al. | |
| 2006/0015002 A1 | 1/2006 | Moaddeb et al. | |
| 2006/0015178 A1 | 1/2006 | Moaddeb et al. | |
| 2006/0025854 A1 | 2/2006 | Lashinski et al. | |
| 2006/0253191 A1 | 11/2006 | Salahieh et al. | |
| 2007/0038296 A1 | 2/2007 | Navia et al. | |
| 2007/0050020 A1 | 3/2007 | Spence | |
| 2007/0055368 A1 | 3/2007 | Rhee et al. | |
| 2007/0239272 A1 * | 10/2007 | Navia et al. | 623/2.36 |
| 2009/0248148 A1 * | 10/2009 | Shaolian et al. | 623/2.37 |

OTHER PUBLICATIONS

PCT International Search Report and Written Opinion mailed Dec. 23, 2005, Application No. PCT/US05/21136.

Alonso-Ley, M.D., "Adjustable Annuloplasty for Tricuspid Insufficiency," *Thoracic Surgery*, vol. 46, No. 3, Sep. 1985.

Boyd et al., "Tricuspid annuloplasty five and one-half years' experience with 78 patents," *The Journal of Thoracic Cardiovascular Surgery* (1974).

Lendlein and Langer, "Sciencexpress: Biodegradable, elastic shape memory polymers for potential biomedical applications," Apr. 25, 2002.

Ryklina et al., Two-way shape memory effect inducing in NiTi Alloy and its Application to a Device for Clipping Blood Vessels.

Lutter, et al.; Percutaneous Aortic Valve Replacement: An Experimental Study; Journal of Thoracic and Cardiovascular Surgery; Apr. 2002; pp. 768-776; vol. 123.

Younes Boudjemline et al.; Steps Toward Percutaneous Aortic Valve Replacement; Circulation, Journal of the American Heart Association; 2002; pp. 775-778; vol. 105.

Cribier et al.; Early Experience with Percutaneous Transcatheter Implantation of Heart Valve Prosthesis for the Treatment of End-Stage Inoperable Patients with Calcific Aortic Stenosis; Journal of the American College of Cardiology; 2004; pp. 698-703; vol. 43.

Vaezy et al.; Image-Guided Acoustic Therapy; Annu. Rev. Blomed. Eng.; 2001; pp. 375-$90; vol. 3.

* cited by examiner

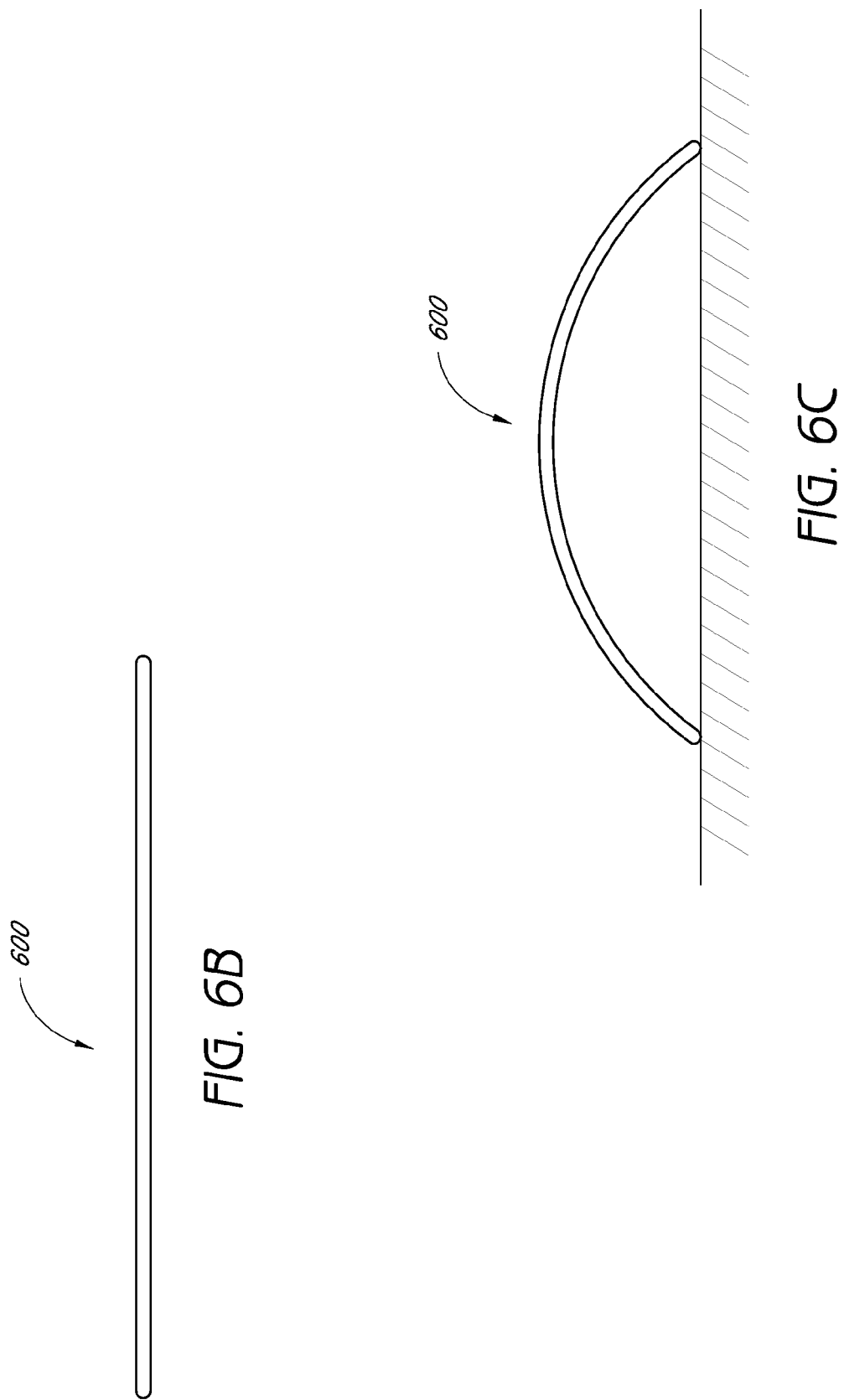

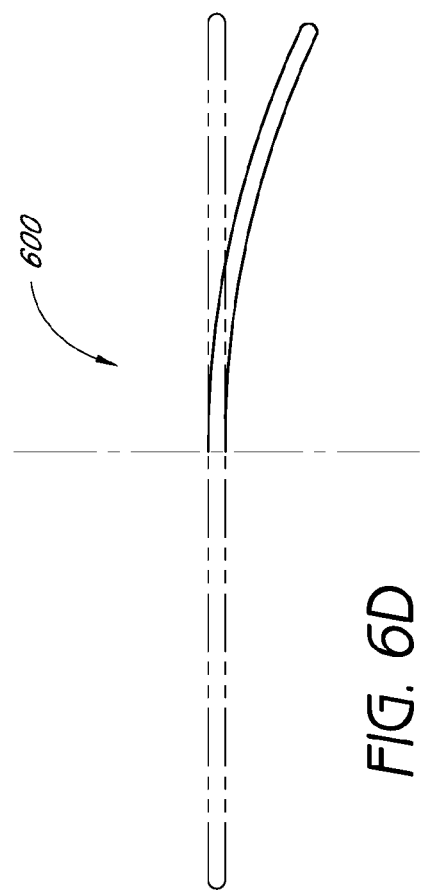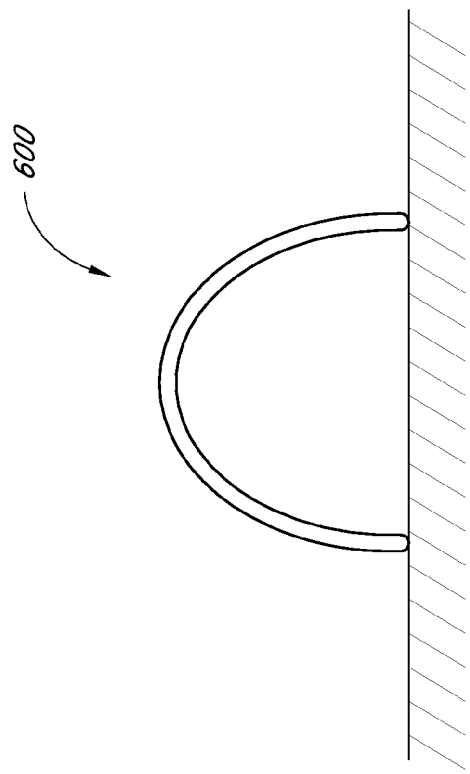

CARDIAC VALVE IMPLANT WITH ENERGY ABSORBING MATERIAL

RELATED APPLICATIONS

This application is a continuation of U.S. application Ser. No. 11/124,409, filed May 6, 2005, entitled "Cardiac Valve Implant with Energy Absorbing Material," which claims priority to U.S. Provisional Application No. 60/584,432, filed Jun. 29, 2004, the contents of both of which are incorporated herein by reference in their entireties.

FIELD OF THE INVENTION

Embodiments of the invention relate to methods and devices for reinforcing dysfunctional heart valves and other body structures. More specifically, embodiments of the present invention relate to annuloplasty rings that can be adjusted within the body of a patient.

BACKGROUND OF THE INVENTION

The circulatory system of mammals includes the heart and the interconnecting vessels throughout the body that include both veins and arteries. The human heart includes four chambers, which are the left and right atrium and the left and right ventricles. The mitral valve, which allows blood flow in one direction, is positioned between the left ventricle and left atrium. The tricuspid valve is positioned between the right ventricle and the right atrium. The aortic valve is positioned between the left ventricle and the aorta, and the pulmonary valve is positioned between the right ventricle and pulmonary artery. The heart valves function in concert to move blood throughout the circulatory system. The right ventricle pumps oxygen-poor blood from the body to the lungs and then into the left atrium. From the left atrium, the blood is pumped into the left ventricle and then out the aortic valve into the aorta. The blood is then recirculated throughout the tissues and organs of the body and returns once again to the right atrium.

If the valves of the heart do not function properly, due either to disease or congenital defects, the circulation of the blood may be compromised. Diseased heart valves may be stenotic, wherein the valve does not open sufficiently to allow adequate forward flow of blood through the valve, and/or incompetent, wherein the valve does not close completely. Incompetent heart valves cause regurgitation or excessive backward flow of blood through the valve when the valve is closed. For example, certain diseases of the heart valves can result in dilation of the heart and one or more heart valves. When a heart valve annulus dilates, the valve leaflet geometry deforms and causes ineffective closure of the valve leaflets. The ineffective closure of the valve can cause regurgitation of the blood, accumulation of blood in the heart, and other problems.

Diseased or damaged heart valves can be treated by valve replacement surgery, in which damaged leaflets are excised and the annulus is sculpted to receive a replacement valve. Another repair technique that has been shown to be effective in treating incompetence is annuloplasty, in which the effective size of the valve annulus is contracted by attaching a prosthetic annuloplasty repair segment or ring to an interior wall of the heart around the valve annulus. The annuloplasty ring reinforces the functional changes that occur during the cardiac cycle to improve coaptation and valve integrity. Thus, annuloplasty rings help reduce reverse flow or regurgitation while permitting good hemodynamics during forward flow.

Generally, annuloplasty rings comprise an inner substrate of a metal such as stainless steel or titanium, or a flexible material such as silicon rubber or Dacron®. The inner substrate is generally covered with a biocompatible fabric or cloth to allow the ring to be sutured to the heart tissue. Annuloplasty rings may be stiff or flexible, may be open or closed, and may have a variety of shapes including circular, D-shaped, or C-shaped. The configuration of the ring is generally based on the shape of the heart valve being repaired or on the particular application. For example, the tricuspid valve is generally circular and the mitral valve is generally D-shaped. Further, C-shaped rings may be used for tricuspid valve repairs, for example, because it allows a surgeon to position the break in the ring adjacent the atrioventricular node, thus avoiding the need for suturing at that location.

Annuloplasty rings support the heart valve annulus and restore the valve geometry and function. Although the implantation of an annuloplasty ring can be effective, the heart of a patient may change geometry over time after implantation. For example, the heart of a child will grow as the child ages. As another example, after implantation of an annuloplasty ring, dilation of the heart caused by accumulation of blood may cease and the heart may begin returning to its normal size. Whether the size of the heart grows or reduces after implantation of an annuloplasty ring, the ring may no longer be the appropriate size for the changed size of the valve annulus.

SUMMARY OF THE INVENTION

Thus, it would be advantageous to develop systems and methods for reinforcing a heart valve annulus or other body structure using an annuloplasty device that can be adjusted within the body of a patient in a minimally invasive or non-invasive manner. In some embodiments, an adjustable annuloplasty device includes a body member configured to conform at least partially to a cardiac valve annulus. The body member includes a shape memory material configured to transform from a first shape to a second shape in response to being heated. The annuloplasty device further includes a thermally insulative material at least partially covering said body member and a thermally conductive material extending into said thermally insulative material. The thermally conductive material is configured to communicate thermal energy to the body member. The thermally conductive material can be configured as an imaging marker and can include a radiopaque material. The annuloplasty device can further comprise a suturable material at least partially covering said thermally insulative material. The thermally conductive material can be disposed at least partially over said suturable material and can provide indicia, for example, of one or more valve commissure locations after said annuloplasty device is implanted on or near a heart valve annulus. The thermally conductive material can include at least one of a metallic wire or a metallic ribbon and the body member can be selected from a variety of shapes including, for example, ring shaped, C-shaped and D-shaped.

In some embodiments, an adjustable annuloplasty device includes a body member configured to conform at least partially to a cardiac valve annulus. The body member includes a shape memory material configured to transform from a first shape to a second shape in response to being heated. The annuloplasty device further includes a thermally conductive member adjacent said body member, said thermally conductive material configured to communicate thermal energy to said body member. The thermally conductive member can be further configured as an imaging marker and may include a radiopaque material. The annuloplasty device may further include a suturable material at least partially covering said body member. The thermally conductive member can be disposed at least partially over said suturable material and the thermally conductive member can provide indicia of one or more valve commissure locations after said adjustable annuloplasty device is implanted on or near a heart valve annulus. The thermally conductive member can include at least one of a metallic wire or a metallic ribbon, and the body member may be selected from a variety of shapes including, for example, ring shaped, C-shaped and D-shaped.

In some embodiments, an adjustable annuloplasty device includes a body member comprising a material that exhibits a ferromagnetic shape memory effect. The body member can have a first size of a dimension of said device in a first configuration and a second size of said dimension of said device in a second configuration. The body member can be configured to be implanted into a heart so as to reinforce a cardiac valve annulus in said first configuration. The body member can be configured to transform from said first configuration to said second configuration in vivo in response to a magnetic field inducing said ferromagnetic shape memory effect. The body member in said second configuration can be configured to reduce a size of said cardiac valve annulus. The shape memory material may include at least one of Fe—C, Fe—Pd, Fe—Mn—Si, Co—Mn, Fe—Co—Ni—Ti, Ni—Mn—Ga, $Ni_2MnGa$, and Co—Ni—Al. The body member can be configured to transform from said first configuration to said second configuration without substantially changing the temperature of said ferromagnetic shape memory material. The device can have a ring shape, a C-shape, a D-shape, or other shape.

In some embodiments, an adjustable annuloplasty device includes a body member including a shape memory material and an energy absorption enhancement material configured to absorb energy in response to a first activation energy. The energy absorption enhancement material is in thermal communication with said shape memory material. The energy absorption enhancement material may be further configured to heat in response to said first activation energy and may be configured to transfer heat to said shape memory material. The body member can be configured to conform to a first size of a body dimension in a first configuration and a second size of said body dimension in a second configuration. The body member is configured to be implanted in said first configuration into a heart. The body member is configured to transform from said first configuration to said second configuration in response to said first activation energy. The second configuration is configured to reduce a dimension of a cardiac valve annulus in said heart.

The shape memory material can comprise at least one of a metal, a metal alloy, a nickel titanium alloy, a shape memory polymer, polylactic acid, and polyglycolic acid. The annuloplasty device may further be configured to include an electrically conductive material that conduct a current in response to said first activation energy and transfers thermal energy to said shape memory material. The annuloplasty device may further include a suturable material configured to facilitate attachment of said body member to said cardiac valve annulus. The body member can have a third size of said body dimension in a third configuration, wherein said third size is larger than said second size, and wherein said body member is configured to transform to said third configuration in response to a second activation energy to increase said dimension of said cardiac valve annulus. The body member can have a third size of said body dimension in a third configuration, wherein said third size is smaller than said second size, and wherein said body member is configured to transform to said third configuration in response to a second activation energy to decrease said dimension of said cardiac valve annulus. The energy absorption enhancement material can include a nanoparticle that may include, for example, at least one of a nanoshell and a nanosphere. The energy absorption enhancement material can be radiopaque.

In some embodiments, an adjustable annuloplasty ring includes a tubular member configured to be attached to or near a cardiac valve annulus. The tubular member includes a receptacle end and an insert end configured to couple with said receptacle end of said tubular member such that said tubular member substantially forms a shape of a ring. The insert end is configured to move with respect to said receptacle end to change a circumference of said ring. The tubular member can further include a shape memory material configured to change, after implantation in a patient's body, from a first shape to a second shape in response to an activation energy, wherein said shape change causes said change in the circumference of said ring. The tubular member can further include an energy absorption enhancement material disposed within said tubular member. The energy absorption enhancement material facilitates transfer of heat to said shape memory material. The energy absorption enhancement material can be further disposed on an outer surface of said tubular member. The tubular member can further include a ratchet member configured to allow said insert end to move predominantly in a first direction with respect to said receptacle end, and to resist movement in a second, opposite direction. The annuloplasty ring can be ring shaped, C-shaped, D-shaped, or another shape.

In some embodiments, an adjustable annuloplasty ring includes a body member configured to be attached to or near a cardiac valve annulus. The body member includes a first end and a second end configured to couple with said first end of said body member such that said body member substantially forms a shape of a ring. The second end is configured to move with respect to said first end to change a circumference of said ring. The body member can further include a shape memory material configured to change, after implantation in a patient's body, from a first shape to a second shape in response to an activation energy, wherein said shape change causes said change in the circumference of said ring. The body member can further include an energy absorption enhancement material that facilitates transfer of heat (i.e., thermal energy) to said shape memory material. The body member can further include a ratchet member configured to allow said second end to move predominantly in a first direction with respect to said first end, and to resist movement in a second, opposite direction. The annuloplasty ring can be ring shaped, C-shaped, D-shaped, or another shape.

In some embodiments, an adjustable annuloplasty ring includes a first shape memory member configured to transform said annuloplasty ring from a first configuration having a first size of a ring dimension to a second configuration having a second size of the ring dimension. The second size is less than said first size. The ring also includes a second shape memory member configured to transform said annuloplasty ring from said second configuration to a third configuration having a third size of the ring dimension. The second size is less than said third size. The first shape memory member can be configured to change shape in response to being brought to a first temperature and the second shape memory member can be configured to change shape in response to being brought to a second temperature. In some embodiments, the first temperature is lower than said second temperature. In some embodiments, the second temperature is lower than said first temperature. At least one of said first shape memory member and said second shape memory member can include at least one of a metal, a metal alloy, a nickel titanium alloy, a shape memory polymer, polylactic acid, and polyglycolic acid. At least one of said first shape memory member and said second shape memory member can be configured to change shape in response to a magnetic field. At least one of said first shape memory member and said second shape memory member can include at least one of Fe—C, Fe—Pd, Fe—Mn—Si, Co—Mn, Fe—Co—Ni—Ti, Ni—Mn—Ga, Ni$_2$MnGa, and Co—Ni—Al. The ring dimension can be a septilateral dimension.

In some embodiments, an adjustable annuloplasty ring includes a first shape memory member configured to transform said annuloplasty ring from a first configuration having a first size of a ring dimension to a second configuration having a second size of the ring dimension, wherein said second size is less than said first size, and a second shape memory member configured to transform said annuloplasty ring from said second size to a third size of the ring dimension, wherein said third size is less than said second size.

In some embodiments, an adjustable annuloplasty ring includes a first shape memory member configured to transform said annuloplasty ring from a first configuration having a first size of a ring dimension to a second configuration having a second size of the ring dimension, wherein said first size is less than said second size, and a second shape memory member configured to transform said annuloplasty ring from said second configuration to a third configuration having a third size of the ring dimension, wherein said third size is less than said second size.

In some embodiments, an adjustable annuloplasty ring includes a first shape memory member configured to transform said annuloplasty ring from a first configuration having a first size of a ring dimension to a second configuration having a second size of the ring dimension, wherein said first size is less than said second size, and a second shape memory member configured to transform said annuloplasty ring from said second configuration to a third configuration having a third size of the ring dimension, wherein said second size is less than said third size.

In some embodiments, an annuloplasty device configured to support a heart valve includes an anterior portion, a posterior portion, and two lateral portions corresponding to intersections of said anterior portion and said posterior portion. The annuloplasty device has a first shape in a first configuration and a second shape in a second configuration. The annuloplasty device is configured to transform from said first configuration to said second configuration in response to a first activation energy applied thereto. The transformation can be configured to decrease a distance between said anterior portion and said posterior portion without substantially decreasing a distance between said two lateral portions. The annuloplasty device can optionally include one or more imaging markers that can include, for example, radiopaque markers. The transformation can be further configured to increase said distance between said two lateral portions.

In some embodiments, the annuloplasty device further includes a wire that extends at least partially along said anterior and posterior portions, and a first shape memory member at least partially covering or contacting said wire. The wire can be selected from the group consisting of a round wire, a flat wire, a mesh wire, a rod-shaped wire, and a band-shaped wire. The first shape memory member can include a tubular structure, wherein at least a portion of said wire passes through said tubular structure. The tubular structure can include a first shape memory body configured to respond to said first activation energy by bending said wire such that said annuloplasty device transforms from said first shape to said second shape.

The tubular structure can further include a second shape memory body configured to respond to a second activation energy by bending said wire such that said annuloplasty device transforms from said second shape to a third shape. The annuloplasty device in said third shape can have a reduced distance between said anterior portion and said posterior portion as compared to said second shape. Alternatively, the annuloplasty device in said third shape can have an increased distance between said anterior portion and said posterior portion as compared to said second shape. At least one of said first activation energy and said second activation energy can include a magnetic field, acoustic energy, radio frequency energy, light energy, electrical energy and thermal energy. In certain embodiments, the first shape memory body can be brought to a first activation temperature in response to said first activation energy, wherein said second shape memory body can be brought to a second activation temperature in response to said second activation energy. The first activation temperature can be lower than said second activation temperature.

In some embodiments, the annuloplasty device further includes a first shape memory band that extends at least partially along said anterior and posterior portions. The first shape memory band can loop back on itself in a curvilinear configuration such that portions of said first shape memory band overlap one another. The first shape memory band can be configured to change its length in response to said first activation energy such that said overlapping portions slide with respect to one another to change said annuloplasty device from said first configuration to said second configuration. The annuloplasty device can further comprise a second shape memory band at least partially disposed between or adjacent to said overlapping portions of said first shape memory band. The second shape memory band can be configured to respond to a second activation energy to transform said annuloplasty device from said second configuration to a third configuration. The annuloplasty device in said third configuration can have a reduced distance between said anterior portion and said posterior portion as compared to said second shape. Alternatively, the annuloplasty device in said third configuration can have an increased distance between said anterior portion and said posterior portion as compared to said second shape. At least one of said first activation energy and said second activation energy can include a magnetic field, acoustic energy, radio frequency energy, or another form of energy. The first shape memory band can change to a first activation temperature in response to said first activation energy, wherein said second shape memory band changes to a second activation temperature in response to said second activation energy.

In another embodiment, an annuloplasty device changes a patient's cardiac valve annulus size in an anteroposterior dimension without substantially changing said annulus in a lateral dimension. The changing occurs in response to a transmission of energy from a non-invasive source external to the patient's heart to said annuloplasty device.

BRIEF DESCRIPTION OF THE DRAWINGS

FIGS. 6B-6E are schematic diagrams of side views of the shape memory wire of FIG. 6A.

DETAILED DESCRIPTION OF THE INVENTION

Figure 1A:
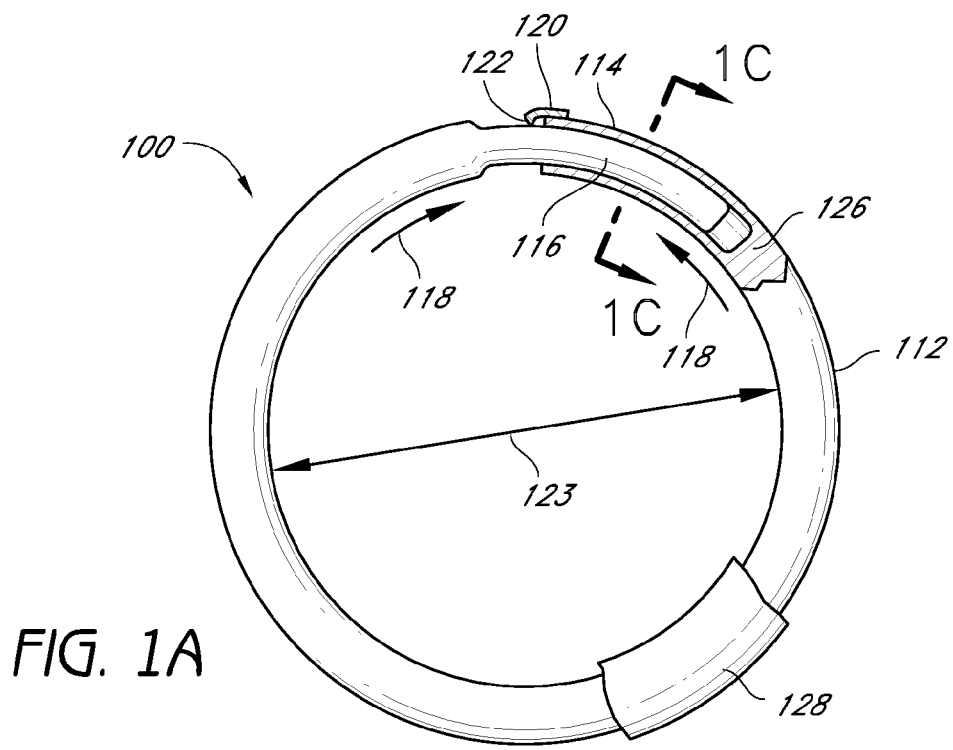
FIG. 1A is a top view in partial section of an embodiment of an adjustable annuloplasty ring.

The present disclosure described systems and methods for reinforcing dysfunctional heart valves and other body structures with adjustable rings. In certain embodiments, an adjustable annuloplasty ring is implanted into the body of a patient such as a human or other animal. The adjustable annuloplasty ring is implanted through an incision or body opening either thoracically (e.g., open-heart surgery) or percutaneously (e.g., via a femoral artery or vein, or other arteries or veins) as is known to someone skilled in the art. The adjustable annuloplasty ring is attached to the annulus of a heart valve to improve leaflet coaptation and to reduce regurgitation. The annuloplasty ring may be selected from one or more shapes comprising a round or circular shape, an oval shape, a C-shape, a D-shape, a U-shape, an open circle shape, an open oval shape, and other curvilinear shapes.

The size of the annuloplasty ring can be adjusted postoperatively to compensate for changes in the size of the heart. As used herein, "postoperatively" refers to a time after implanting the adjustable annuloplasty ring and closing the body opening through which the adjustable annuloplasty ring was introduced into the patient's body. For example, the annuloplasty ring may be implanted in a child whose heart grows as the child gets older. Thus, the size of the annuloplasty ring may need to be increased. As another example, the size of an enlarged heart may start to return to its normal size after an annuloplasty ring is implanted. Thus, the size of the annuloplasty ring may need to be decreased postoperatively to continue to reinforce the heart valve annulus.

In some embodiments, the annuloplasty ring comprises a shape memory material that is responsive to changes in temperature and/or exposure to a magnetic field. Shape memory is the ability of a material to regain its shape after deformation. Shape memory materials include polymers, metals, metal alloys and ferromagnetic alloys. The annuloplasty ring is adjusted in vivo by applying an energy source to activate the shape memory material and cause it to change to a memorized shape. The energy source may include, for example, radio frequency (RF) energy, x-ray energy, microwave energy, ultrasonic energy such as focused ultrasound, high intensity focused ultrasound (HIFU) energy, light energy, electrical energy, magnetic field energy, thermal energy and combinations of the foregoing, and the like. For example, one embodiment of electromagnetic radiation that is useful is infrared energy having a wavelength in a range between approximately 750 nanometers and approximately 1600 nanometers. This type of infrared radiation may be produced efficiently by a solid state diode laser. In certain embodiments, the annuloplasty ring implant is selectively heated using short pulses of energy having an on and off period between each cycle. The energy pulses provide segmental heating which allows segmental adjustment of portions of the annuloplasty ring without adjusting the entire implant.

In some embodiments, the annuloplasty ring includes an energy absorbing material to increase heating efficiency and localize heating in the area of the shape memory material. Thus, damage to the surrounding tissue is reduced or minimized. Energy absorbing materials for light or laser activation energy may include nanoshells, nanospheres and the like, particularly where infrared laser energy is used to energize the material. Such nanoparticles can be made from a dielectric, such as silica, coated with an ultra thin layer of a conductor, such as gold, and be selectively tuned to absorb a particular frequency of electromagnetic radiation. In some embodiments, the nanoparticles range in size between about 5 nm and about 20 nm and can be suspended in a suitable material or solution, such as saline solution. Coatings comprising nanotubes or nanoparticles can also be used to absorb energy from, for example, HIFU, MRI, inductive heating, or the like.

In some embodiments, thin film deposition or other coating techniques such as sputtering, reactive sputtering, metal ion implantation, physical vapor deposition, and chemical deposition can be used to cover portions or all of the annuloplasty ring. Such coatings can be either solid or microporous. When HIFU energy is used, for example, a microporous structure traps and directs the HIFU energy toward the shape memory material. The coating improves thermal conduction and heat removal. In certain embodiments, the coating also enhances radio-opacity of the annuloplasty ring implant. Coating materials can be selected from various groups of biocompatible organic or non-organic, metallic or non-metallic materials such as titanium nitride (TiN), iridium oxide (Irox), carbon, platinum black, titanium carbide (TiC) and other materials used for pacemaker electrodes or implantable pacemaker leads. Other materials discussed herein or known in the art can also be used to absorb energy.

In addition, or in other embodiments, fine conductive wires such as platinum coated copper, titanium, tantalum, stainless steel, gold, or the like, are wrapped around the shape memory material to allow focused and rapid heating of the shape memory material while reducing undesired heating of surrounding tissues.

In some embodiments, the energy source is applied surgically either during implantation or at a later time. For example, the shape memory material can be heated during implantation of the annuloplasty ring by touching the annuloplasty ring with warm object. As another example, the energy source can be surgically applied after the annuloplasty ring has been implanted by percutaneously inserting a catheter into the patient's body and applying the energy through the catheter. For example, RF energy, light energy or thermal energy (e.g., from a heating element using resistance heating) can be transferred to the shape memory material through a catheter positioned on or near the shape memory material. Alternatively, thermal energy can be provided to the shape memory material by injecting a heated fluid through a catheter or circulating the heated fluid in a balloon through the catheter placed in close proximity to the shape memory material. As another example, the shape memory material can be coated with a photodynamic absorbing material which is activated to heat the shape memory material when illuminated by light from a laser diode or directed to the coating through fiber optic elements in a catheter. In some embodiments, the photodynamic absorbing material includes one or more drugs that are released when illuminated by the laser light.

In some embodiments, a removable subcutaneous electrode or coil couples energy from a dedicated activation unit. In some embodiments, the removable subcutaneous electrode provides telemetry and power transmission between the system and the annuloplasty ring. The subcutaneous removable electrode allows more efficient coupling of energy to the implant with minimum or reduced power loss. In certain embodiments, the subcutaneous energy is delivered via inductive coupling.

In some embodiments, the energy source is applied in a non-invasive manner from outside the patient's body. In some embodiments, the external energy source is focused to provide directional heating to the shape memory material so as to reduce or minimize damage to the surrounding tissue. For example, in certain embodiments, a handheld or portable device comprising an electrically conductive coil generates an electromagnetic field that non-invasively penetrates the patient's body and induces a current in the annuloplasty ring. The current heats the annuloplasty ring and causes the shape memory material to transform to a memorized shape. In some embodiments, the annuloplasty ring also comprises an electrically conductive coil wrapped around or embedded in the memory shape material. The externally generated electromagnetic field induces a current in the annuloplasty ring's coil, causing it to heat and transfer thermal energy to the shape memory material.

In some embodiments, an external HIFU transducer focuses ultrasound energy onto the implanted annuloplasty ring to heat the shape memory material. In some embodiments, the external HIFU transducer is a handheld or portable device. The terms "HIFU," "high intensity focused ultrasound" or "focused ultrasound" as used herein are broad terms and are used at least in their ordinary sense and include, without limitation, acoustic energy within a wide range of intensities and/or frequencies. For example, HIFU includes acoustic energy focused in a region, or focal zone, having an intensity and/or frequency that is considerably less than what is currently used for ablation in medical procedures. Thus, in some embodiments, the focused ultrasound is not destructive to the patient's cardiac tissue. In some embodiments, HIFU includes acoustic energy within a frequency range of approximately 0.5 MHz and approximately 30 MHz and a power density within a range of approximately 1 W/cm$^2$ and approximately 500 W/cm$^2$.

In some embodiments, the annuloplasty ring comprises an ultrasound absorbing material or hydro-gel material that allows focused and rapid heating when exposed to the ultrasound energy and transfers thermal energy to the shape memory material. In some embodiments, a HIFU probe is used with an adaptive lens to compensate for heart and respiration movement. The adaptive lens has multiple focal point adjustments. In some embodiments, a HIFU probe with adaptive capabilities comprises a phased array or linear configuration. In certain embodiments, an external HIFU probe comprises a lens configured to be placed between a patient's ribs to improve acoustic window penetration and reduce or minimize issues and challenges regarding passing through bones. In some embodiments, HIFU energy is synchronized with an ultrasound imaging device to allow visualization of the annuloplasty ring implant during HIFU activation. In some embodiments, ultrasound imaging is used to non-invasively monitor the temperature of tissue surrounding the annuloplasty ring by using principles of speed of sound shift and changes to tissue thermal expansion.

In some embodiments, non-invasive energy is applied to the implanted annuloplasty ring using a Magnetic Resonance Imaging (MRI) device. In some embodiments, the shape memory material is activated by a constant magnetic field generated by the MRI device. In addition, or in other embodiments, the MRI device generates RF pulses that induce current in the annuloplasty ring and heat the shape memory material. The annuloplasty ring can include one or more coils and/or MRI energy absorbing material to increase the efficiency and directionality of the heating. Suitable energy absorbing materials for magnetic activation energy include particulates of ferromagnetic material. Suitable energy absorbing materials for RF energy include ferrite materials as well as other materials configured to absorb RF energy at resonant frequencies thereof.

In some embodiments, the MRI device is used to determine the size of the implanted annuloplasty ring before, during and/or after the shape memory material is activated. In some embodiments, the MRI device generates RF pulses at a first frequency to heat the shape memory material and at a second frequency to image the implanted annuloplasty ring. Thus, the size of the annuloplasty ring can be measured without heating the ring. In some embodiments, an MRI energy absorbing material heats sufficiently to activate the shape memory material when exposed to the first frequency and does not substantially heat when exposed to the second frequency. Other imaging techniques known in the art can also be used to determine the size of the implanted ring including, for example, ultrasound imaging, computed tomography (CT) scanning, X-ray imaging, or the like. In certain embodiments, such imaging techniques also provide sufficient energy to activate the shape memory material.

In some embodiments, imaging and resizing of the annuloplasty ring is performed as a separate procedure at some point after the annuloplasty ring as been surgically implanted into the patient's heart and the patient's heart, pericardium and chest have been surgically closed. In some embodiments, it is advantageous to perform the imaging after the heart and/or pericardium have been closed, but before closing the patient's chest, to check for leakage or the amount of regurgitation. If the amount of regurgitation remains excessive after the annuloplasty ring has been implanted, energy from the imaging device (or from another source as discussed herein) can be applied to the shape memory material so as to at least partially contract the annuloplasty ring and reduce regurgitation to an acceptable level. Thus, the success of the surgery can be checked and corrections can be made, if necessary, before closing the patient's chest.

In some embodiments, activation of the shape memory material is synchronized with the heart beat during an imaging procedure. For example, an imaging technique can be used to focus HIFU energy onto an annuloplasty ring in a patient's body during a portion of the cardiac cycle. As the heart beats, the annuloplasty ring can move in and out of this area of focused energy. To reduce damage to the surrounding tissue, the patient's body is exposed to the HIFU energy only during portions of the cardiac cycle that focus the HIFU energy onto the cardiac ring. In certain embodiments, the energy is gated with a signal that represents the cardiac cycle such as an electrocardiogram signal. In some embodiments, the synchronization and gating is configured to allow delivery of energy to the shape memory materials at specific times during the cardiac cycle to avoid or reduce the likelihood of causing arrhythmia or fibrillation during vulnerable periods. For example, the energy can be gated so as to only expose the patient's heart to the energy during the T wave of the electrocardiogram signal.

As discussed above, shape memory materials include, for example, polymers, metals, and metal alloys including ferromagnetic alloys. Exemplary shape memory polymers that are usable for certain embodiments of the present disclosure are disclosed by Langer, et al. in U.S. Pat. No. 6,720,402, issued Apr. 13, 2004, U.S. Pat. No. 6,388,043, issued May 14, 2002, and U.S. Pat. No. 6,160,084, issued Dec. 12, 2000, each of which are hereby incorporated by reference herein. Shape memory polymers respond to changes in temperature by changing to one or more permanent or memorized shapes. In some embodiments, the shape memory polymer is heated to a temperature between approximately 38° C. and approximately 60° C. In certain other embodiments, the shape memory polymer is heated to a temperature in a range between approximately 40° C. and approximately 55° C. In some embodiments, the shape memory polymer has a two-way shape memory effect wherein the shape memory polymer is heated to change it to a first memorized shape and cooled to change it to a second memorized shape. The shape memory polymer can be cooled, for example, by inserting or circulating a cooled fluid through a catheter.

Shape memory polymers implanted in a patient's body can be heated non-invasively using, for example, external light energy sources such as infrared, near-infrared, ultraviolet, microwave and/or visible light sources. In some embodiments, the light energy is selected to increase absorption by the shape memory polymer and reduce absorption by the surrounding tissue. Thus, damage to the tissue surrounding the shape memory polymer is reduced when the shape memory polymer is heated to change its shape. In some embodiments, the shape memory polymer comprises gas bubbles or bubble containing liquids such as fluorocarbons and is heated by inducing a cavitation effect in the gas/liquid when exposed to HIFU energy. In some embodiments, the shape memory polymer may be heated using electromagnetic fields and may be coated with a material that absorbs electromagnetic fields.

Certain metal alloys have shape memory qualities and respond to changes in temperature and/or exposure to magnetic fields. Exemplary shape memory alloys that respond to changes in temperature include titanium-nickel, copper-zinc-aluminum, copper-aluminum-nickel, iron-manganese-silicon, iron-nickel-aluminum, gold-cadmium, combinations of the foregoing, and the like. In some embodiments, the shape memory alloy comprises a biocompatible material such as a titanium-nickel alloy.

Shape memory alloys exist in two distinct solid phases called martensite and austenite. The martensite phase is relatively soft and easily deformed, whereas the austenite phase is relatively stronger and less easily deformed. For example, shape memory alloys enter the austenite phase at a relatively high temperature and the martensite phase at a relatively low temperature. Shape memory alloys begin transforming to the martensite phase at a start temperature ($M_s$) and finish transforming to the martensite phase at a finish temperature ($M_f$). Similarly, such shape memory alloys begin transforming to the austenite phase at a start temperature ($A_s$) and finish transforming to the austenite phase at a finish temperature ($A_f$). Both transformations have a hysteresis. Thus, the $M_s$ temperature and the $A_f$ temperature are not coincident with each other, and the $M_f$ temperature and the $A_s$ temperature are not coincident with each other.

In some embodiments, the shape memory alloy is processed to form a memorized shape in the austenite phase in the form of a ring or partial ring. The shape memory alloy is then cooled below the $M_f$ temperature to enter the martensite phase and deformed into a larger or smaller ring. For example, in some embodiments, the shape memory alloy is formed into a ring or partial ring that is larger than the memorized shape but still small enough to improve leaflet coaptation and reduce regurgitation in a heart valve upon being attached to the heart valve annulus. In some embodiments, the shape memory alloy is sufficiently malleable in the martensite phase to allow a user such as a physician to adjust the circumference of the ring in the martensite phase by hand to achieve a desired fit for a particular heart valve annulus. After the ring is attached to the heart valve annulus, the circumference of the ring can be adjusted non-invasively by heating the shape memory alloy to an activation temperature (e.g., temperatures ranging from the $A_s$ temperature to the $A_f$ temperature).

Thereafter, when the shape memory alloy is exposed to a temperature elevation and transformed to the austenite phase, the alloy changes in shape from the deformed shape to the memorized shape. Activation temperatures at which the shape memory alloy causes the shape of the annuloplasty ring to change shape can be selected and built into the annuloplasty ring such that collateral damage is reduced or eliminated in tissue adjacent the annuloplasty ring during the activation process. Exemplary $A_f$ temperatures for suitable shape memory alloys range between approximately 45° C. and approximately 70° C. Furthermore, exemplary $M_s$ temperatures range between approximately 10° C. and approximately 20° C., and exemplary $M_f$ temperatures range between approximately −1° C. and approximately 15° C. The size of the annuloplasty ring can be changed all at once or incrementally in small steps at different times in order to achieve the adjustment necessary to produce the desired clinical result.

Some shape memory alloys may further include a rhombohedral phase, having a rhombohedral start temperature ($R_s$) and a rhombohedral finish temperature ($R_f$), that exists between the austenite and martensite phases. An example of such a shape memory alloy is a NiTi alloy, which is commercially available from Memry Corporation (Bethel, Conn.). In certain embodiments, an exemplary $R_s$ temperature range is between approximately 30° C. and approximately 50° C., and an exemplary $R_f$ temperature range is between approximately 20° C. and approximately 35° C. One benefit of using a shape memory material having a rhombohedral phase is that in the rhombohedral phase the shape memory material may experience a partial physical distortion, as compared to the generally rigid structure of the austenite phase and the generally deformable structure of the martensite phase.

Some shape memory alloys exhibit a ferromagnetic shape memory effect wherein the shape memory alloy transforms from the martensite phase to the austenite phase when exposed to an external magnetic field. The term "ferromagnetic" as used herein is a broad term and is used in its ordinary sense and includes, without limitation, any material that easily magnetizes, such as a material having atoms that orient their electron spins to conform to an external magnetic field. Ferromagnetic materials include permanent magnets, which can be magnetized through a variety of modes, and materials, such as metals, that are attracted to permanent magnets. Ferromagnetic materials also include electromagnetic materials that are capable of being activated by an electromagnetic transmitter, such as one located outside the heart 100. Furthermore, ferromagnetic materials may include one or more polymer-bonded magnets, wherein magnetic particles are bound within a polymer matrix, such as a biocompatible polymer. The magnetic materials can comprise isotropic and/or anisotropic materials, such as for example NdFeB (neodymium iron boron), SmCo (samarium cobalt), ferrite and/or AlNiCo (aluminum nickel cobalt) particles.

Thus, an annuloplasty ring comprising a ferromagnetic shape memory alloy can be implanted in a first configuration having a first shape and later changed to a second configuration having a second (e.g., memorized) shape without heating the shape memory material above the $A_s$ temperature. Advantageously, nearby healthy tissue is not exposed to high temperatures that could damage the tissue. Further, since the ferromagnetic shape memory alloy does not need to be heated, the size of the annuloplasty ring can be adjusted more quickly and more uniformly than by heat activation.

Exemplary ferromagnetic shape memory alloys include Fe—C, Fe—Pd, Fe—Mn—Si, Co—Mn, Fe—Co—Ni—Ti, Ni—Mn—Ga, $Ni_2MnGa$, Co—Ni—Al, and the like. Some shape memory materials can also change shape in response to changes in temperature. Thus, the shape of such materials can be adjusted by exposure to a magnetic field, by changing the temperature of the material, or both.

In some embodiments, combinations of different shape memory materials are used. For example, in some embodiments, annuloplasty rings can comprise a combination of shape memory polymer and shape memory alloy (e.g., NiTi). In some embodiments, an annuloplasty ring comprises a shape memory polymer tube and a shape memory alloy (e.g., NiTi) disposed within the tube. Such embodiments are flexible and allow the size and shape of the shape memory to be further reduced without impacting fatigue properties. In some embodiments, shape memory polymers are used with shape memory alloys to create a bi-directional (e.g., capable of expanding and contracting) annuloplasty ring. Bi-directional annuloplasty rings can be created with a wide variety of shape memory material combinations having different characteristics.

Figure 1B:
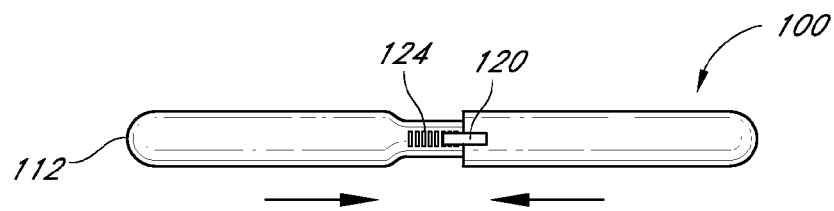
FIG. 1B is a side view of the annuloplasty ring of FIG. 1A.
Figure 1C:
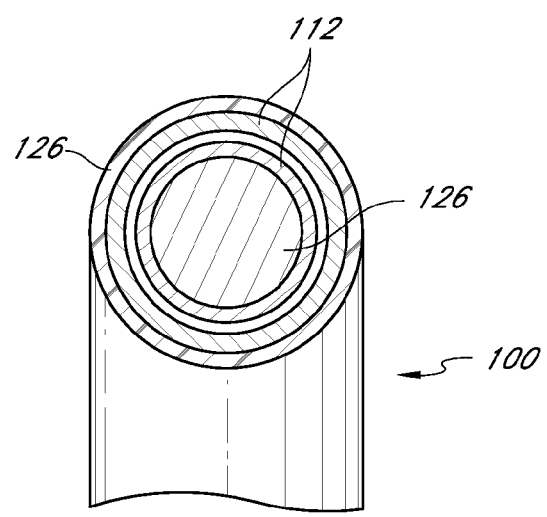
FIG. 1C is a transverse cross-sectional view of the annuloplasty ring of FIG. 1A.

FIGS. 1A-1C illustrate an embodiments of an adjustable annuloplasty ring 100 that can be adjusted in vivo after implantation into a patient's body. The annuloplasty ring 100 has a substantially annular configuration and comprises a tubular body member 112 that folds back upon itself in a substantial circle having a nominal diameter as indicated by arrow 123. The tubular body member 112 comprises a receptacle end 114 and an insert end 116. The insert end 116 of the tubular member 112 is reduced in outer diameter or transverse dimension as compared to the receptacle end 114. As used herein, "dimension" is a broad term having its ordinary and customary meaning and includes a size or distance from a first point to a second point along a line or arc. For example, a dimension may be a circumference, diameter, radius, arc length, or the like. As another example, a dimension may be a distance between an anterior portion and a posterior portion of an annulus.

The receptacle end accepts the insert end 116 of the tubular member 112 to complete the ring-like structure of the annuloplasty ring 100. The insert end 116 slides freely within the receptacle end 114 of the annuloplasty ring 100 which allows contraction of the overall circumference of the ring 100 as the insert end 116 enters the receptacle end 114 as shown by arrows 118 in FIG. 1A. In some embodiments, the nominal diameter or transverse dimension 123 of the annuloplasty ring 100 can be adjusted from approximately 25 mm to approximately 38 mm. However, the skilled artisan will recognize from the disclosure herein that the diameter or transverse dimension 123 of the annuloplasty ring 100 can be adjusted to other sizes depending on the particular application. Indeed, the diameter or transverse dimension 123 of the annuloplasty ring 100 can be configured to reinforce body structures substantially smaller than 25 mm and substantially larger than 38 mm.

It will be appreciated from the disclosure herein that in other embodiments the insert end 116 can couple with the receptacle end 114 without being inserted in the receptacle end 114. For example, the insert end 116 can overlap the receptacle end 114 such that it slides adjacent thereto. In other embodiments, for example, the ends 114, 116 may grooved to guide the movement of the adjacent ends 114, 116 relative to one another. Other embodiments that are within the scope of the disclosure will readily occur to those skilled in the art.

The annuloplasty ring 100 can comprise a suturable material 128, shown partially cut away in FIG. 1A, and not shown in FIGS. 1B and 1C for clarity. The suturable material 128 can be disposed about the tubular member 112 to facilitate surgical implantation of the annuloplasty ring 100 in a body structure, such as about a heart valve annulus. In some embodiments, the suturable material 128 comprises a suitable biocompatible material such as Dacron®, woven velour, polyurethane, polytetrafluoroethylene (PTFE), heparin-coated fabric, or the like. In some embodiments, the suturable material 128 comprises a biological material such as bovine or equine pericardium, homograft, patient graft, or cell-seeded tissue. The suturable material 128 may be disposed about the entire circumference of the tubular member 112, or selected portions thereof. For example, in some embodiments, the suturable material 128 is disposed so as to enclose substantially the entire tubular member 112 except at the narrowed insert end 116 that slides into the receptacle end 118 of the tubular member 112.

As shown in FIGS. 1A and 1B, in some embodiments, the annuloplasty ring 100 also comprises a ratchet member 120 secured to the receptacle end 114 of the tubular member 112. The ratchet member 120 comprises a pawl 122 configured to engage transverse slots 124 (shown in FIG. 1B) on the insert end 116 of the tubular member 112. The pawl 122 of the ratchet member 120 engages the slots 124 in such a way as to allow contraction of the circumference of the annuloplasty ring 100 and prevent or reduce circumferential expansion of the annuloplasty ring 100. Thus, the ratchet reduces unwanted circumferential expansion of the annuloplasty ring 100 after implantation due, for example, to dynamic forces on the annuloplasty ring 100 from the heart tissue during systolic contraction of the heart.

In some embodiments, the tubular member 112 comprises a rigid material such as stainless steel, titanium, or the like, or a flexible material such as silicon rubber, Dacron®, or the like. In some embodiments, after implantation into a patient's body, the circumference of the annuloplasty ring 100 is adjusted in vivo by inserting a catheter (not shown) into the body and pulling a wire (not shown) attached to the tubular member 112 through the catheter to manually slide the insert end 116 of the tubular member 112 into the receptacle end 114 of the tubular member 112. As the insert end 116 slides into the receptacle end 114, the pawl 122 of the ratchet member 120 engages the slots 124 on the insert end 116 to hold the insert end 116 in the receptacle end 114. Thus, for example, as the size of a heart valve annulus reduces after implantation of the annuloplasty ring 100, the size of the annuloplasty ring 100 can also be reduced to provide an appropriate amount of reinforcement to the heart valve.

In some embodiments, the tubular member 112 comprises a shape memory material that is responsive to changes in temperature and/or exposure to a magnetic field. As discussed above, the shape memory material may include shape memory polymers (e.g., polylactic acid (PLA), polyglycolic acid (PGA)) and/or shape memory alloys (e.g., nickel-titanium) including ferromagnetic shape memory alloys (e.g., Fe—C, Fe—Pd, Fe—Mn—Si, Co—Mn, Fe—Co—Ni—Ti, Ni—Mn—Ga, Ni$_2$MnGa, Co—Ni—Al). In some embodiments, the annuloplasty ring 100 is adjusted in vivo by applying an energy source such as radio frequency energy, X-ray energy, microwave energy, ultrasonic energy such as high intensity focused ultrasound (HIFU) energy, light energy, electric field energy, magnetic field energy, combinations of the foregoing, or the like. In some embodiments, the energy source is applied in a non-invasive manner from outside the body. For example, as discussed above, a magnetic field and/or RF pulses can be applied to the annuloplasty ring 100 within a patient's body with an apparatus external to the patient's body such as is commonly used for magnetic resonance imaging (MRI). However, in other embodiments, the energy source may be applied surgically such as by inserting a catheter into the body and applying the energy through the catheter.

In some embodiments, the tubular body member 112 comprises a shape memory material that responds to the application of temperature that differs from a nominal ambient temperature, such as the nominal body temperature of 37° C. for humans. The tubular member 112 is configured to respond by starting to contract upon heating the tubular member 112 above the $A_s$ temperature of the shape memory material. In some embodiments, the annuloplasty ring 100 has an initial diameter or transverse dimension 123 of approximately 30 mm, and contracts or shrinks to a transverse dimension 123 of approximately 23 mm to approximately 28 mm, or any increment between those values. This produces a contraction percentage in a range between approximately 6% and approximately 23%, where the percentage of contraction is defined as a ratio of the difference between the starting diameter and finish diameter divided by the starting diameter.

The activation temperatures (e.g., temperatures ranging from the $A_s$ temperature to the $A_f$ temperature) at which the tubular member 112 contracts to a reduced circumference may be selected and built into the annuloplasty ring 100 such that collateral damage is reduced or eliminated in tissue adjacent the annuloplasty ring 100 during the activation process. Exemplary $A_f$ temperatures for the shape memory material of the tubular member 112 at which substantially maximum contraction occurs are in a range between approximately 38° C. and approximately 75° C. For some embodiments that include shape memory polymers for the tubular member 112, activation temperatures at which the glass transition of the material or substantially maximum contraction occur range between approximately 38° C. and approximately 60° C. In other such embodiments, the activation temperature is in a range between approximately 40° C. and approximately 59° C.

In some embodiments, the tubular member 112 is shape set in the austenite phase to a remembered configuration during the manufacturing of the tubular member 112 such that the remembered configuration is that of a relatively small circumferential value with the insert end 116 fully inserted into the receptacle end 114. After cooling the tubular member 112 below the $M_f$ temperature, the tubular member 112 is manually deformed to a larger circumferential value with the insert end 116 only partially inserted into the receptacle end 114 to achieve a desired starting nominal circumference for the annuloplasty ring 100. In some embodiments, the tubular member 112 is sufficiently malleable in the martensite phase to allow a user such as a physician to adjust the circumferential value by hand to achieve a desired fit with the heart valve annulus. In some embodiments, the starting nominal circumference for the annuloplasty ring 100 is configured to improve leaflet coaptation and reduce regurgitation in a heart valve.

After implantation, the annuloplasty ring 100 can be activated non-invasively by the application of energy to the patient's body to heat the tubular member 112. In certain embodiments, an MRI device is used as discussed above to heat the tubular member 112, which then causes the shape memory material of the tubular member 112 to transform to the austenite phase and remember its contracted configuration. Thus, the circumference of the annuloplasty ring 100 is reduced in vivo without the need for surgical intervention. Standard techniques for focusing the magnetic field from the MRI device onto the annuloplasty ring 100 may be used. For example, a conductive coil can be wrapped around the patient in an area corresponding to the annuloplasty ring 100. In some embodiments, the shape memory material is activated by exposing it other sources of energy, as discussed above.

Figure 2:
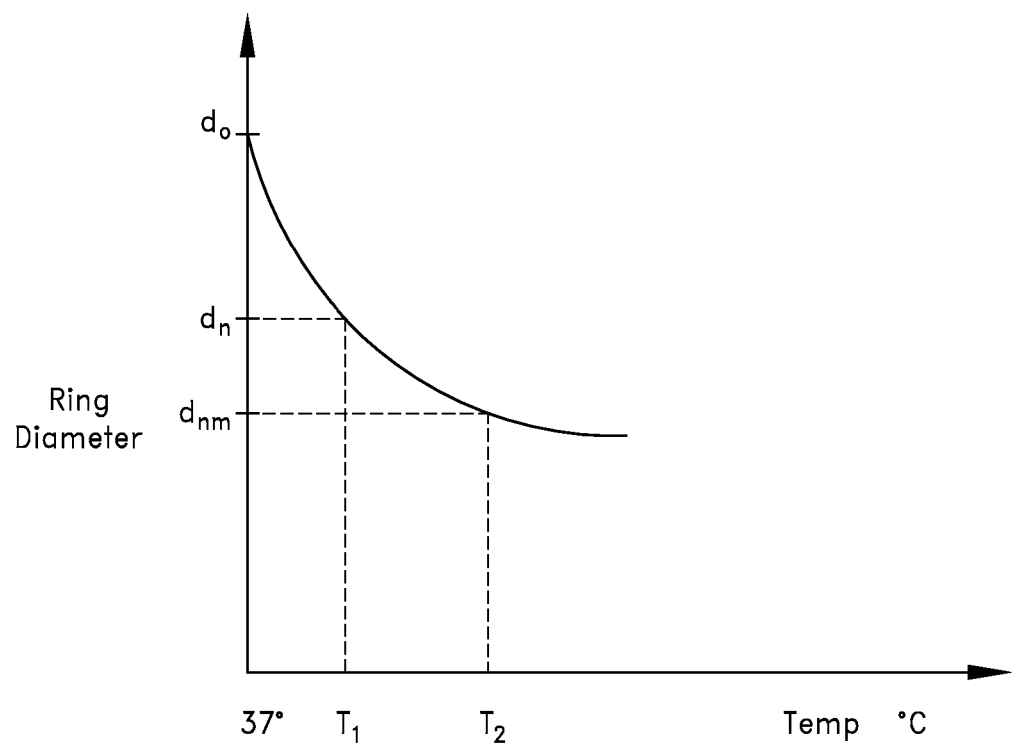
FIG. 2 is a graphical representation of a diameter of an embodiment of an annuloplasty ring in relation to the temperature of the annuloplasty ring.

The circumference reduction process, either non-invasively or through a catheter, can be carried out all at once or incrementally in small steps at different times in order to achieve the adjustment necessary to produce the desired clinical result. If heating energy is applied such that the temperature of the tubular member 112 does not reach the $A_f$ temperature for substantially maximum transition contraction, partial shape memory transformation and contraction may occur. FIG. 2 graphically illustrates the relationship between the temperature of the tubular member 112 and the diameter or transverse dimension 123 of the annuloplasty ring 100 according to certain embodiments. At body temperature of approximately 37° C., the diameter of the tubular member 112 has a first diameter $d_0$. The shape memory material is then increased to a first raised temperature $T_1$. In response, the diameter of the tubular member 112 reduces to a second diameter $d_n$. The diameter of the tubular member 112 can then be reduced to a third diameter $d_{nm}$ by raising the temperature to a second temperature $T_2$.

As graphically illustrated in FIG. 2, in some embodiments, the change in diameter from $d_0$ to $d_{nm}$ is substantially continuous as the temperature is increased from body temperature to $T_2$. For example, in certain embodiments a magnetic field of about 2.5 Tesla to about 3.0 Tesla is used to raise the temperature of the tubular member 112 above the $A_f$ temperature to complete the austenite phase and return the tubular member 112 to the remembered configuration with the insert end 116 fully inserted into the receptacle end 114. However, a lower magnetic field (e.g., 0.5 Tesla) can initially be applied and increased (e.g., in 0.5 Tesla increments) until the desired level of heating and desired contraction of the annuloplasty ring 100 is achieved. In some embodiments, the tubular member 112 comprises a plurality of shape memory materials with different activation temperatures and the diameter of the tubular member 112 is reduced in steps as the temperature increases.

Whether the shape change is continuous or stepped, the diameter or transverse dimension 123 of the ring 100 can be assessed or monitored during the contraction process to determine the amount of contraction by use of MRI imaging, ultrasound imaging, computed tomography (CT), X-ray or the like. If magnetic energy is being used to activate contraction of the ring 100, for example, MRI imaging techniques can be used that produce a field strength that is lower than that required for activation of the annuloplasty ring 100.

In some embodiments, the tubular member 112 comprises an energy absorption enhancement material 126. As shown in FIGS. 1A and 1C, the energy absorption enhancement material 126 may be disposed within an inner chamber of the tubular member 112. As shown in FIG. 1C (and not shown in FIG. 1A for clarity), the energy absorption enhancement material 126 can also be coated on the outside of the tubular member 112 to enhance energy absorption by the tubular member 112. For embodiments that use energy absorption enhancement material 126 for enhanced absorption, it can be desirable for the energy absorption enhancement material 126, a carrier material (not shown) surrounding the energy absorption enhancement material 126, if there is one, or both to be thermally conductive. Thus, thermal energy from the energy absorption enhancement material 126 can be efficiently transferred to the shape memory material of the annuloplasty ring 100, such as the tubular member 112.

As discussed above, the energy absorption enhancement material 126 can include a material or compound that selectively absorbs a desired heating energy and efficiently converts the non-invasive heating energy to heat which is then transferred by thermal conduction to the tubular member 112. The energy absorption enhancement material 126 allows the tubular member 112 to be actuated and adjusted by the non-invasive application of lower levels of energy and also allows for the use of non-conducting materials, such as shape memory polymers, for the tubular member 112. For some embodiments, magnetic flux ranging between about 2.5 Tesla and about 3.0 Tesla may be used for activation. By allowing the use of lower energy levels, the energy absorption enhancement material 126 also reduces thermal damage to nearby tissue. Suitable energy absorption enhancement materials 126 are discussed above.

In some embodiments, a circumferential contraction cycle can be reversed to induce an expansion of the annuloplasty ring 100. Some shape memory alloys, such as NiTi or the like, respond to the application of a temperature below the nominal ambient temperature. After a circumferential contraction cycle has been performed, the tubular member 112 is cooled below the $M_s$ temperature to start expanding the annuloplasty ring 100. The tubular member 112 can also be cooled below the $M_f$ temperature to finish the transformation to the martensite phase and reverse the contraction cycle. As discussed above, certain polymers also exhibit a two-way shape memory effect and can be used to both expand and contract the annuloplasty ring 100 through heating and cooling processes. Cooling can be achieved, for example, by inserting a cool liquid onto or into the annuloplasty ring 100 through a catheter, or by cycling a cool liquid or gas through a catheter placed near the annuloplasty ring 100. Exemplary temperatures for a NiTi embodiment for cooling and reversing a contraction cycle range between approximately 20° C. and approximately 30° C.

In some embodiments, external stresses are applied to the tubular member 112 during cooling to expand the annuloplasty ring 100. In some embodiments, one or more biasing elements (not shown) are operatively coupled to the tubular member 112 so as to exert a circumferentially expanding force thereon. For example, in some embodiments a biasing element such as a spring (not shown) is disposed in the receptacle end 114 of the tubular member 112 so as to push the insert end 16 at least partially out of the receptacle end 114 during cooling. In such embodiments, the tubular member 112 does not include the ratchet member 120 such that the insert end 116 can slide freely into or out of the receptacle end 114.

In some embodiments, the tubular member comprises a ferromagnetic shape memory material, as discussed above. In such embodiments, the diameter of the tubular member 112 can be changed by exposing the tubular member 112 to a magnetic field. Advantageously, nearby healthy tissue is not exposed to high temperatures that could damage the tissue.

Further, since the shape memory material does not need to be heated, the size of the tubular member 112 can be adjusted more quickly and more uniformly than by heat activation.

Figure 3A:
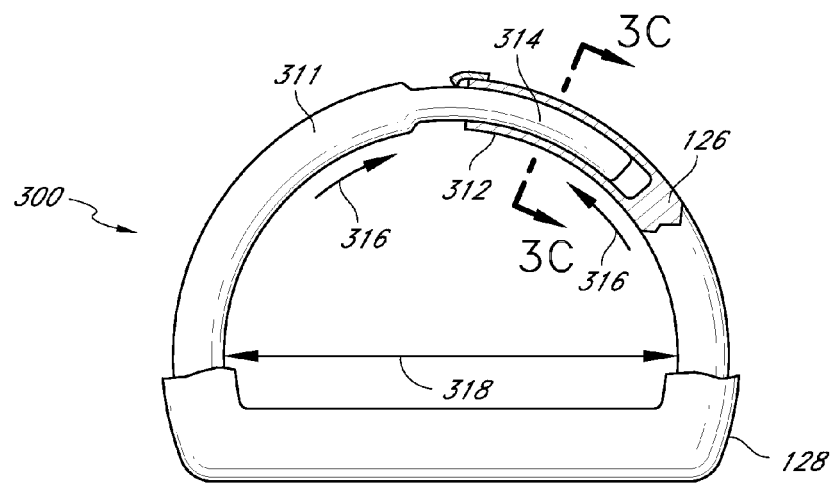
FIG. 3A is a top view in partial section of an embodiment of an adjustable annuloplasty ring having a D-shaped configuration.
Figure 3B:
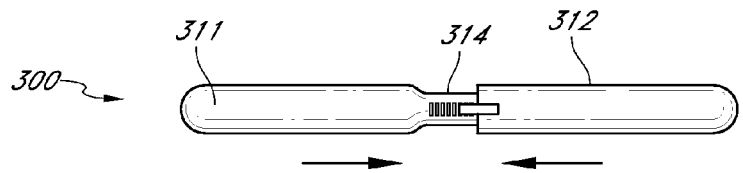
FIG. 3B is a side view of the annuloplasty ring of FIG. 3A.
Figure 3C:
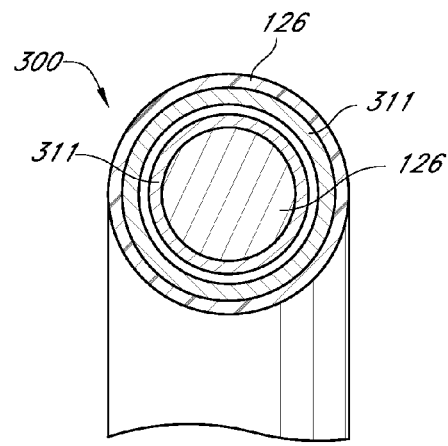
FIG. 3C is a transverse cross-sectional view of the annuloplasty ring of FIG. 3A.

FIGS. 3A-3C illustrate an embodiment of an adjustable annuloplasty ring 300 that is similar to the annuloplasty ring 100 discussed above, but having a D-shaped configuration instead of a circular configuration. The annuloplasty ring 300 comprises a tubular body member 311 having a receptacle end 312 and an insert end 314 sized and configured to slide freely in the hollow receptacle end 312 in an axial direction which allows the annuloplasty ring 300 to constrict upon activation to a lesser circumference or transverse dimension as indicated by arrows 316. The annuloplasty ring 300 has a major transverse dimension indicated by arrow 318 that is reduced upon activation of the annuloplasty ring 300. The major transverse dimension indicated by arrow 318 can be the same as or similar to the transverse dimension indicated by arrow 123 discussed above. In some embodiments, the features, dimensions and materials of the annuloplasty ring 300 are the same as or similar to the features, dimensions and materials of annuloplasty ring 100 discussed above. The D-shaped configuration of ring 32 allows a proper fit of the ring 32 with the morphology of some particular heart valves.

Figure 4A:
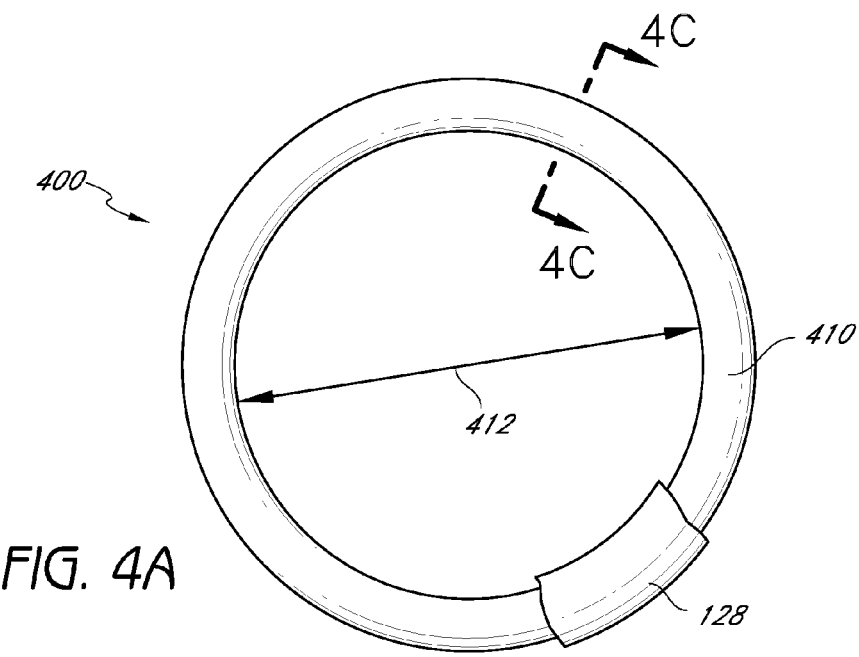
FIG. 4A is a top view of an embodiment of an annuloplasty ring having a substantially circular configuration.
Figure 4B:
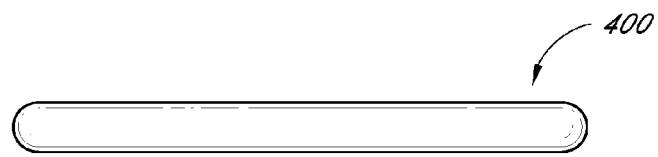
FIG. 4B is a side view of the annuloplasty ring of FIG. 4A.
Figure 4C:
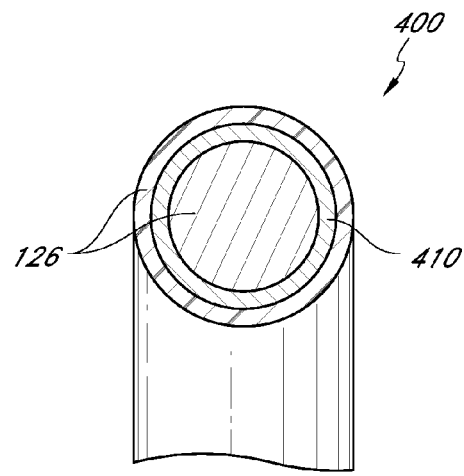
FIG. 4C is a transverse cross-sectional view of the annuloplasty ring of FIG. 4A.

FIGS. 4A-4C show an embodiment of an annuloplasty ring 400 that includes a continuous tubular member 410 surrounded by a suturable material 128. The tubular member 410 has a substantially circular transverse cross section, as shown in FIG. 4C, and has an absorption enhancing material 126 disposed within an inner chamber of the tubular member 410. In certain embodiments, the absorption enhancing material 126 is also disposed on the outer surface of the tubular member 410. The tubular member 410 may be made from a shape memory material such as a shape memory polymer or a shape memory alloy including a ferromagnetic shape memory alloy, as discussed above.

For some embodiments of an annuloplasty ring 400 with a tubular member 410 made from a continuous piece of shape memory alloy (e.g., NiTi alloy) or shape memory polymer, the annuloplasty ring 400 can be activated by the surgical and/or non-invasive application of heating energy by the methods discussed above with regard to other embodiments. For embodiments of the annuloplasty ring 400 with a tubular member 410 made from a continuous piece of ferromagnetic shape memory alloy, the annuloplasty ring 400 can be activated by the non-invasive application of a suitable magnetic field. The annuloplasty ring 400 has a nominal inner diameter or transverse dimension indicated by arrow 412 in FIG. 4A that is set during manufacture of the ring 400. In some embodiments, the annuloplasty ring 400 is sufficiently malleable when it is implanted into a patient's body that it can be adjusted by hand to be fitted to a particular heart valve annulus.

In some embodiments, upon activating the tubular member 410 by the application of energy, the tubular member 410 remembers and assumes a configuration wherein the transverse dimension is less than the nominal transverse dimension 412. A contraction in a range between approximately 6 percent to approximately 23 percent may be desirable in some embodiments which have continuous hoops of shape memory tubular members 410. In certain embodiments, the tubular member 410 comprises a shape memory NiTi alloy having an inner transverse dimension in a range between approximately 25 mm and approximately 38 mm. In some embodiments, the tubular member 410 can contract or shrink in a range between approximately 6 percent and approximately 23 percent, where the percentage of contraction is defined as a ratio of the difference between the starting diameter and finish diameter divided by the starting diameter. In some embodiments, the annuloplasty ring 400 has a nominal inner transverse dimension 412 of approximately 30 mm and an inner transverse dimension in a range between approximately 23 mm and approximately 128 mm in a fully contracted state.

As discussed above in relation to FIG. 2, in certain embodiments, the inner transverse dimension 412 of some embodiments can be altered as a function of the temperature of the tubular member 410. As also discussed above, in some embodiments, the progress of the size change can be measured or monitored in real-time conventional imaging techniques. Energy from conventional imaging devices can also be used to activate the shape memory material and change the inner transverse dimension 412 of the tubular member 410. In certain embodiments, the features, dimensions and materials of the annuloplasty ring 400 are the same as or similar to the features, dimensions and materials of the annuloplasty ring 100 discussed above. For example, in some embodiments, the tubular member 410 comprises a shape memory material that exhibits a two-way shape memory effect when heated and cooled. Thus, the annuloplasty ring 400, in some embodiments, can be contracted and expanded.

Figure 5:
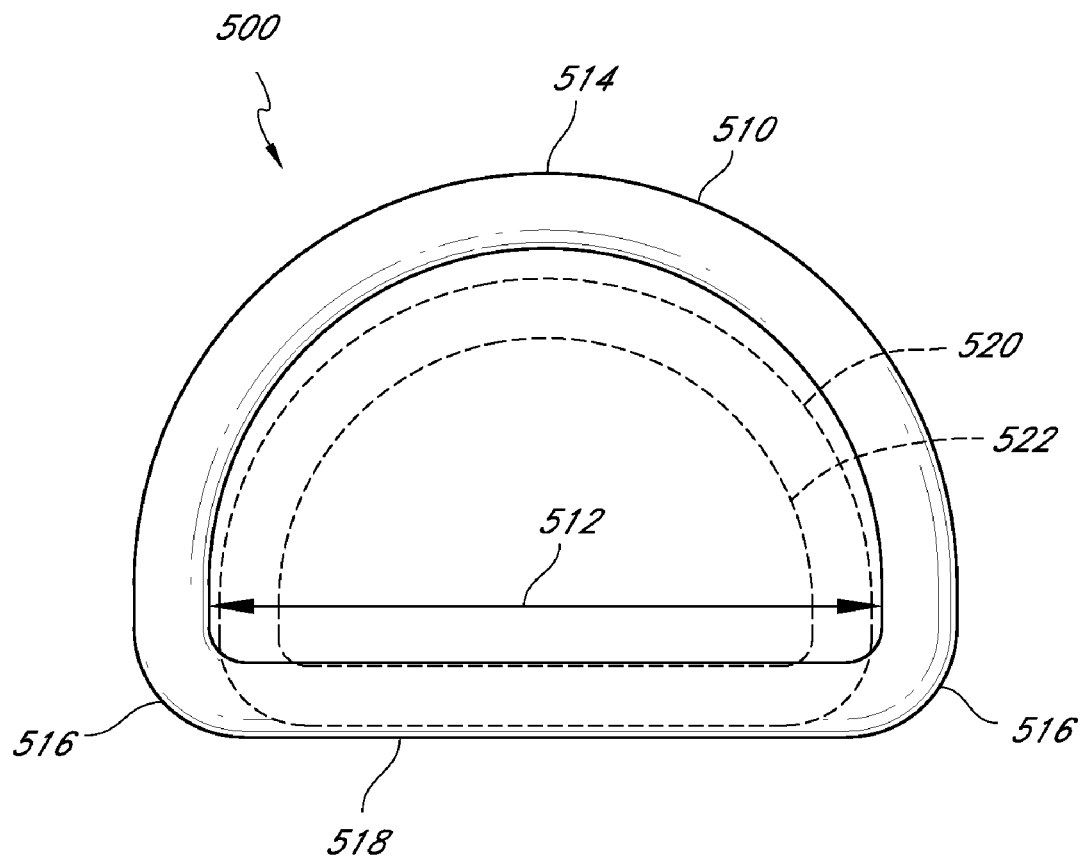
FIG. 5 is a top view of an embodiment of an annuloplasty ring having a substantially D-shaped configuration.

FIG. 5 illustrates a top view of an embodiment of an annuloplasty ring 500 having a D-shaped configuration. The annuloplasty ring 500 includes a continuous tubular member 510 comprising a shape memory material that has a nominal inner transverse dimension indicated by arrow 512 that may contract or shrink upon the activation of the shape memory material by surgically or non-invasive applying energy thereto, as discussed above. The tubular member 510 may comprise a homogeneous shape memory material, such as a shape memory polymer or a shape memory alloy including, for example, a ferromagnetic shape memory alloy.

Alternatively, the tubular member 510 may comprise two or more sections or zones of shape memory material having different temperature response curves. The shape memory response zones may be configured in order to achieve a desired configuration of the annuloplasty ring 500 as a whole when in a contracted state, either fully contracted or partially contracted. For example, the tubular member 510 may have a first zone or section 514 that includes the arched portion of the tubular member that terminates at or near the corners 516 and a second zone or section 518 that includes the substantially straight portion of the tubular member 510 disposed directly between the corners 516.

The annuloplasty ring 500 is shown in a contracted state in FIG. 5 as indicated by the dashed lines 520, 522, which represent contracted states of certain embodiments wherein both the first section 514 and second section 518 of the tubular member 510 have contracted axially. A suturable material (not shown), such as the suturable material 128 shown in FIG. 1, can be disposed about the tubular member 510 and the tubular member 510 may comprise or be coated with an energy absorption enhancement material 126, as discussed above. In some embodiments, the features, dimensions and materials of the annuloplasty ring 500 are the same as or similar to the features, dimensions and materials of the annuloplasty ring 100 discussed above.

Figure 6A:
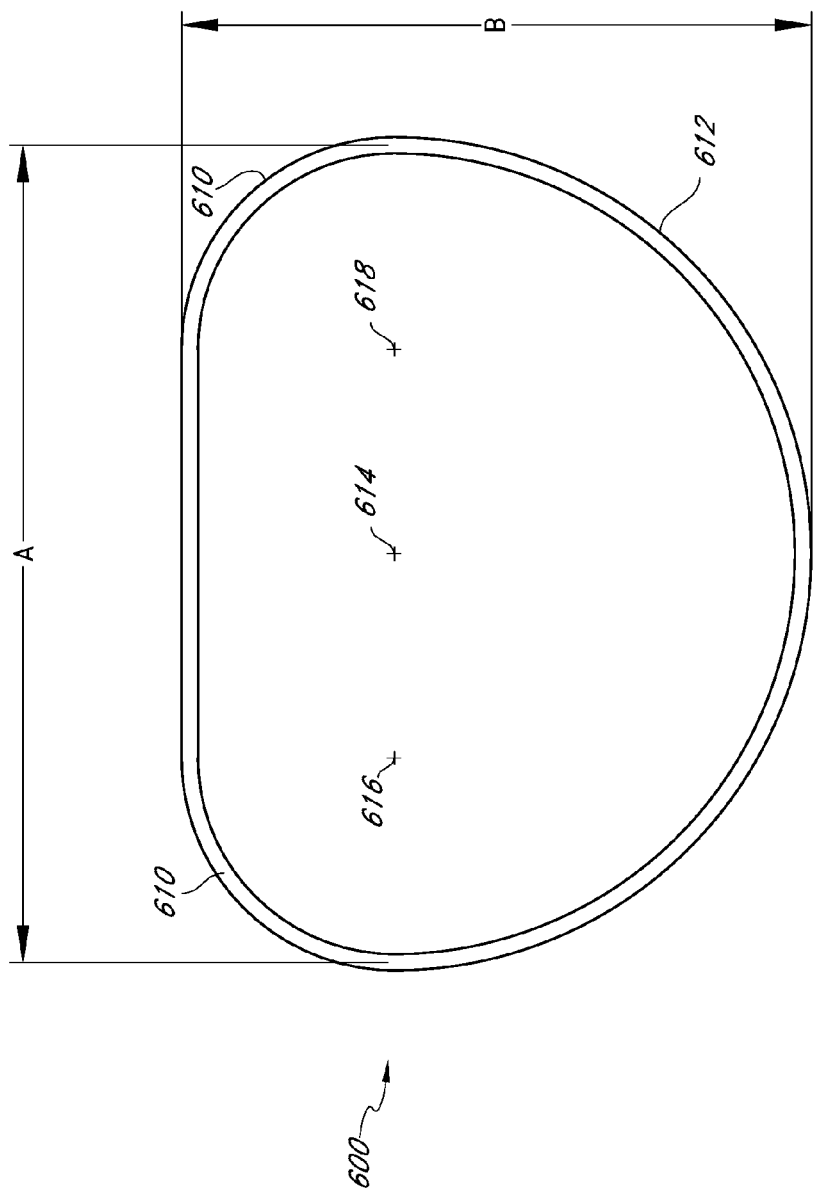
FIG. 6A is a schematic diagram of a top view of an embodiment of a shape memory wire having a substantially D-shaped configuration.

FIG. 6A is a schematic diagram of a top view of an embodiment of a substantially D-shaped wire 600 comprising a shape memory material. The term "wire" is a broad term having its normal and customary meaning and includes, for example, mesh, flat, round, rod-shaped, or band-shaped members. Suitable shape memory materials include shape memory polymers or shape memory alloys including, for example, ferromagnetic shape memory alloys, as discussed above. The wire 600 comprises a substantially linear portion 608, two corner portions 610, and a substantially semi-circular portion 612.

For purposes of discussion, the wire 600 is shown relative to a first reference point 614, a second reference point 616 and a third reference point 618. The radius of the substantially semi-circular portion 612 is defined with respect to the first reference point 614 and the corner portions 610 are respectively defined with respect to the second reference point 616 and the third reference point 618. Also for purposes of discussion, FIG. 6A shows a first transverse dimension A, a second transverse dimension B.

In some embodiments, the first transverse dimension A is in a range between approximately 20.0 mm and approximately 40.0 mm, the second transverse dimension B is in a range between approximately 10.0 mm and approximately 25.0 mm. In some embodiments, the wire 600 comprises a rod having a diameter in a range between approximately 0.45 mm and approximately 0.55 mm, the radius of each corner portion 610 is in a range between approximately 5.8 mm and 7.2 mm, and the radius of the substantially semi-circular portion 612 is in a range between approximately 11.5 mm and approximately 14.0 mm. In certain other such embodiments, the wire 600 comprises a rod having a diameter in a range between approximately 0.90 mm and approximately 1.10 mm, the radius of each corner portion 610 is in a range between approximately 6.1 mm and 7.4 mm, and the radius of the substantially semi-circular portion 612 is in a range between approximately 11.7 mm and approximately 14.3 mm.

In certain other embodiments, the first transverse dimension A is in a range between approximately 26.1 mm and approximately 31.9 mm, the second transverse dimension B is in a range between approximately 20.3 mm and approximately 24.9 mm. In some embodiments, the wire 600 comprises a rod having a diameter in a range between approximately 0.4 mm and approximately 0.6 mm, the radius of each corner portion 610 is in a range between approximately 6.7 mm and 8.3 mm, and the radius of the substantially semi-circular portion 612 is in a range between approximately 13.3 mm and approximately 16.2 mm. In certain other such embodiments, the wire 600 comprises a rod having a diameter in a range between approximately 0.90 mm and approximately 1.10 mm, the radius of each corner portion 610 is in a range between approximately 6.9 mm and 8.5 mm, and the radius of the substantially semi-circular portion 612 is in a range between approximately 13.5 mm and approximately 16.5 mm.

In certain embodiments, the wire 600 comprises a NiTi alloy configured to transition to its austenite phase when heated so as to transform to a memorized shape, as discussed above. In some embodiments, the first transverse dimension A of the wire 600 is configured to be reduced by approximately 10% to 25% when transitioning to the austenite phase. In some embodiments, the austenite start temperature $A_s$ is in a range between approximately 33° C. and approximately 43° C., the austenite finish temperature $A_f$ is in a range between approximately 45° C. and approximately 55° C., the martensite start temperature $M_s$ is less than approximately 30° C., and the martensite finish temperature $M_f$ is greater than approximately 20° C. In other embodiments, the austenite finish temperature $A_f$ is in a range between approximately 48.75° C. and approximately 51.25° C. Some embodiments can include other start and finish temperatures for martensite, rhombohedral and austenite phases as described herein.

FIGS. 6B-6E are schematic diagrams of side views of the shape memory wire 600 of FIG. 6A. In addition to expanding and/or contracting the first transverse dimension A and/or the second transverse dimension B when transitioning to the austenite phase, in certain embodiments the shape memory wire 600 is configured to change shape in a third dimension perpendicular to the first transverse dimension A and the second transverse dimension B. For example, in some embodiments, the shape memory wire 600 is substantially planar or flat in the third dimension, as shown in FIG. 6B, when implanted into a patient's body. Then, after implantation, the shape memory wire 600 is activated such that it expands or contracts in the first transverse dimension A and/or the second transverse dimension B and flexes or bows in the third dimension such that it is no longer planar, as shown in FIG. 6C. Such bowing may be symmetrical as shown in FIG. 6C or asymmetrical as shown in FIG. 6D to accommodate the natural shape of the annulus.

In some embodiments, the shape memory wire 600 is configured to bow in the third dimension a distance in a range between approximately 2 mm and approximately 10 mm. In some embodiments, the shape memory wire 600 is implanted so as to bow towards the atrium when implanted around a cardiac valve annulus to accommodate the natural shape of the annulus. In some embodiments, the shape memory wire 600 is configured to bow towards the ventricle when implanted around a cardiac valve to accommodate the natural shape of the annulus.

In some embodiments, the shape memory wire 600 is bowed in the third dimension, as shown in FIG. 6C, when implanted into the patient's body. Then, after implantation, the shape memory wire 600 is activated such that it expands or contracts in the first transverse dimension A and/or the second transverse dimension B and further flexes or bows in the third dimension, as shown in FIG. 6E. In some embodiments, the shape memory wire 600 is bowed in the third dimension, as shown in FIG. 6C, when implanted into the patient's body. Then, after implantation, the shape memory wire 600 is activated such that it expands or contracts in the first transverse dimension A and/or the second transverse dimension B and changes shape in the third dimension so as to become substantially flat, as shown in FIG. 6B. An artisan will recognize from the disclosure herein that other annuloplasty rings disclosed herein can also be configured to bow or change shape in a third dimension so as to accommodate or further reinforce a valve annulus.

Figure 7A:
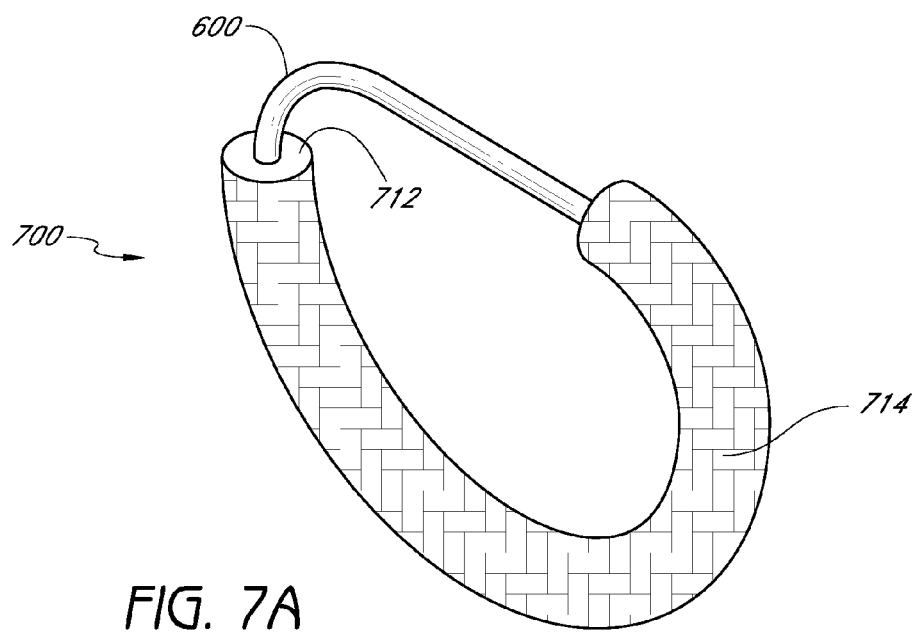
FIG. 7A is a perspective view in partial section of an embodiment of an annuloplasty ring comprising the shape memory wire of FIG. 6A.

FIG. 7A is a perspective view illustrating portions of an embodiment of an annuloplasty ring 700 comprising the wire 600 shown in FIG. 6A. The wire 600 is covered by a flexible material 712 such as silicone rubber and a suturable material 714 such as woven polyester cloth, Dacron®, woven velour, polyurethane, polytetrafluoroethylene (PTFE), heparin-coated fabric, or other biocompatible material. In some embodiments, the suturable material 714 comprises a biological material such as bovine or equine pericardium, homograft, patient graft, or cell-seeded tissue. For illustrative purposes, portions of the flexible material 712 and the suturable material 714 are not shown in FIG. 7A to show the wire 600. However, in certain embodiments, the flexible material 712 and the suturable material 714 are continuous and cover substantially the entire wire 600. Although not shown, in some embodiments, the wire 600 can be coated with an energy absorption enhancement material, as discussed above.

Figure 7B:
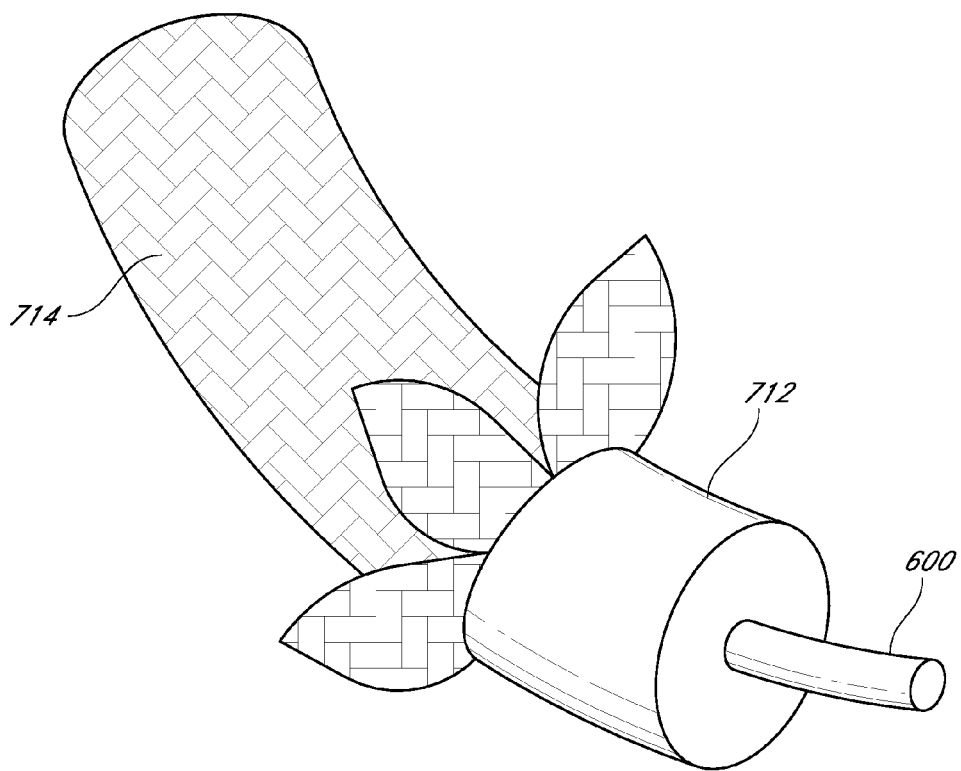
FIG. 7B is a perspective view in partial section of a portion of the annuloplasty ring of FIG. 7A.

FIG. 7B is an enlarged perspective view of a portion of the annuloplasty ring 700 shown in FIG. 7A. For illustrative purposes, portions of the flexible material 712 are not shown to expose the wire 600 and portions of the suturable material 714 are shown peeled back to expose the flexible material 712. In some embodiments, the diameter of the flexible material 712 is in a range between approximately 2.5 mm and approximately 4 mm. FIG. 7B shows the wire 600 substantially centered within the circumference of the flexible material 712. However, in some embodiments, the wire 600 is offset within the circumference of the flexible material 712 to allow more space for sutures.

Figure 8:
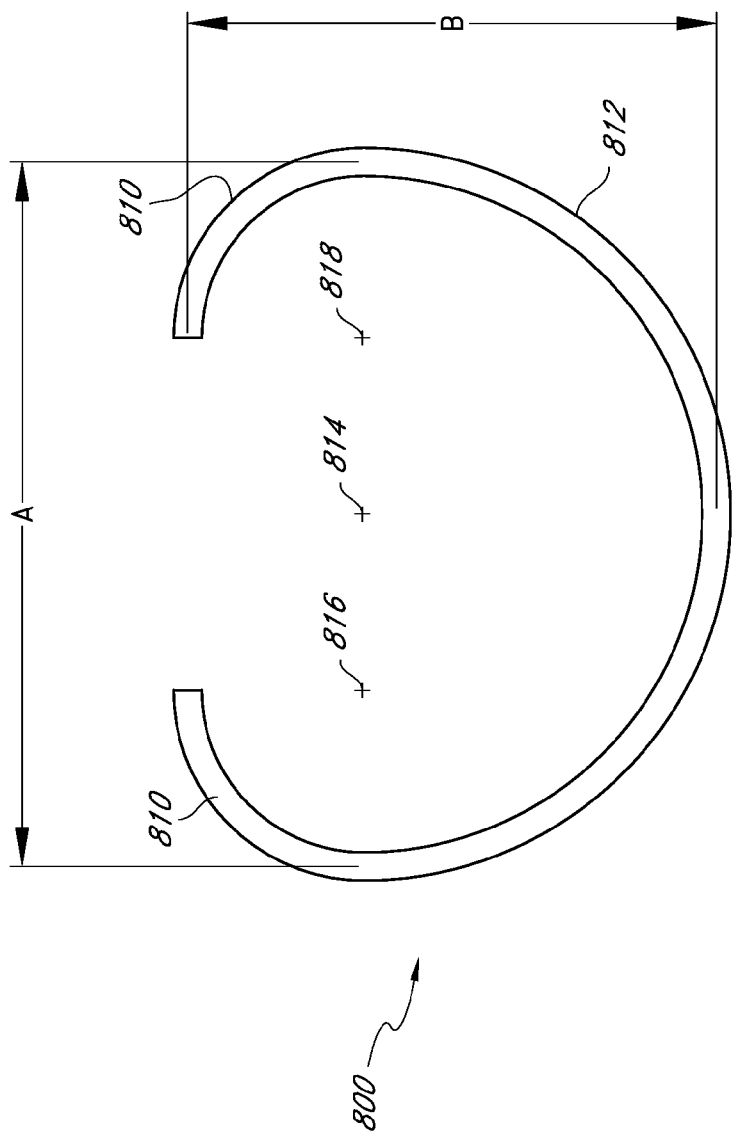
FIG. 8 is a schematic diagram of an embodiment of a shape memory wire having a substantially C-shaped configuration.

FIG. 8 is a schematic diagram of an embodiments of a substantially C-shaped wire 800 comprising a shape memory material. Suitable shape memory materials include shape memory polymers or shape memory alloys including, for example, ferromagnetic shape memory alloys, as discussed above. The wire 800 comprises two corner portions 810, and a substantially semi-circular portion 812.

For purposes of discussion, the wire 800 is shown relative to a first reference point 814, a second reference point 816 and a third reference point 818. The radius of the substantially semi-circular portion 812 is defined with respect to the first reference point 814 and the corner portions 810 are respectively defined with respect to the second reference point 816 and the third reference point 818. Also for purposes of discussion, FIG. 8 shows a first transverse dimension A and a second transverse dimension B. In certain embodiments, the wire 800 comprises a rod having a diameter and dimensions A and B as discussed above in relation to FIG. 6A.

In some embodiments, the wire 800 comprises a NiTi alloy configured to transition to its austenite phase when heated so as to transform to a memorized shape, as discussed above. In some embodiments, the first transverse dimension A of the wire 800 is configured to be reduced by approximately 10% to 25% when transitioning to the austenite phase. In some embodiments, the austenite start temperature $A_s$ is in a range between approximately 33° C. and approximately 43° C., the austenite finish temperature $A_f$ is in a range between approximately 45° C. and approximately 55° C., the martensite start temperature $M_s$ is less than approximately 30° C., and the martensite finish temperature $M_f$ is greater than approximately 20° C. In other embodiments, the austenite finish temperature $A_f$ is in a range between approximately 48.75° C. and approximately 51.25° C.

Figure 9A:
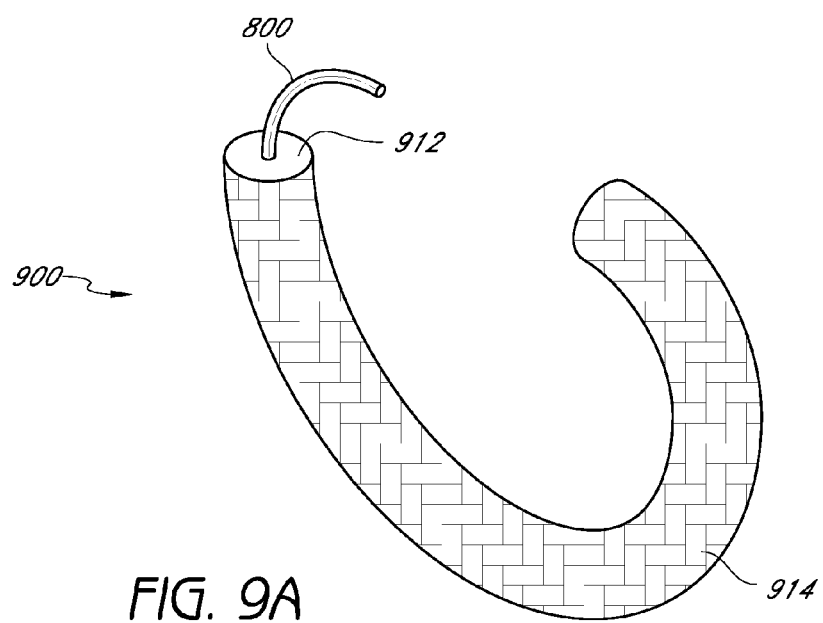
FIG. 9A is a perspective view in partial section of an embodiment of an annuloplasty ring comprising the shape memory wire of FIG. 8.

FIG. 9A is a perspective view illustrating portions of an embodiment of an annuloplasty ring 900 comprising the wire 800 shown in FIG. 8. The wire 800 is covered by a flexible material 912 such as silicone rubber and a suturable material 914 such as woven polyester cloth, Dacron®, woven velour, polyurethane, polytetrafluoroethylene (PTFE), heparin-coated fabric, or other biocompatible material. In other embodiments, the suturable material 914 comprises a biological material such as bovine or equine pericardium, homograft, patient graft, or cell-seeded tissue. For illustrative purposes, portions of the flexible material 912 and the suturable material 914 are not shown in FIG. 9A to show the wire 800. However, in some embodiments, the flexible material 912 and the suturable material 914 cover substantially the entire wire 800. Although not shown, in some embodiments, the wire 800 is coated with an energy absorption enhancement material, as discussed above.

Figure 9B:
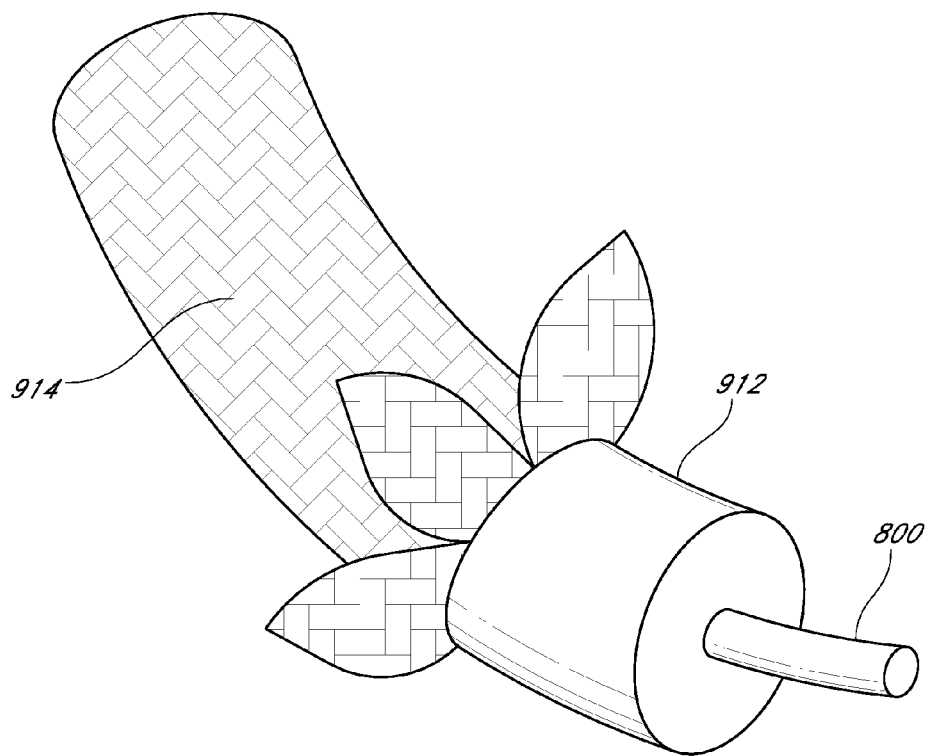
FIG. 9B is a perspective view in partial section of a portion of the annuloplasty ring of FIG. 9A.

FIG. 9B is an enlarged perspective view of a portion of the annuloplasty ring 900 shown in FIG. 9A. For illustrative purposes, portions of the flexible material 912 are not shown to expose the wire 800 and portions of the suturable material 914 are shown peeled back to expose the flexible material 912. In some embodiments, the diameter of the flexible material 912 is in a range between about 2 mm and about 4 mm. FIG. 9B shows the wire 800 substantially centered within the circumference of the flexible material 912. However, in some embodiments, the wire 800 is offset within the circumference of the flexible material 912 to allow more space for sutures.

Figure 10A:
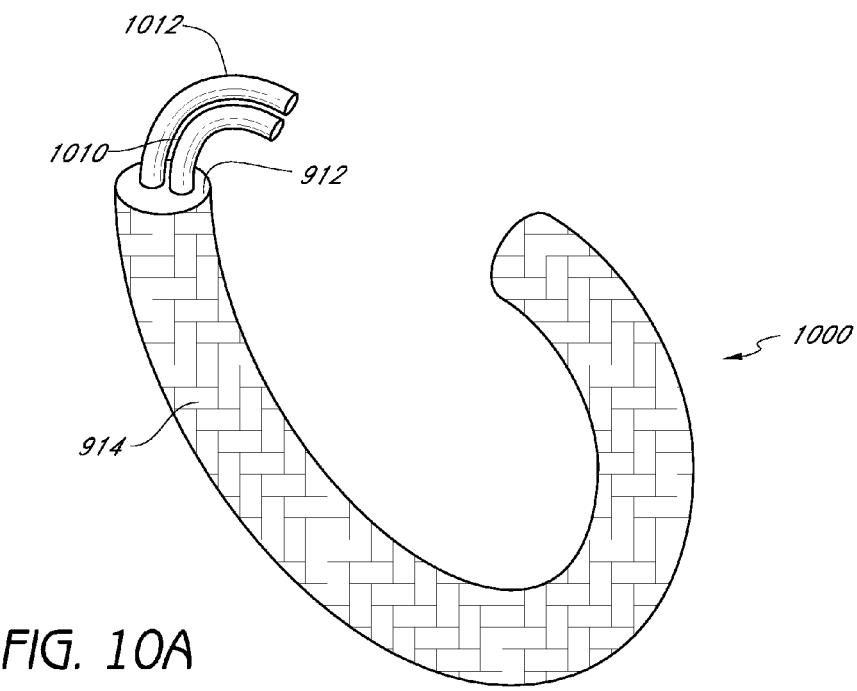
FIG. 10A is a perspective view in partial section of an embodiment of an annuloplasty ring comprising a first shape memory wire and a second shape memory wire.
Figure 10B:
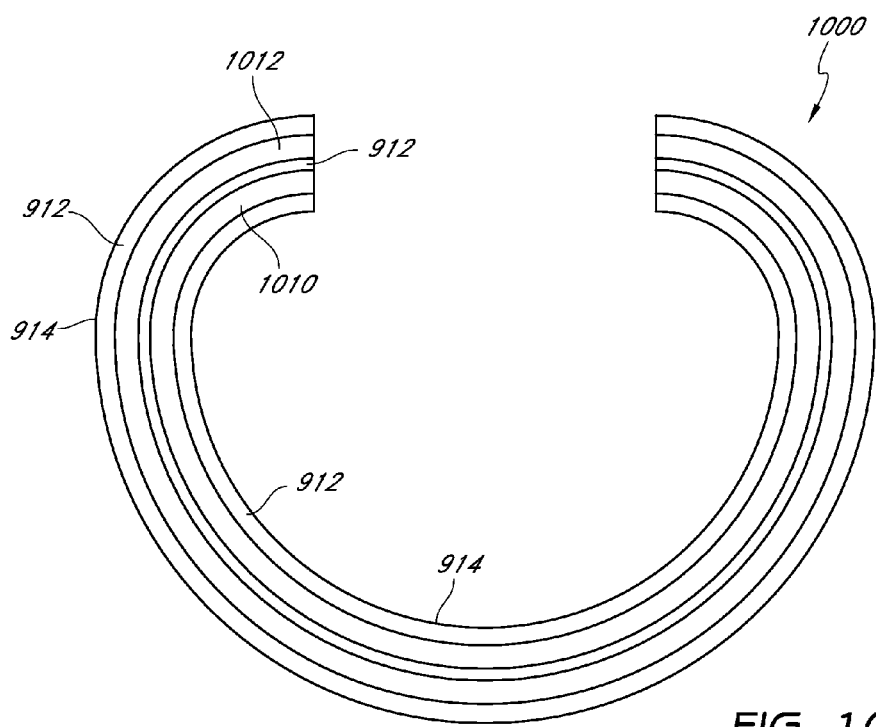
FIG. 10B is a top cross-sectional view of the annuloplasty ring of FIG. 10A.

FIG. 10A is a perspective view illustrating portions of an annuloplasty ring 1000 configured to contract and expand. FIG. 10B is a top cross-sectional view of the annuloplasty ring 1000. As discussed above, after the annuloplasty ring 1000 has been contracted, it may become necessary to expand the annuloplasty ring 1000. For example, the annuloplasty ring 1000 may be implanted in a child with an enlarged heart. When the size of the heart begins to recover to its natural size, the annuloplasty ring 1000 can be contracted. Then, as the child gets older and the heart begins to grow, the annuloplasty ring 1000 can be enlarged as needed.

The annuloplasty ring 1000 comprises a first shape memory wire 1010 for contracting the annuloplasty ring 1000 and a second shape memory wire 1012 for expanding the annuloplasty ring 1000. The first and second shape memory wires, 1010, 1012 are covered by the flexible material 912 and the suturable material 914 shown in FIGS. 9A-9B. For illustrative purposes, portions of the flexible material 912 and the suturable material 914 are not shown in FIG. 10A to show the shape memory wires 1010, 1012. However, as schematically illustrated in FIG. 10B, in some embodiments, the flexible material 912 and the suturable material 914 substantially cover the first and second shape memory wires 1010, 1012. As discussed below, the flexible material 912 operatively couples the first shape memory wire 1010 and the second shape memory wire 1012 such that a shape change in one will mechanically effect the shape of the other. The first and second shape memory wires 1010, 1012 each comprise a shape memory material, such as the shape memory materials discussed above. However, the first and second shape memory wires 1010, 1012 are activated at different temperatures.

In some embodiments, the annuloplasty ring 1000 is heated to a first temperature that causes the first shape memory wire 1010 to transition to its austenite phase and contract to its memorized shape. At the first temperature, the second shape memory wire 1012 is in its martensite phase and is substantially flexible as compared the contracted first shape memory wire 1010. Thus, when the first shape memory wire 1010 transitions to its austenite phase, it exerts a sufficient force on the second shape memory wire 1012 through the flexible material 912 to deform the second shape memory wire 1012 and cause the annuloplasty ring 1000 to contract.

The annuloplasty ring 1000 can be expanded by heating the annuloplasty ring to a second temperature that causes the second shape memory wire 1012 to transition to its austenite phase and expand to its memorized shape. In some embodiments, the second temperature is higher than the first temperature. Thus, at the second temperature, both the first and second shape memory wires 1010, 1012 are in their respective austenite phases. In some embodiments, the diameter of the second shape memory wire 1012 is sufficiently larger than the diameter of the first shape memory wire 1010 such that the second memory shape wire 1012 exerts a greater force to maintain its memorized shape in the austenite phase than the first shape memory wire 1010. Thus, the first shape memory wire 1010 is mechanically deformed by the force of the second memory shape wire 1012 and the annuloplasty ring 1000 expands.

In some embodiments, the first memory shape wire 1010 is configured to contract by approximately 10% to 25% when transitioning to its austenite phase. In some embodiments, the first memory shape wire 1010 has an austenite start temperature $A_s$ in a range between approximately 33° C. and approximately 43° C., an austenite finish temperature $A_f$ in a range between approximately 45° C. and approximately 55° C., a martensite start temperature $M_s$ less than approximately 30° C., and a martensite finish temperature $M_f$ greater than approximately 20° C. In some embodiments, the austenite finish temperature $A_f$ of the first memory shape wire 1010 is in a range between approximately 48.75° C. and approximately 51.25° C.

In some embodiments, the second memory shape wire 1012 is configured to expand by approximately 10% to 25% when transitioning to its austenite phase. In some embodiments, the second memory shape wire 1010 has an austenite start temperature $A_s$ in a range between approximately 60° C. and approximately 70° C., an austenite finish temperature $A_f$ in a range between approximately 65° C. and approximately 75° C., a martensite start temperature $M_s$ less than approximately 30° C., and a martensite finish temperature $M_f$ greater than approximately 20° C. In some embodiments, the austenite finish temperature $A_f$ of the first memory shape wire 1010 is in a range between approximately 68.75 degrees Celsius and approximately 71.25 degrees Celsius.

Figure 11A:
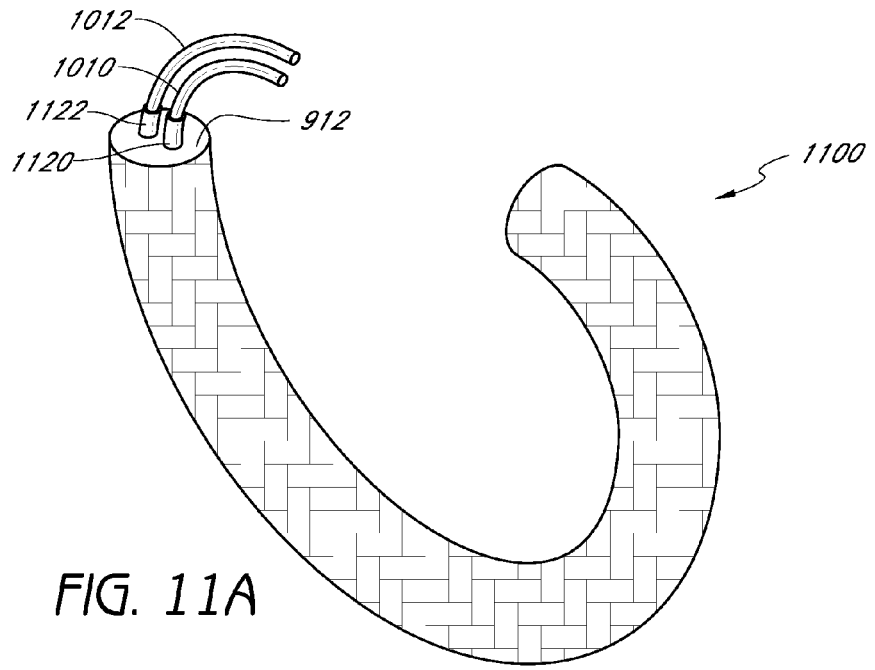
FIG. 11A is a perspective view in partial section of an embodiment of an annuloplasty ring comprising a first shape memory wire and a second shape memory wire.
Figure 11B:
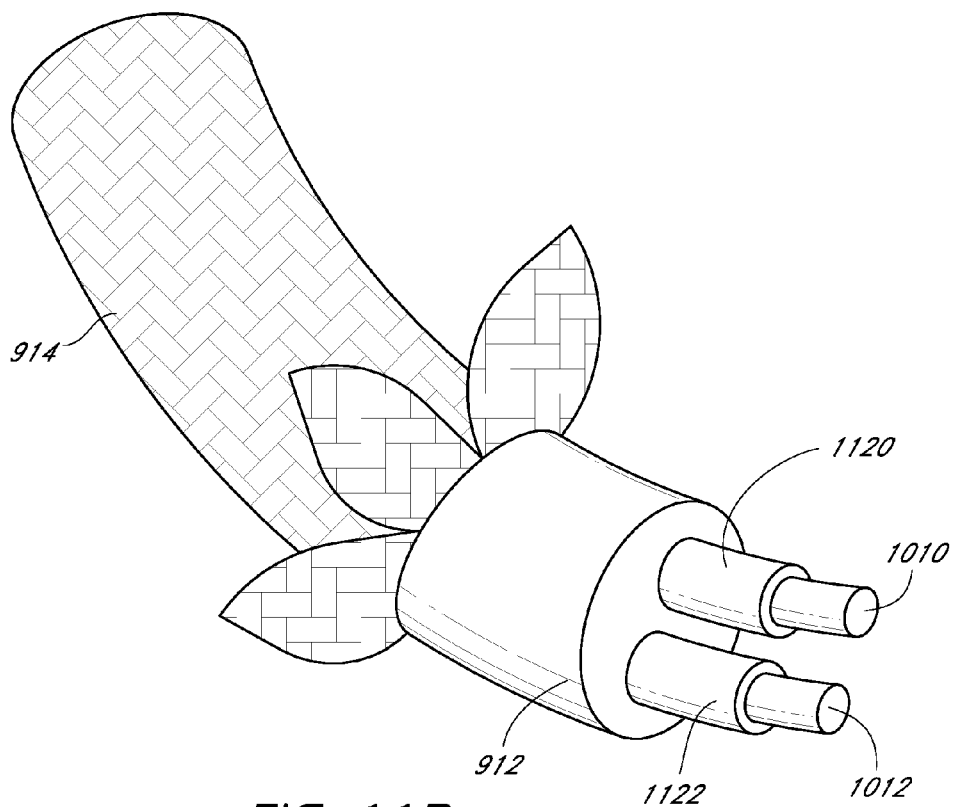
FIG. 11B is a top cross-sectional view of the annuloplasty ring of FIG. 11A.

FIG. 11A is a perspective view illustrating portions of an embodiments of an annuloplasty ring 1100 comprising the first shape memory wire 1010 for contraction, the second shape memory wire 1012 for expansion, the flexible material 912 and the suturable material 914 shown in FIGS. 10A-10B. For illustrative purposes, portions of the flexible material 912 and the suturable material 914 are not shown in FIG. 11A to show the shape memory wires 1010, 1012. However, in some embodiments, the flexible material 912 and the suturable material 914 substantially cover the first and second shape memory wires 1010, 1012. FIG. 11B is an enlarged perspective view of a portion of the annuloplasty ring 1100 shown in FIG. 11A. For illustrative purposes, portions of the flexible material 912 are not shown to expose the first and second shape memory wires 1010, 1012 and portions of the suturable material 914 are shown peeled back to expose the flexible material 912.

The first shape memory wire 1010 comprises a first coating 1120 and the second shape memory wire 1012 comprises a second coating 1122. In some embodiments, the first coating 1120 and the second coating 1122 each comprise silicone tubing configured to provide suture attachment to a heart valve annulus. In some embodiments, the first coating 1120 and the second coating 1122 each comprise an energy absorption material, such as the energy absorption materials discussed above. In some embodiments, the first coating 1120 heats when exposed to a first form of energy and the second coating 1122 heats when exposed to a second form of energy. For example, the first coating 1120 may heat when exposed to MRI energy and the second coating 1122 may heat when exposed to HIFU energy. As another example, the first coating 1120 may heat when exposed to RF energy at a first frequency and the second coating 1122 may heat when exposed to RF energy at a second frequency. Thus, the first shape memory wire 1010 and the second shape memory wire 1012 can be activated independently such that one transitions to its austenite phase while the other remains in its martensite phase, resulting in contraction or expansion of the annuloplasty ring 1100.

Figure 12:
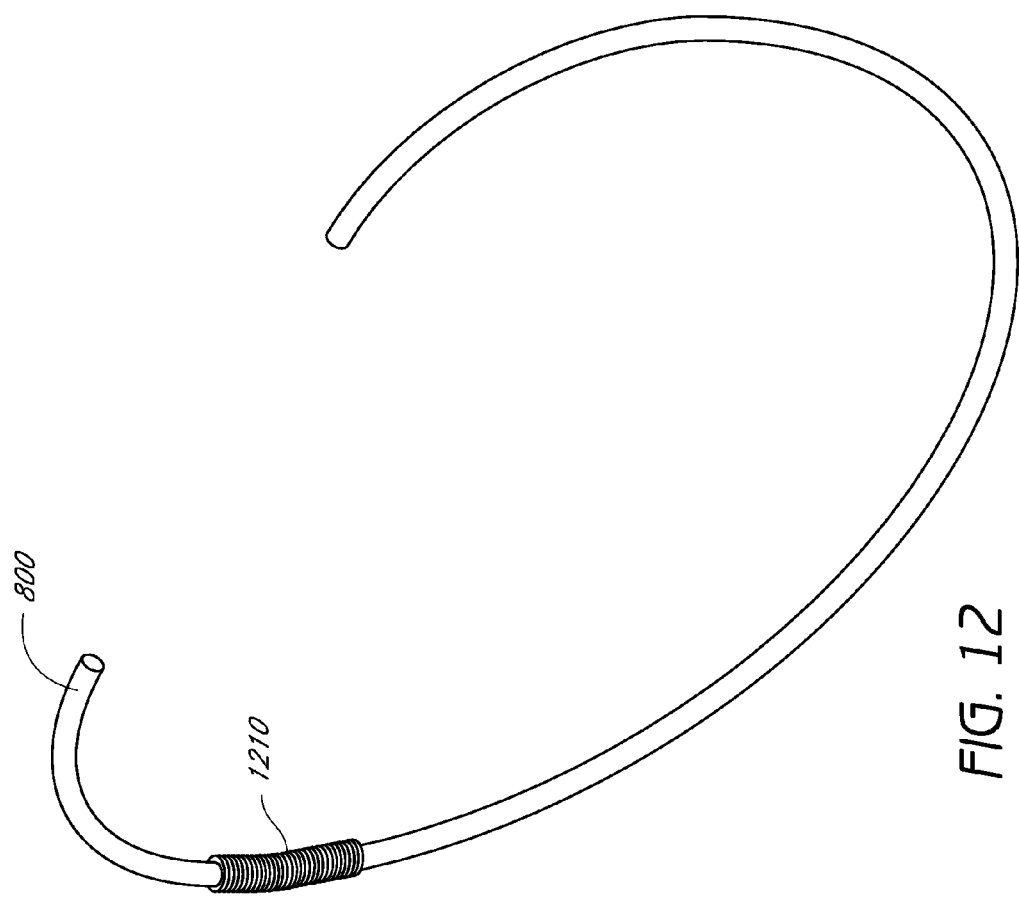
FIG. 12 is a perspective view of an embodiment of a shape memory wire wrapped in a coil.

FIG. 12 is a perspective view of an embodiment of a shape memory wire 800, such as the wire 800 shown in FIG. 8, wrapped in an electrically conductive coil 1210. The coil 1210 is wrapped around a portion of the wire 800 where it is desired to focus energy and heat the wire 800. In some embodiments, the coil 1210 is wrapped around approximately 5% to approximately 15% of the wire 800. In other embodiments, the coil 1210 is wrapped around approximately 15% to approximately 70% of the wire 800. In some embodiments, the coil 1210 is wrapped around substantially the entire wire 800. Although not shown, in certain embodiments, the wire 800 also comprises a coating comprising an energy absorption material, such as the energy absorption materials discussed above. The coating may or may not be covered by the coil 1210.

As discussed above, an electrical current can be non-invasively induced in the coil 1210 using electromagnetic energy. For example, in some embodiments, a handheld or portable device (not shown) comprising an electrically conductive coil generates an electromagnetic field that non-invasively penetrates the patient's body and induces a current in the coil 1210. The electrical current causes the coil 1210 to heat. The coil 1210, the wire 800 and the coating (if any) are thermally conductive so as to transfer the heat or thermal energy from the coil 1210 to the wire 800. Thus, thermal energy can be directed to the wire 800, or portions thereof, while reducing thermal damage to surrounding tissue.

Figure 13A:
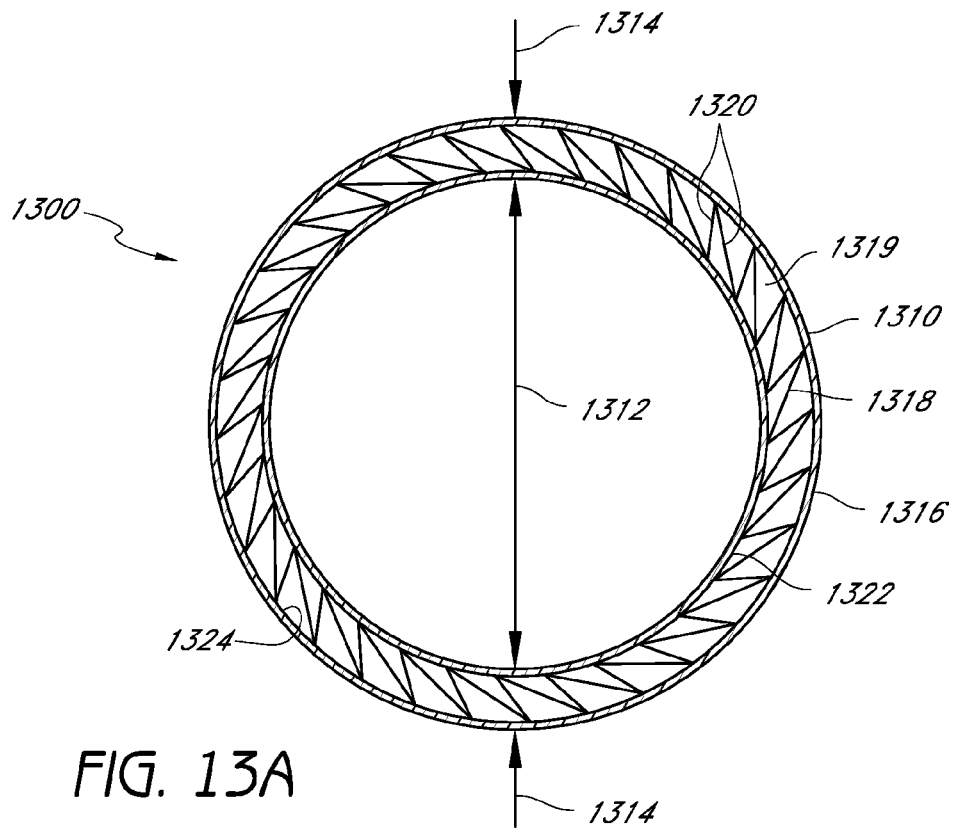
FIGS. 13A and 13B are schematic diagrams illustrating an embodiment of an annuloplasty ring.
Figure 13B:
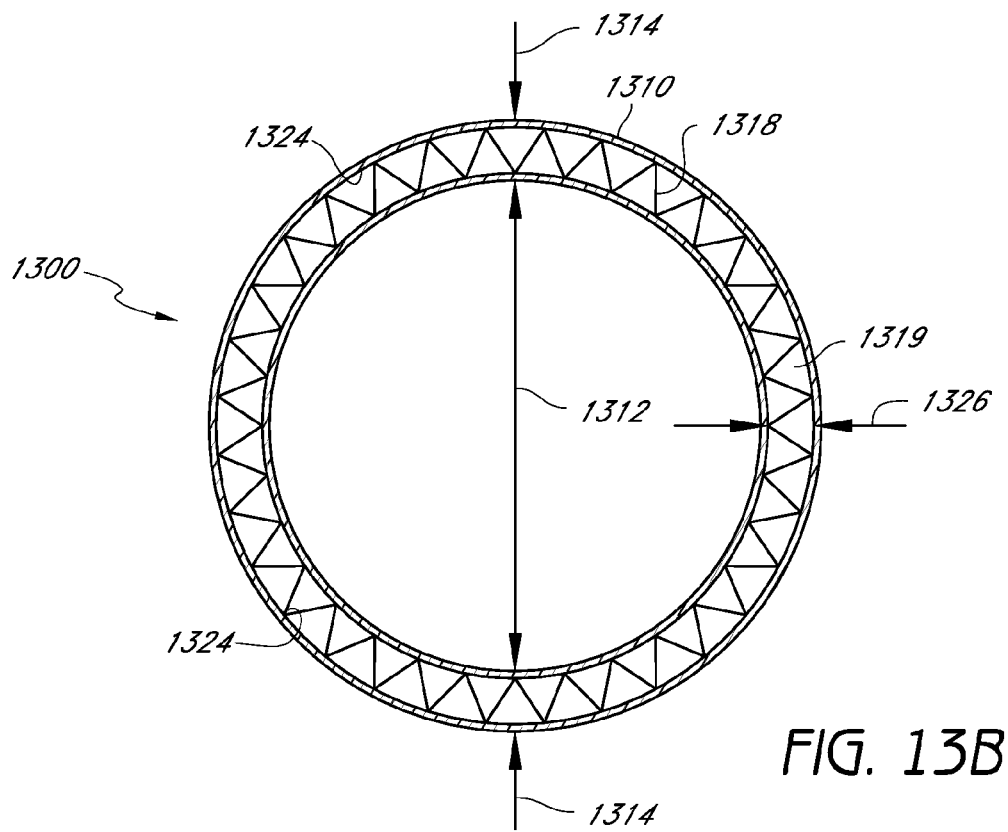

FIGS. 13A and 13B illustrate an embodiment of an annuloplasty ring 1310 having a nominal inner diameter or transverse dimension indicated by arrow 1312 and a nominal outer diameter or transverse dimension indicated by arrows 1314. The ring 1310 includes a tubular member 1316 having a substantially round transverse cross section with an internal shape memory member 1318 disposed within an inner chamber 1319 of the tubular member 1316. The internal shape memory member 1318 is a ribbon or wire bent into a series of interconnected segments 1320. Upon heating of the tubular member 1316 and the internal shape memory member 1318, the inner transverse dimension 1312 becomes smaller due to axial shortening of the tubular member 1316 and an inward radial force applied to an inner chamber surface 1322 of the tubular member 1316 by the internal shape memory member 1318. The internal shape memory member 1318 is expanded upon heating such that the ends of segments 1320 push against the inner chamber surface 1322 and outer chamber surface 1324, as shown by arrow 1326 in FIG. 13B, and facilitate radial contraction of the inner transverse dimension 1312. Thus, activation of the internal shape memory member 1318 changes the relative distance between the against the inner chamber surface 1322 and outer chamber surface 1324.

Although not shown in FIG. 13A or 13B, The inner shape memory member 1318 may also have a heating energy absorption enhancement material, such as one or more of the energy absorption enhancement materials discussed above, disposed about it within the inner chamber 1319. The energy absorption material may also be coated on an outer surface and/or an inner surface of the tubular member 1316. The inner transverse dimension 1312 of the ring 1310 in FIG. 13B is less than the inner transverse dimension 1312 of the ring 1310 shown in FIG. 13A. However, in some embodiments, the outer transverse dimension 1314 is substantially constant in both FIGS. 13A and 13B.

Figure 14:
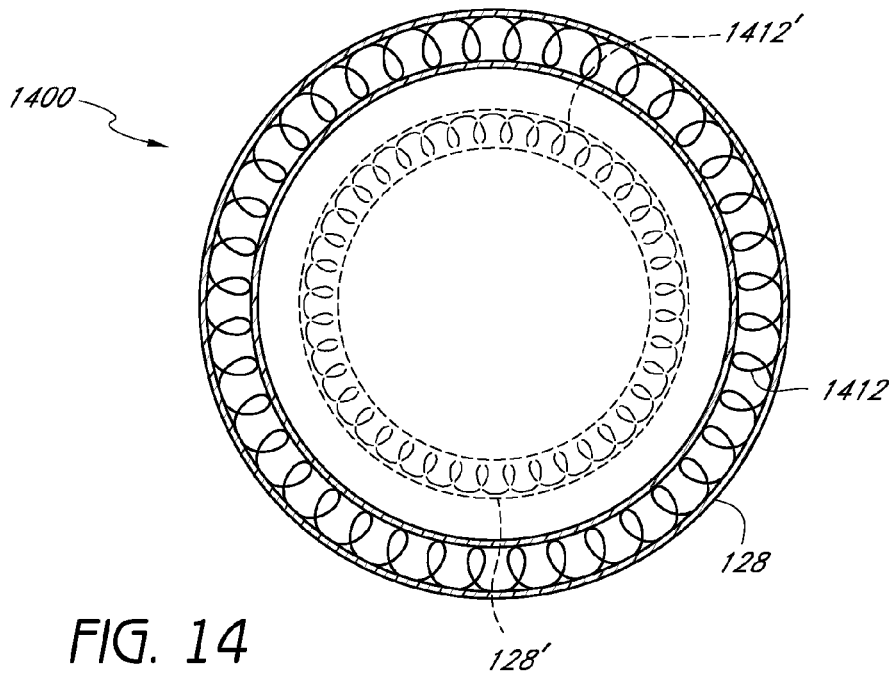
FIG. 14 is a schematic diagram illustrating an embodiment of an annuloplasty ring.
Figure 15:
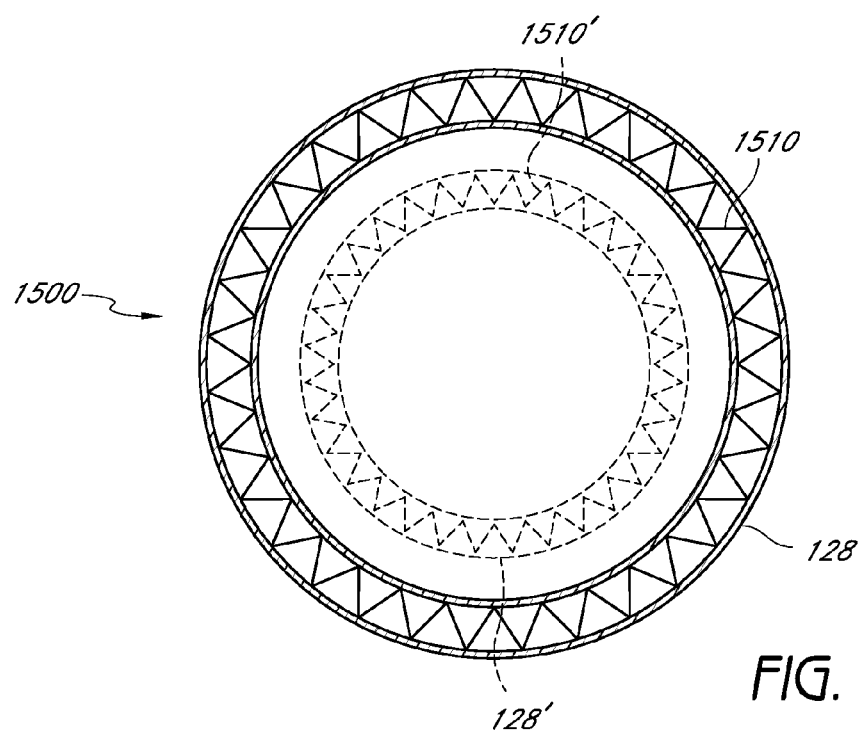
FIG. 15 is a schematic diagram illustrating an embodiment of an annuloplasty ring.

For some indications, it may be desirable for an adjustable annuloplasty ring to have some compliance in order to allow for expansion and contraction of the ring in concert with the expansion and contraction of the heart during the beating cycle or with the hydrodynamics of the pulsatile flow through the valve during the cycle. As such, it may be desirable for an entire annuloplasty ring, or a section or sections thereof, to have some axial flexibility to allow for some limited and controlled expansion and contraction under clinical conditions. FIGS. 14 and 15 illustrate embodiments of adjustable annuloplasty rings that allow some expansion and contraction in a deployed state.

FIG. 14 shows an annuloplasty ring 1400 that is constructed in such a way that it allows mechanical expansion and compression of the ring 1400 under clinical conditions. The ring 1400 includes a coil 1412 made of a shape memory material, such as one or more of the shape memory materials discussed above. The shape memory material or other portion of the ring 1400 may be coated with an energy absorption material, such as the energy absorption materials discussed above. The coil 1412 may have a typical helical structure of a normal spring wire coil, or alternatively, may have another structure such as a ribbon coil. In some embodiments, the coil 1412 is surrounded by a suturable material 128, such as Dacron® or the other suturable materials discussed herein. The coiled structure or configuration of the coil 1412 allows the ring 1400 to expand and contract slightly when under physiological pressures and forces from heart dynamics or hydrodynamics of blood flow through a host heart valve.

For embodiments where the coil 1412 is made of NiTi alloy or other shape memory material, the ring 1400 is responsive to temperature changes which may be induced by the application of heating energy on the coil 1412. In some embodiments, if the temperature is raised, the coil 1412 will contract axially or circumferentially such that an inner transverse dimension of the ring 1400 decreases, as shown by the dashed lines in FIG. 14. In FIG. 14, reference 1412' represents the coil 1412 in its contracted state and reference 128' represents the suturable material 128 in its contracted state around the contracted coil 1412'. In some embodiments, the coil 1412 expands axially or circumferentially such that the inner transverse dimension of the ring 1400 increases. Thus, in some embodiments, the ring 1400 can be expanded and contracted by applying invasive or non-invasive energy thereto.

FIG. 15 illustrates an embodiment of an adjustable annuloplasty ring 1500 that has dynamic compliance with dimensions, features and materials that may be the same as or similar to those of ring 1400. However, the ring 1500 has a zig-zag ribbon member 1510 in place of the coil 1412 in the embodiment of FIG. 14. In some embodiments, if the temperature is raised, the ribbon member 1510 will contract axially or circumferentially such that an inner transverse dimension of the ring 1500 decreases, as shown by the dashed lines in FIG. 15. In FIG. 15, reference 1510' represents the ribbon member 1510 in its contracted state and reference 128' represents the suturable material 128 in its contracted state around the contracted ribbon member 1510'. In some embodiments, the ribbon member 1510 expands axially or circumferentially such that the inner transverse dimension of the ring 1500 increases. Thus, in some embodiments, the ring 1500 can be expanded and contracted by applying invasive or non-invasive energy thereto.

The embodiments of FIGS. 14 and 15 may have a substantially circular configuration as shown in the figures, or may have D-shaped or C-shaped configurations as shown with regard to other embodiments discussed above. In some embodiments, the features, dimensions and materials of rings 1400 and 1500 are the same as or similar to the features, dimensions and materials of the annuloplasty ring 400 discussed above.

Figure 16A:
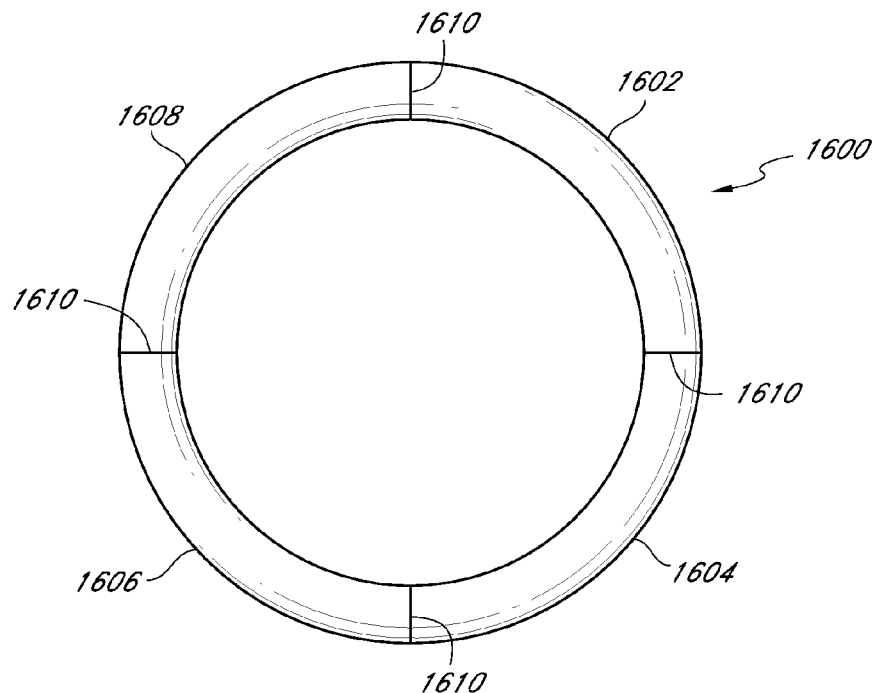
FIGS. 16A and 16B are schematic diagrams illustrating an embodiment of an annuloplasty ring having a plurality of temperature response zones or sections.
Figure 16B:
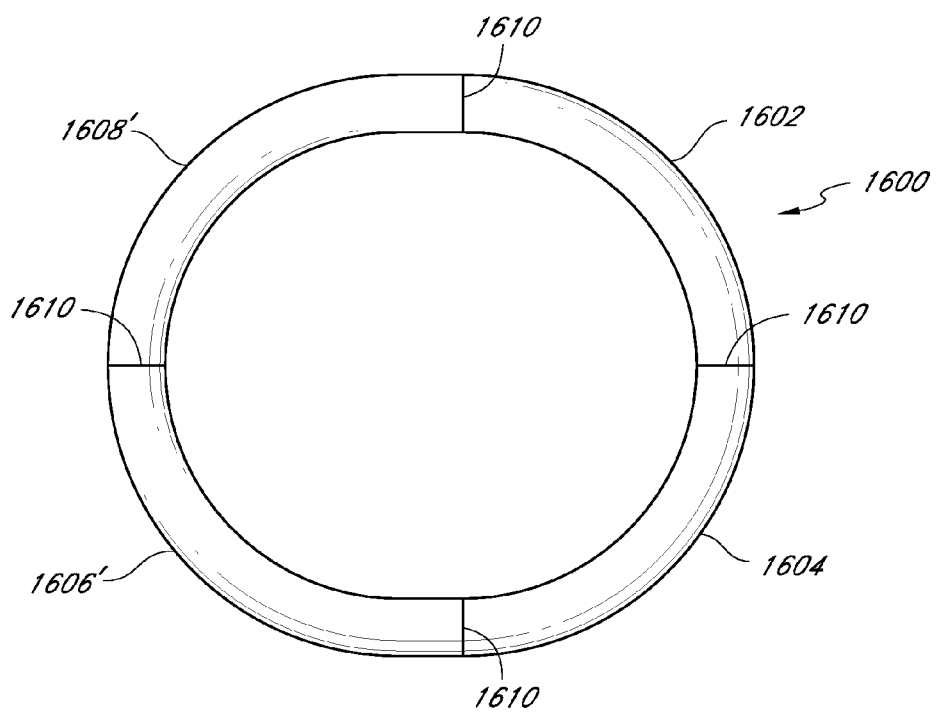

FIGS. 16A and 16B illustrate an embodiments of an annuloplasty ring 1600 that has a substantially circular shape or configuration when in the non-activated state shown in FIG. 16A. The ring 1600 comprises shape memory material or materials which are separated into a first temperature response zone 1602, a second temperature response zone 1604, a third temperature response zone 1606 and a fourth temperature response zone 1608. The zones are axially separated by boundaries 1610. Although the ring 1600 is shown with four zones 1602, 1604, 1606, 1608, an artisan will recognize from the disclosure herein that other embodiments may include two or more zones of the same or differing lengths. For example, in some embodiments, an annuloplasty ring 1600 includes approximately three to approximately eight temperature response zones.

In some embodiments, the shape memory materials of the various temperature response zones 1602, 1604, 1606, 1608 are selected to have temperature responses and reaction characteristics such that a desired shape and configuration can be achieved in vivo by the application of invasive or non-invasive energy, as discussed above. In addition to general contraction and expansion changes, more subtle changes in shape and configuration for improvement or optimization of valve function or hemodynamics may be achieved with such embodiments.

In some embodiments, the first zone 1602 and second zone 1604 of the ring 1600 are made from a shape memory material having a first shape memory temperature response. The third zone 1606 and fourth zone 1608 are made from a shape memory material having a second shape memory temperature response. In some embodiments, the four zones comprise the same shape memory material, such as NiTi alloy or other shape memory material as discussed above, processed to produce the varied temperature response in the respective zones. In some embodiments, two or more of the zones may comprise different shape memory materials. Some embodiments include a combination of shape memory alloys and shape memory polymers in order to achieve the desired results.

In some embodiments, FIG. 16B shows the ring 1600 after heat activation such that it comprises expanded zones 1606', 1608' corresponding to the zones 1606, 1608 shown in FIG. 16A. As schematically shown in FIG. 16A, activation has expanded the zones 1606', 1608' so as to increase the axial lengths of the segments of the ring 1600 corresponding to those zones. In some embodiments, the zones 1606 and 1608 are configured to contract by a similar percentage instead of expand. In some embodiments, the zones 1602, 1604, 1606, 1608 are configured to each have a different shape memory temperature response such that each segment corresponding to each zone 1602, 1604, 1606, 1608 could be activated sequentially.

FIG. 16B schematically illustrates that the zones 1606', 1608' have expanded axially (i.e., from their initial configuration as shown by the zones 1606, 1608 in FIG. 16A). In certain embodiments, the zones 1602, 1604 are configured to be thermally activated to remember a shape memory dimension or size upon reaching a temperature in a range between about 51° C. and about 60° C. In some embodiments, the zones 1606 and 1608 are configured to respond at temperatures in a range between approximately 41° C. and approximately 48° C. Thus, for example, by applying invasive or non-invasive energy, as discussed above, to the ring 1600 until the ring 1600 reaches a temperature of about 41° C. to about 48° C., the zones 1606, 1608 will respond by expanding or contracting by virtue of the shape memory mechanism, and the zones 1602, 1604 will not.

In some embodiments, the zones 1602, 1604 are configured to expand or contract by virtue of the shape memory mechanism at a temperature in a range between approximately 50° C. and approximately 60° C. In some embodiments, the zones 1606, 1608 are configured to respond at a temperature in a range between approximately 39° C. and approximately 45° C.

In some embodiments, the materials, dimensions and features of the annuloplasty ring 1600 and the corresponding zones 1602, 1604, 1606, 1608 have the same or similar features, dimensions or materials as those of the other ring embodiments discussed above. In some embodiments, the features of the annuloplasty ring 1600 can be added to the embodiments discussed above.

Figure 17A:
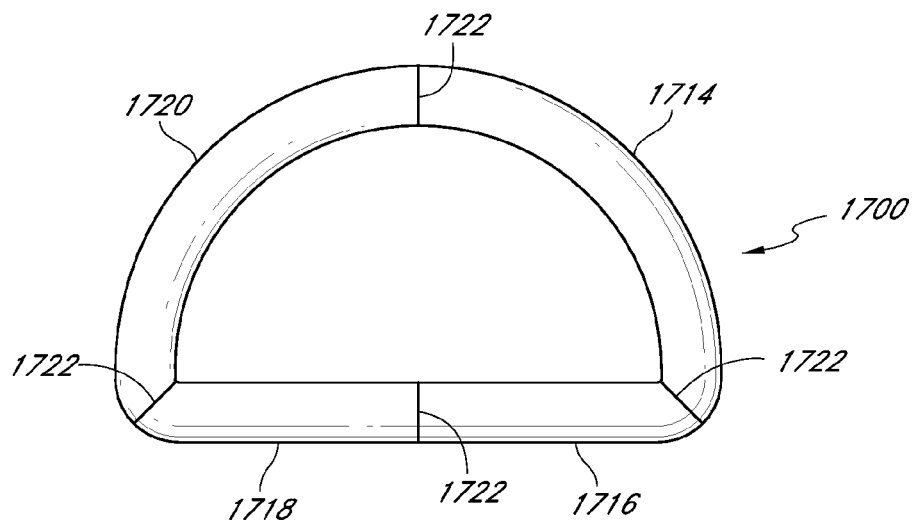
FIGS. 17A and 17B are schematic diagrams illustrating an embodiment of an annuloplasty ring having a plurality of temperature response zones or sections.
Figure 17B:
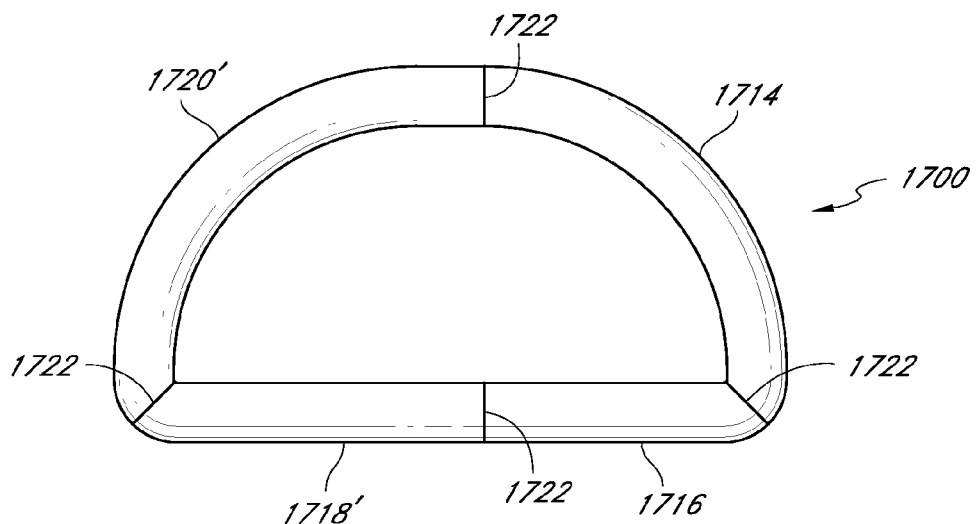

FIGS. 17A and 17B illustrate an embodiment of an annuloplasty ring 1700 that is similar to the annuloplasty ring 1600 discussed above, but having a "D-shaped" configuration. The ring 1700 comprises shape memory material or materials which are separated into a first temperature response zone 1714, a second temperature response zone 1716, a third temperature response zone 1718 and a fourth temperature response zone 1720. The segments defined by the zones 1714, 1716, 1718, 1720 are separated by boundaries 1722. Other than the D-shaped configuration, the ring 1700 according to certain embodiments has the same or similar features, dimensions and materials as the features, dimension and materials of the ring 1600 discussed above.

In some embodiments, FIG. 17B shows the ring 1700 after heat activation such that it comprises expanded zones 1718', 1720' corresponding to the zones 1718, 1720 shown in FIG. 17A. As schematically shown in FIG. 17B, activation has expanded the zones 1718', 1720' by virtue of the shape memory mechanism. The zones 1718, 1720 could also be selectively shrunk or contracted axially by virtue of the same shape memory mechanism for an embodiment having a remembered shape smaller than the nominal shape shown in FIG. 17A. The transverse cross sections of the rings 1600 and 1700 are substantially round, but can also have any other suitable transverse cross sectional configuration, such as oval, square, rectangular or the like.

Figure 18:
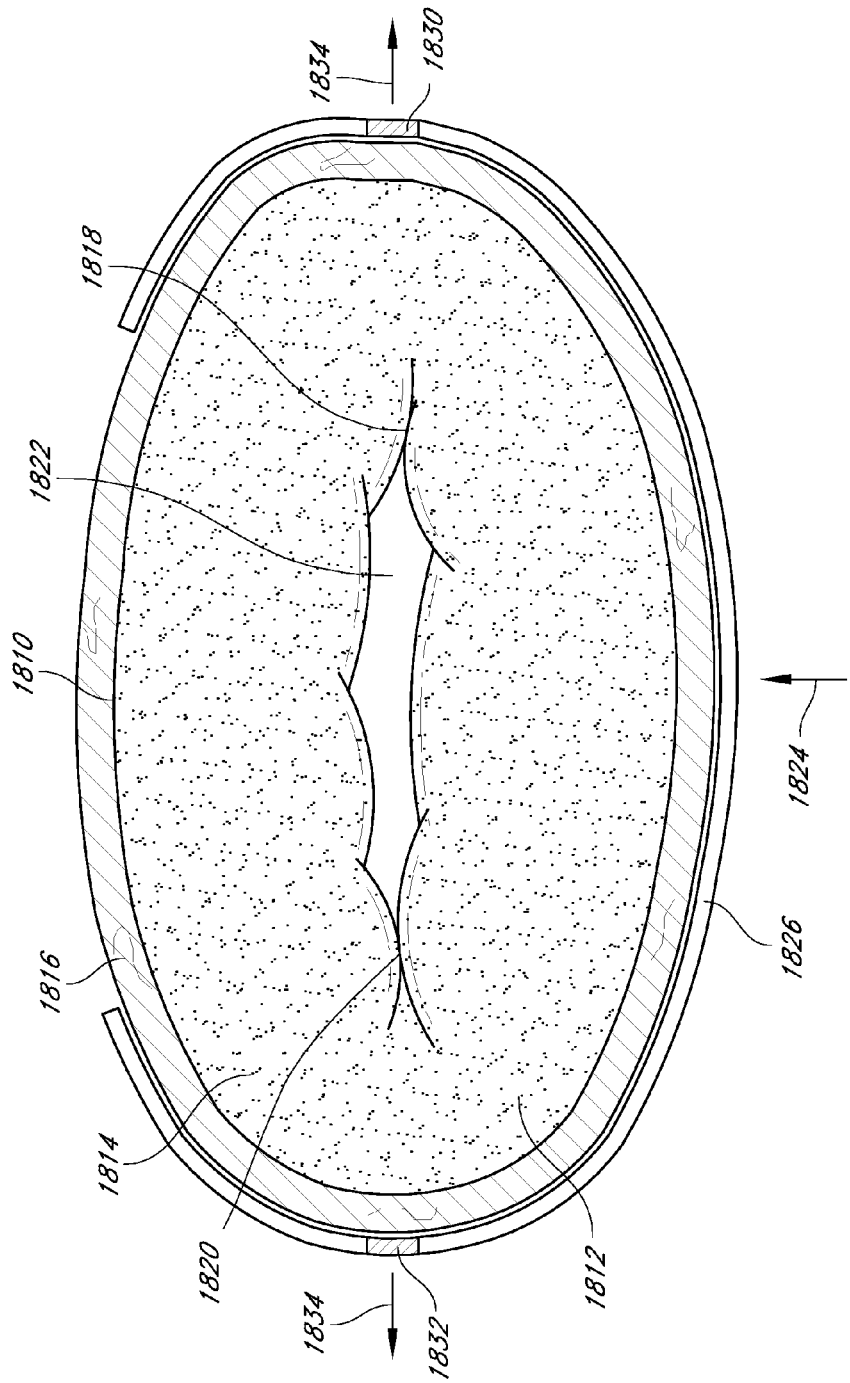
FIG. 18 is a sectional view of a mitral valve with respect to an embodiment of an exemplary annuloplasty ring.

In some situations, it is advantageous to reshape a heart valve annulus in one dimension while leaving another dimension substantially unchanged or reshaped in a different direction. For example, FIG. 18 is a sectional view of a mitral valve 1810 having an anterior (aortic) leaflet 1812, a posterior leaflet 1814 and an annulus 1816. The anterior leaflet 1812 and the posterior leaflet 1814 meet at a first commissure 1818 and a second commissure 1820. When healthy, the annulus 1816 encircles the leaflets 1812, 1814 and maintains their spacing to provide closure of a gap 1822 during left ventricular contraction. When the heart is not healthy, the leaflets 1812, 1814 do not achieve sufficient coaptation to close the gap 1822, resulting in regurgitation. In some embodiments, the annulus 1816 is reinforced so as to push the anterior leaflet 1812 and the posterior leaflet 1814 closer together without substantially pushing the first commissure 1818 and the second commissure 1820 toward one another.

FIG. 18 schematically illustrates an exemplary annuloplasty ring 1826 comprising shape memory material configured to reinforce the annulus 1816. For illustrative purposes, the annuloplasty ring 1826 is shown in an activated state wherein it has transformed to a memorized configuration upon application of invasive or non-invasive energy, as described herein. While the annuloplasty ring 1826 is substantially C-shaped, an artisan will recognize from the disclosure herein that other shapes are possible including, for example, a continuous circular, oval or D-shaped ring.

In some embodiments, the annuloplasty ring 1826 comprises a first marker 1830 and a second marker 1832 that are aligned with the first commissure 1818 and the second commissure 1820, respectively, when the annuloplasty ring 1826 is implanted around the mitral valve 1810. In certain embodiments, the first marker 1830 and the second marker 1832 comprise materials that can be imaged in-vivo using standard imaging techniques. For example, in some embodiments, the markers 1830 comprise radiopaque markers or other imaging materials, as is known in the art. Thus, the markers 1830, 1832 can be used for subsequent procedures for alignment with the annuloplasty ring 1826 and/or the commissures 1818, 1820. For example, the markers 1830, 1832 can be used to align a percutaneous energy source, such as a heated balloon inserted through a catheter, with the annuloplasty ring 1826.

When the shape memory material is activated, the annuloplasty ring 1826 contracts in the direction of the arrow 1824 to push the anterior leaflet 1812 toward the posterior leaflet 1814. Such anterior/posterior contraction improves the coaptation of the leaflets 1812, 1814 such that the gap 1824 between the leaflets 1812, 1814 sufficiently closes during left ventricular contraction. In some embodiments, the annuloplasty ring 1826 also expands in the direction of arrows 1834. Thus, the first commissure 1818 and the second commissure 1820 are pulled away from each other, which draws the leaflets 1812, 1814 closer together and further improves their coaptation. However, in some embodiments, the annuloplasty ring does not expand in the direction of the arrows 1834. In some embodiments, the distance between the lateral portions of the annuloplasty ring 1826 between the anterior portion and the posterior portion (e.g., the lateral portions approximately correspond to the locations of the markers 1830, 1832 in the embodiment shown in FIG. 18) remains substantially the same after the shape memory material is activated.

Figure 19:
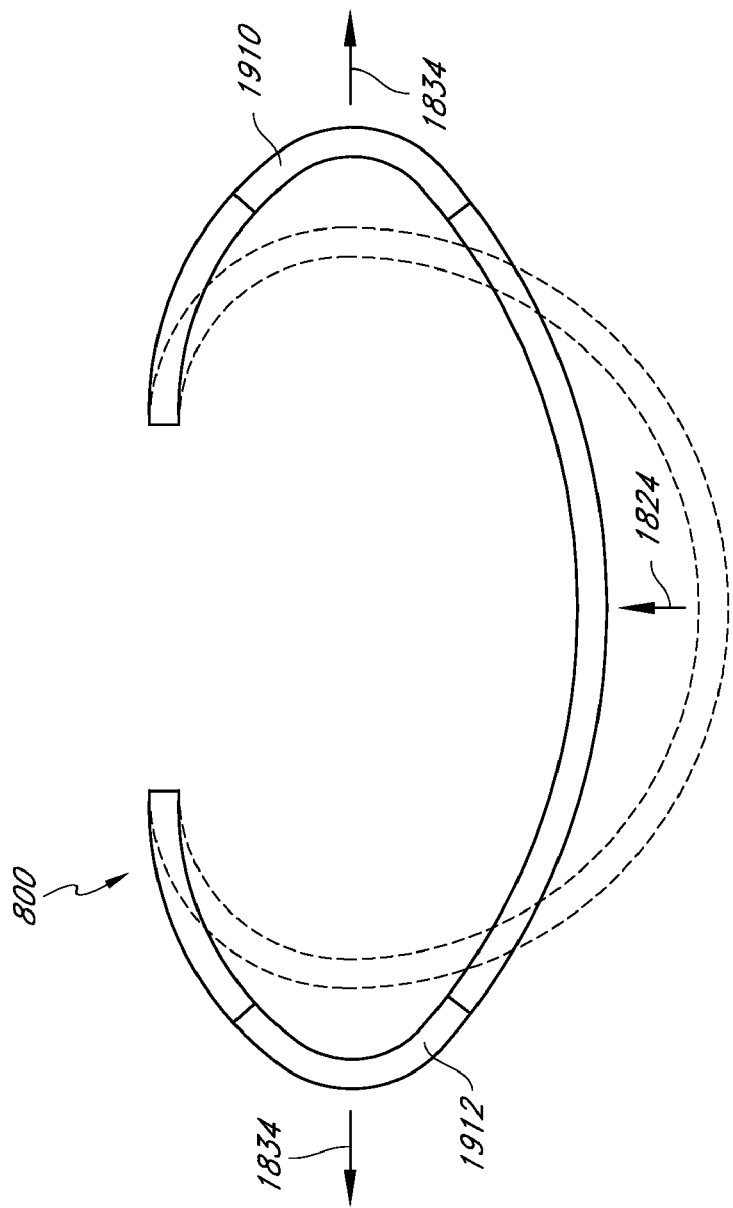
FIG. 19 is a schematic diagram of an embodiment of a substantially C-shaped wire comprising a shape memory material configured to contract in a first direction and expand in a second direction.

FIG. 19 is a schematic diagram of an embodiment of a substantially C-shaped wire comprising a shape memory material configured to contract in a first direction and expand in a second direction. Suitable shape memory materials include shape memory polymers or shape memory alloys including, for example, ferromagnetic shape memory alloys, as discussed above. FIG. 19 schematically illustrates the wire 800 in its activated configuration or memorized shape. For illustrative purposes, the wire 800 is shown relative to dashed lines representing its deformed shape or configuration when implanted into a body before activation.

When the shape memory material is activated, the wire 800 is configured to respond by contracting in a first direction as indicated by arrow 1824. In some embodiments, the wire 800 also expands in a second direction as indicated by arrows 1834. Thus, the wire 800 is usable by the annuloplasty ring 1826 shown in FIG. 18 to improve the coaptation of the leaflets 1812, 1814 by contracting the annulus 1816 in the anterior/posterior direction. In certain embodiments, the anterior/posterior contraction is in a range between approximately 10% and approximately 20%. In some embodiments, only a first portion 1910 and a second portion 1912 of the wire 800 comprise the shape memory material. When the shape memory material is activated, the first portion 1910 and the second portion 1912 of the wire 800 are configured to respond by transforming to their memorized configurations and reshaping the wire 800 as shown.

Figure 20A:
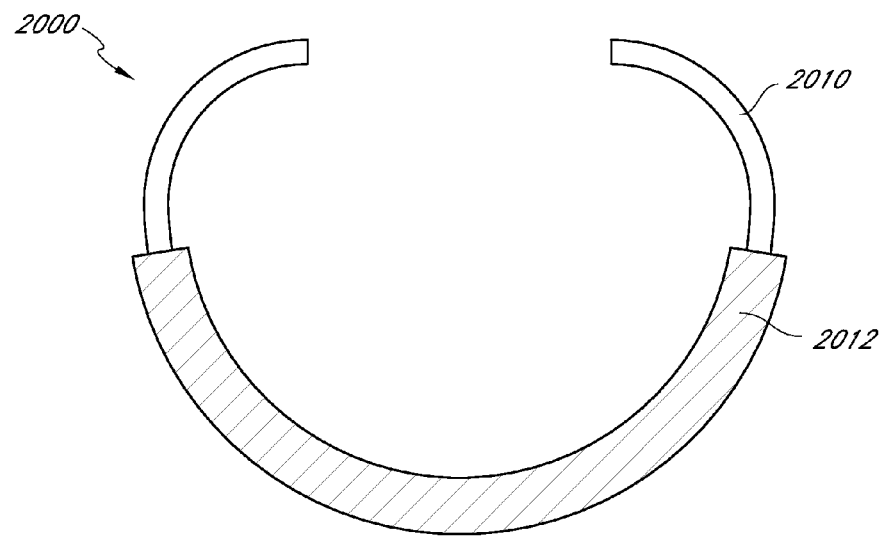
FIGS. 20A and 20B are schematic diagrams of an embodiment of a body member usable by an annuloplasty ring.
Figure 20B:
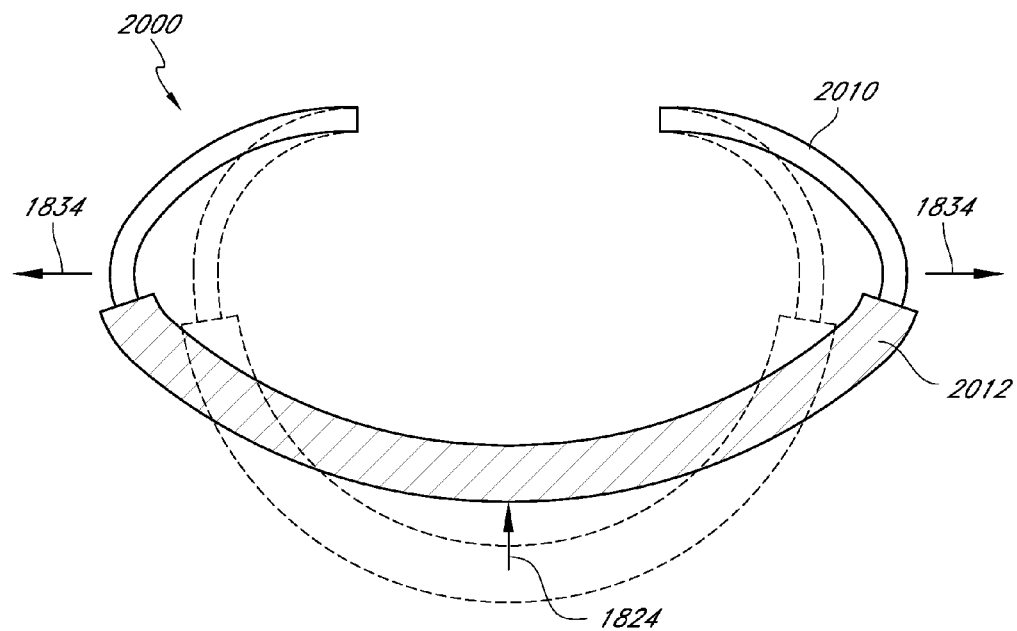

FIGS. 20A and 20B are schematic diagrams of an embodiment of a body member 2000 usable in an annuloplasty ring, such as the annuloplasty ring 1826 shown in FIG. 18. Although not shown, in some embodiments, the body member 2000 is covered by a flexible material such as silicone rubber and a suturable material such as woven polyester cloth, Dacron®, woven velour, polyurethane, polytetrafluoroethylene (PTFE), heparin-coated fabric, or other biocompatible material, as discussed above.

The body member 2000 comprises a wire 2010 and a shape memory tube 2012. As used herein, the terms "tube," "tubular member" and "tubular structure" are broad terms having at least their ordinary and customary meaning and include, for example, hollow elongated structures that may in cross-section be cylindrical, elliptical, polygonal, or any other shape. Further, the hollow portion of the elongated structure may be filled with one or more materials that may be the same as and/or different than the material of the elongated structure.

In some embodiments, the wire 2010 comprises a metal or metal alloy such as stainless steel, titanium, platinum, combinations of the foregoing, or the like. In some embodiments, the shape memory tube 2012 comprises shape memory materials formed in a tubular structure through which the wire 2010 is inserted. In some embodiments, the shape memory tube 2012 comprises a shape memory material coated over the wire 2010. Suitable shape memory materials include shape memory polymers or shape memory alloys including, for example, ferromagnetic shape memory alloys, as discussed above. Although not shown, in some embodiments, the body member 2000 comprises an energy absorption enhancement material, as discussed above.

FIG. 20A schematically illustrates the body member 2000 in a first configuration or shape and FIG. 20B schematically illustrates the body member 2000 in a second configuration or shape after the shape memory tube has been activated. For illustrative purposes, dashed lines in FIG. 20B also show the first configuration of the body member 2000. When the shape memory material is activated, the shape memory tube 2012 is configured to respond by contracting in a first direction as indicated by arrow 1824. In some embodiments, the shape memory tube 2012 is also configured to expand in a second direction as indicated by arrows 1834. The transformation of the shape memory tube 2012 exerts a force on the wire 2010 so as to change its shape. Thus, the body member 2000 is usable by the annuloplasty ring 1826 shown in FIG. 18 to pull the commissures 1818, 1820 further apart and push the leaflets 1812, 1814 closer together to improve coaptation.

Figure 21A:
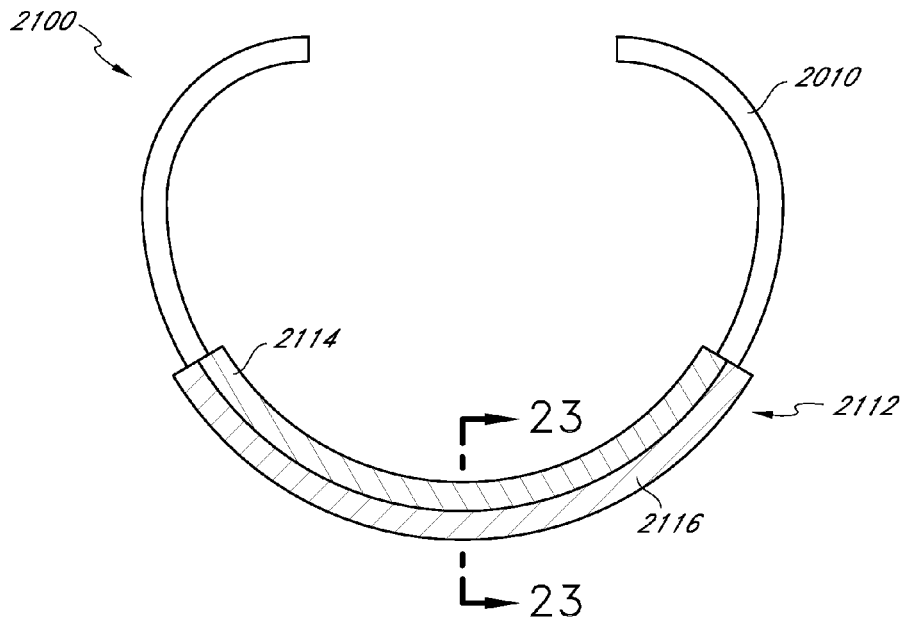
FIGS. 21A and 21B are schematic diagrams of an embodiment of a body member usable by an annuloplasty ring.
Figure 21B:
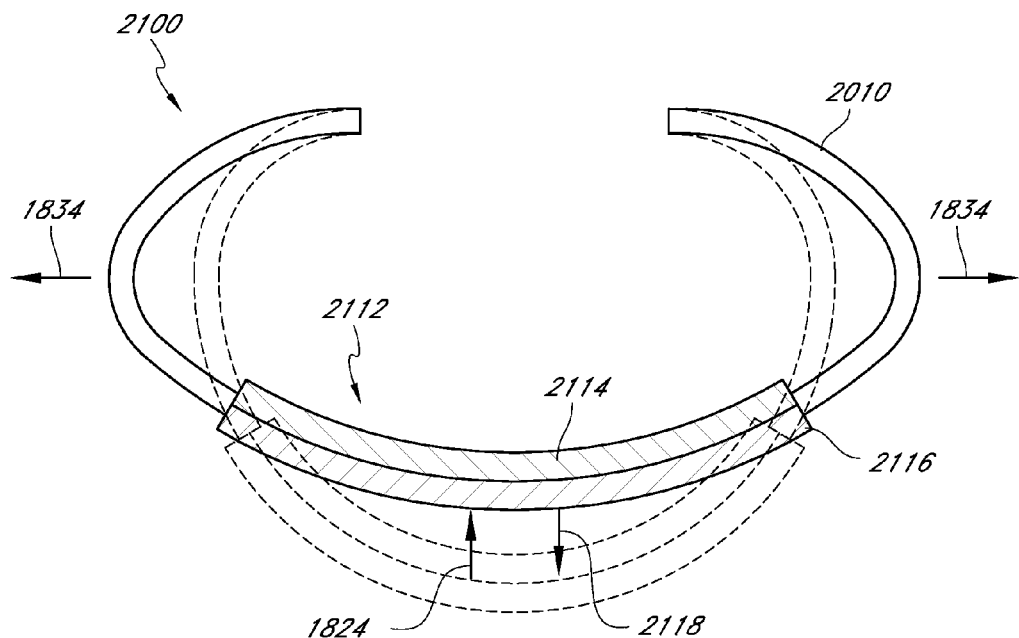

FIGS. 21A and 21B are schematic diagrams of an embodiment of a body member 2100 usable in an annuloplasty ring, such as the annuloplasty ring 1826 shown in FIG. 18. Although not shown, in some embodiments, the body member 2100 is covered by a flexible material such as silicone rubber and a suturable material such as woven polyester cloth, Dacron®, woven velour, polyurethane, polytetrafluoroethylene (PTFE), heparin-coated fabric, or other biocompatible material, as discussed above.

Figure 22A:
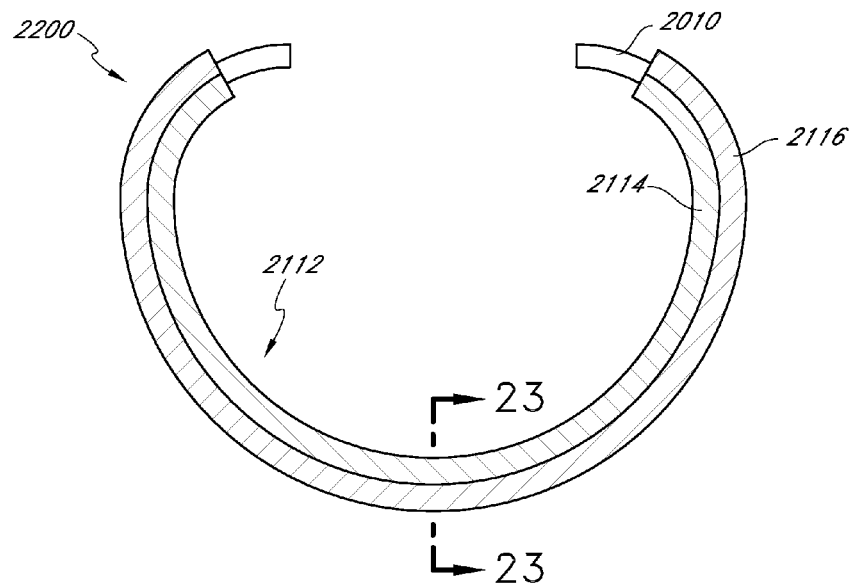
FIGS. 22A and 22B are schematic diagrams of an embodiment of a body member usable by an annuloplasty ring.
Figure 22B:
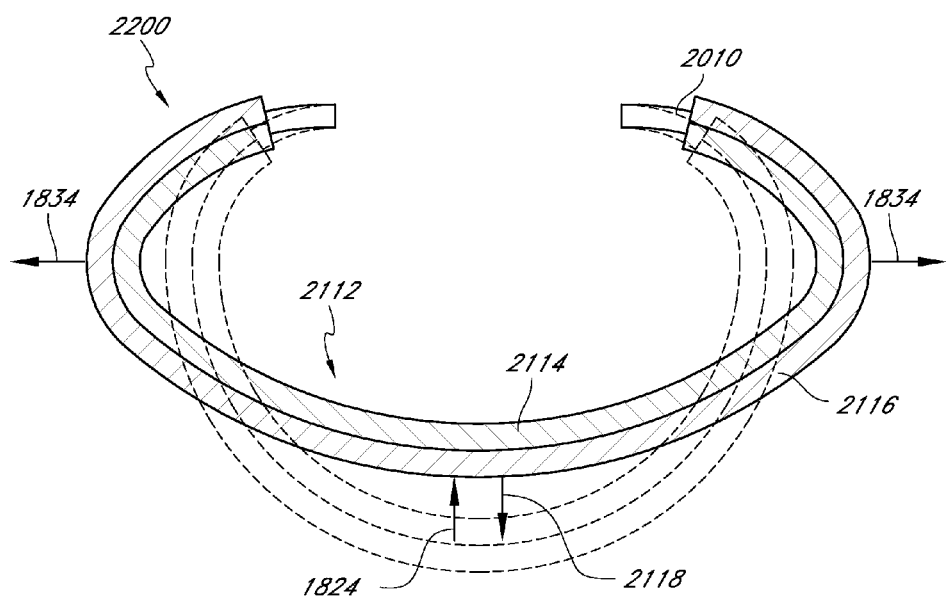

The body member 2100 comprises a wire 2010, such as the wire 2010 shown in FIGS. 20A and 20B and a shape memory tube 2112. As schematically illustrated in FIGS. 21A and 21B, the shape memory tube 2112 is sized and configured to cover a certain percentage of the wire 2010. However, an artisan will recognize from the disclosure herein that in some embodiments the shape memory tube 2112 can cover other percentages of the wire 2010. Indeed, FIGS. 22A and 22B schematically illustrate an embodiment of a body member 2200 comprising a shape memory tube 2112 covering a substantial portion of a wire 2010. The amount of coverage depends on such factors as the particular application, the desired shape change, the shape memory materials used, the amount of force to be exerted by the shape memory tube 2112 when changing shape, combinations of the foregoing, and the like. For example, in some embodiments where, as in FIGS. 22A and 22B, the shape memory tube 2112 covers a substantial portion of a wire 2010, portions of the shape memory tube 2112 are selectively heated to reshape the wire 2010 at a particular location. In some embodiments, HIFU energy is directed towards, for example, the left side of the shape memory tube 2112, the right side of the shape memory tube 2112, the bottom side of the shape memory tube 2112, or a combination of the foregoing to activate only a portion of the shape memory tube 2112. Thus, the body member 2200 can be reshaped one or more portions at a time to allow selective adjustments.

Figure 23:
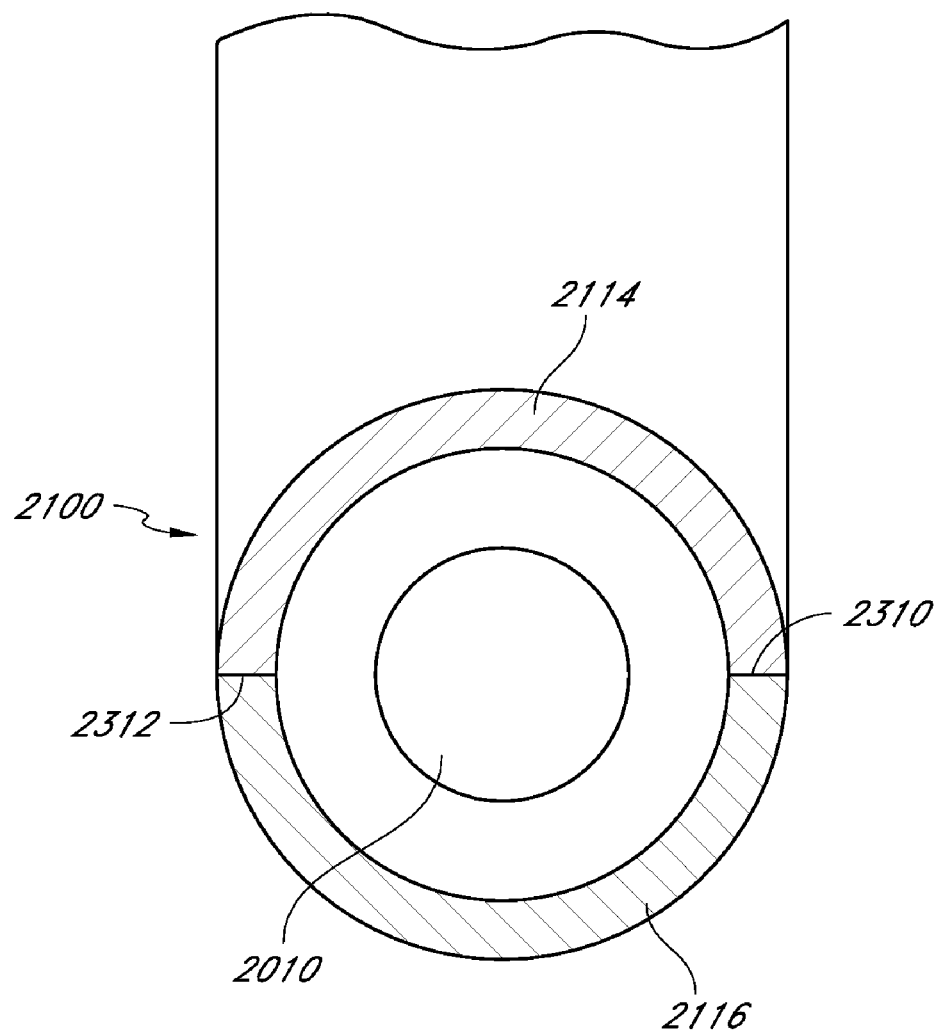
FIG. 23 is a transverse cross-sectional view of the body member of FIGS. 21A and 21B.

In some embodiments, the shape memory tube 2112 comprises a first shape memory material 2114 and a second shape memory material 2116 formed in a tubular structure through which the wire 2010 is inserted. In some embodiments, the first shape memory material 2114 and the second shape memory material 2116 are each configured as a semi-circular portion of the tubular structure. For example, FIG. 23 is a transverse cross-sectional view of the body member 2100. As schematically illustrated in FIG. 23, the first shape memory material 2114 and the second shape memory material 2116 are joined at a first boundary 2310 and a second boundary 2312. In some embodiments, silicone tubing (not shown) holds the first shape memory material 2114 and the second shape memory material 2116 together. In some embodiments, the first shape memory material 2114 and the second shape memory material 2116 each comprise a shape memory coating covering opposite sides of the wire 2010. Suitable shape memory materials include shape memory polymers or shape memory alloys including, for example, ferromagnetic shape memory alloys, as discussed above. Although not shown, in some embodiments the body member 2100 comprises an energy absorption enhancement material, as discussed above.

FIG. 21A schematically illustrates the body member 2100 in a first configuration or shape before the first shape memory material 2114 and the second shape memory material 2116 are activated. In some embodiments, the first shape memory material 2114 and the second shape memory material 2116 are configured to be activated or return to their respective memorized shapes at different temperatures. Thus, the first shape memory material 2114 and the second shape memory material 2116 can be activated at different times to selectively expand and/or contract the body member 2100. For example, in some embodiments, the second shape memory material 2116 is configured to be activated at a lower temperature than the first shape memory material 2114.

FIG. 21B schematically illustrates the body member 2100 in a second configuration or shape after the second shape memory material 2116 has been activated. For illustrative purposes, dashed lines in FIG. 21B also show the first configuration of the body member 2100. When the second shape memory material 2116 is activated, it responds by bending the body member 2100 in a first direction as indicated by arrow 1824. In some embodiments, activation also expands the body member 2100 in a second direction as indicated by arrows 1834. Thus, the body member 2100 is usable by the annuloplasty ring 1826 shown in FIG. 18 to pull the commissures 1818, 1820 further apart and push the leaflets 1812, 1814 closer together to improve coaptation.

In some embodiments, the first shape memory material 2114 can then be activated to bend the body member 2100 opposite to the first direction as indicated by arrow 2118. In some embodiments, the body member 2100 is reshaped to the first configuration as shown in FIG. 21A (or the dashed lines in FIG. 21B). Thus, for example, if the size of the patient's heart begins to grow again (e.g., due to age or illness), the body member 2100 can be enlarged to accommodate the growth. In certain other embodiments, activation of the first shape memory material 2114 further contracts the body member 2100 in the direction of the arrow 1824. In certain embodiments, the first shape memory material 2114 has an austenite start temperature $A_s$ in a range between about 42° C. and about 50° C. and the second shape memory material 2116 has an austenite start temperature $A_s$ in a range between approximately 38° C. and 41° C.

Figure 24:
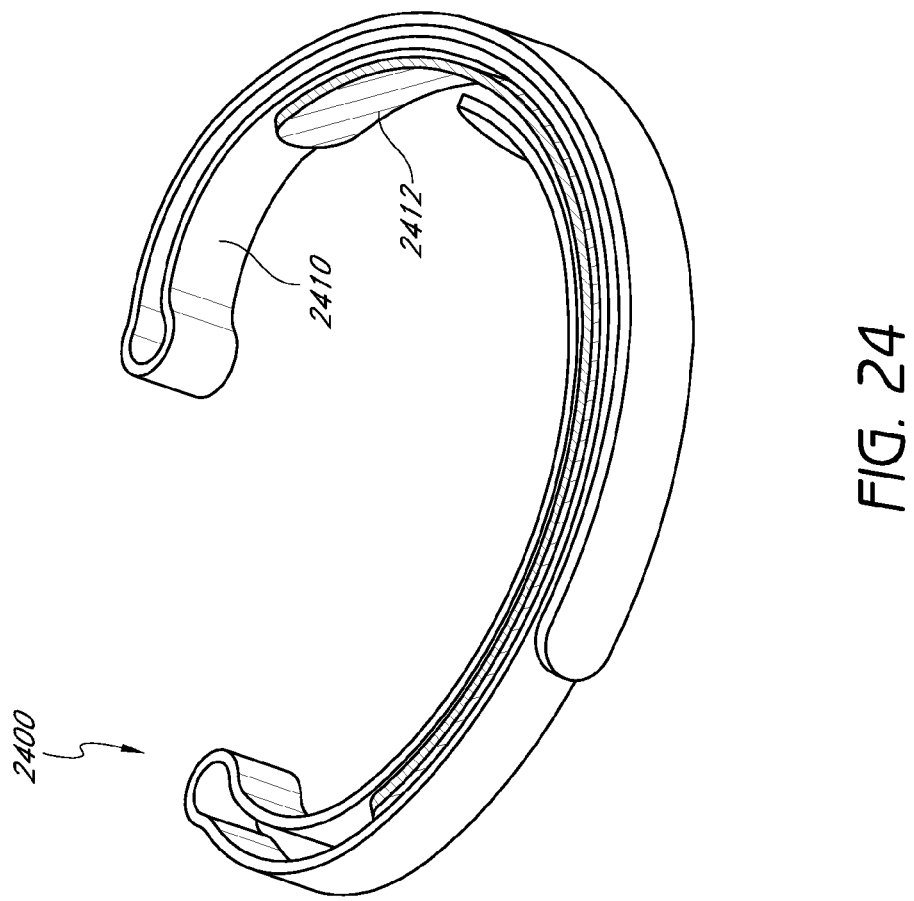
FIG. 24 is a perspective view of an embodiment of a body member usable by an annuloplasty ring comprising a first shape memory band and a second shape memory band.

FIG. 24 is a perspective view of a body member 2400 usable by an annuloplasty ring according to certain embodiments comprising a first shape memory band 2410 and a second shape memory band 2412. Suitable shape memory materials for the bands 2410, 2412 include shape memory polymers or shape memory alloys including, for example, ferromagnetic shape memory alloys, as discussed above. Although not shown, in some embodiments the body member 2100 comprises an energy absorption enhancement material, as discussed above. Although not shown, in some embodiments, the body member 2100 is covered by a flexible material such as silicone rubber and a suturable material such as woven polyester cloth, Dacron®, woven velour, polyurethane, polytetrafluoroethylene (PTFE), heparin-coated fabric, or other biocompatible material, as discussed above.

The first shape memory band 2410 can be configured to loop back on itself to form a substantially C-shaped configuration. However, an artisan will recognize from the disclosure herein that the first shape memory band 2410 can be configured to loop back on itself in other configurations including, for example, circular, D-shaped, or other curvilinear configurations. When activated, the first shape memory band 2410 expands or contracts such that overlapping portions of the band 2410 slide with respect to one another, changing the overall shape of the body member 2400. The second shape memory band 2412 is disposed along a surface of the first shape memory band 2410 such that the second shape memory band 2412 is physically deformed when the first shape memory band 2410 is activated, and the first shape memory band 2410 is physically deformed when the second shape memory band 2412 is activated.

As shown in FIG. 24, in some embodiments at least a portion of the second shape memory band 2412 is disposed between overlapping portions of the first shape memory band 2410. An artisan will recognize from the disclosure herein, however, that the second shape memory band 2412 may be disposed adjacent to an outer surface or an inner surface of the first shape memory band 2410 rather than between overlapping portions of the first shape memory band 2410. When the second shape memory band 2412 is activated, it expands or contracts so as to slide with respect to the first shape memory band 2410. In some embodiments, the first shape memory band 2410 and the second shape memory band 2412 are held in relative position to one another by the flexible material and/or suturable material discussed above.

While the first shape memory band 2410 and the second shape memory band 2412 shown in FIG. 24 are substantially flat, an artisan will recognize from the disclosure herein that other shapes are possible including, for example, rod-shaped wire. However, in some embodiments the first shape memory band 2410 and the second shape memory band 2412 advantageously comprise substantially flat surfaces configured to guide one another during expansion and/or contraction. Thus, the surface area of overlapping portions of the first shape memory band 2410 and/or the second shape memory band 2412 guide the movement of the body member 2400 in a single plane and reduce misalignment (e.g., twisting or moving in a vertical plane) during shape changes. The surface area of overlapping portions also advantageously increases support to a heart valve by reducing misalignment during beating of the heart.

An artisan will recognize from the disclosure herein that some embodiments of the body member 2400 may not comprise either the first shape memory band 2410 or the second shape memory band 2412. For example, in some embodiments the body member 2400 does not include the second shape memory band 2412 and is configured to expand and/or contract by only activating the first shape memory band 2410. Further, an artisan will recognize from the disclosure herein that either the first band 2410 or the second band 2412 may not comprise a shape memory material. For example, the first band 2410 may titanium, platinum, stainless steel, combinations of the foregoing, or the like and may be used with or without the second band 2412 to support a coronary valve annulus.

Figure 25A:
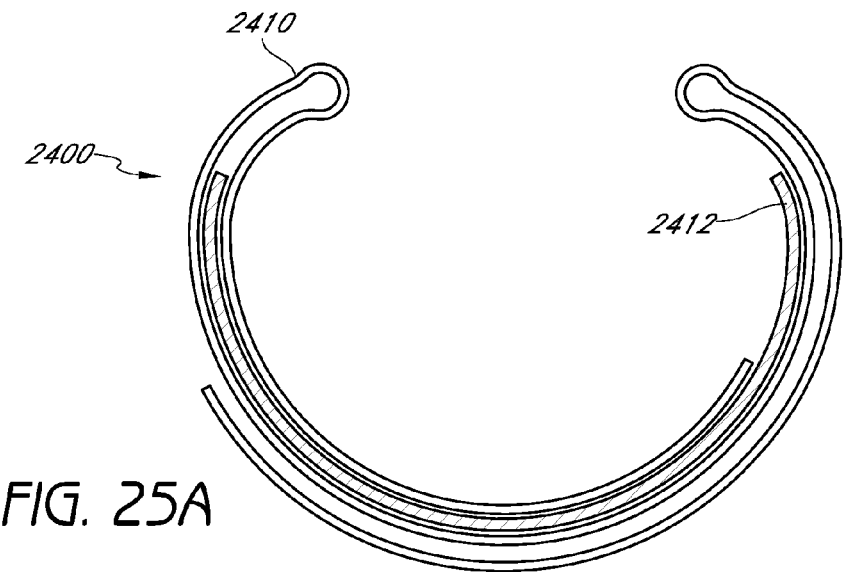
FIG. 25A is a schematic diagram illustrating the body member of FIG. 24 in a first configuration or shape.
Figure 25B:
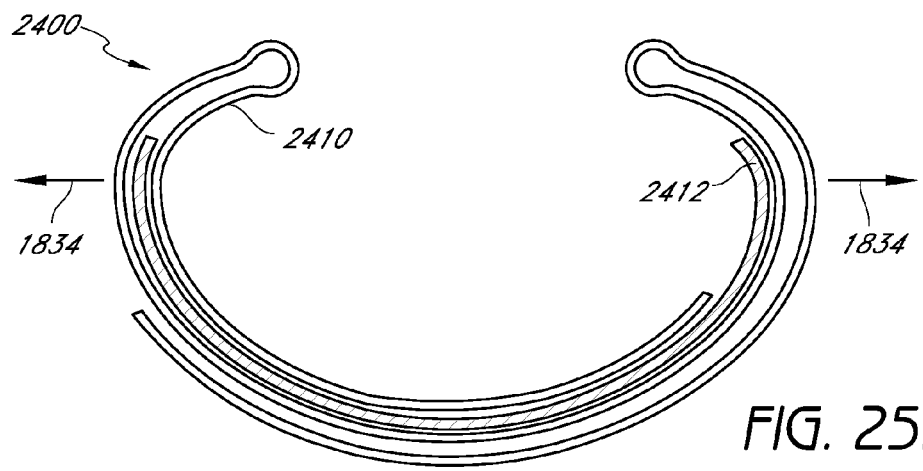
FIG. 25B is a schematic diagram illustrating the body member of FIG. 24 in a second configuration or shape.
Figure 25C:
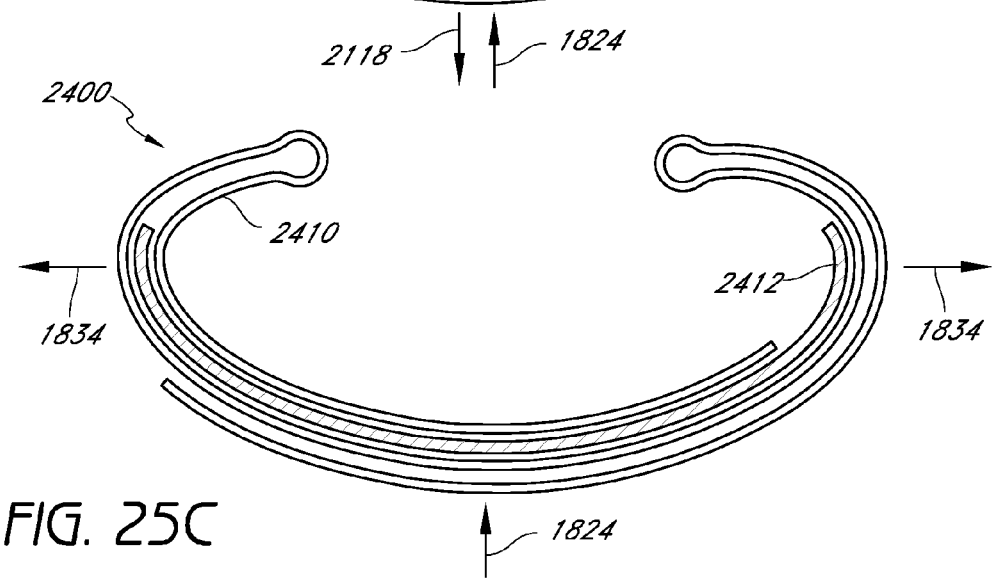
FIG. 25C is a schematic diagram illustrating the body member of FIG. 24 in a third configuration or shape.

As schematically illustrated in FIGS. 25A-25C, in some embodiments the body member 2400 is configured to change shape at least twice by activating both the first shape memory band 2410 and the second shape memory band 2412. FIG. 25A schematically illustrates the body member 2400 in a first configuration or shape before the first shape memory band 2410 or the second shape memory band 2412 are activated. In some embodiments, the first shape memory band 2410 and the second shape memory band 2412 are configured to be activated or return to their respective memorized shapes at different temperatures. Thus, the first shape memory band 2410 and the second shape memory band 2412 can be activated at different times to selectively expand and/or contract the body member 2400. For example (and for purposes of discussing FIGS. 25A-25C), in some embodiments, the first shape memory band 2410 is configured to be activated at a lower temperature than the second shape memory band 2412. However, an artisan will recognize from the disclosure herein that in other embodiments the second shape memory band 2412 may be configured to be activated at a lower temperature than the first shape memory band 2410.

FIG. 25B schematically illustrates the body member 2400 in a second configuration or shape after the first shape memory band 2410 has been activated. When the first shape memory band 2410 is activated, it responds by bending the body member 2400 in a first direction as indicated by arrow 1824. In some embodiments, the activation also expands the body member 2400 in a second direction as indicated by arrows 1834. Thus, the body member 2400 is usable by the annuloplasty ring 1826 shown in FIG. 18 to pull the commissures 1818, 1820 further apart and push the leaflets 1812, 1814 closer together to improve coaptation.

In some embodiments, the second shape memory band 2412 can then be activated to further contract the body member 2400 in the direction of the arrow 1824 and, in certain embodiments, further expand the body member 2400 in the direction of arrows 1834. In some embodiments, activating the second shape memory band 2412 reshapes the body member 2400 to a third configuration as shown in FIG. 25C. Thus, for example, as the patient's heart progressively heals and reduces in size, the body member 2400 can be re-sized to provide continued support and improved leaflet coaptation. In some embodiments, activation of the second shape memory band 2412 bends the body member 2400 opposite to the first direction as indicated by arrow 2118. In some embodiments, activating the second shape memory band 2412 reshapes the body member 2400 to the first configuration as shown in FIG. 25A. Thus, for example, if the size of the patient's heart begins to grow again (e.g., due to age or illness), the body member 2400 can be re-sized to accommodate the growth.

In certain annuloplasty ring embodiments, flexible materials and/or suturable materials used to cover shape memory materials also thermally insulate the shape memory materials so as to increase the time required to activate the shape memory materials through application of thermal energy. Thus, surrounding tissue is exposed to the thermal energy for longer periods of time, which may result in damage to the surrounding tissue. Therefore, in some embodiments, thermally conductive materials are configured to penetrate the flexible materials and/or suturable materials so as to deliver thermal energy to the shape memory materials such that the time required to activate the shape memory materials is decreased.

Figure 26:
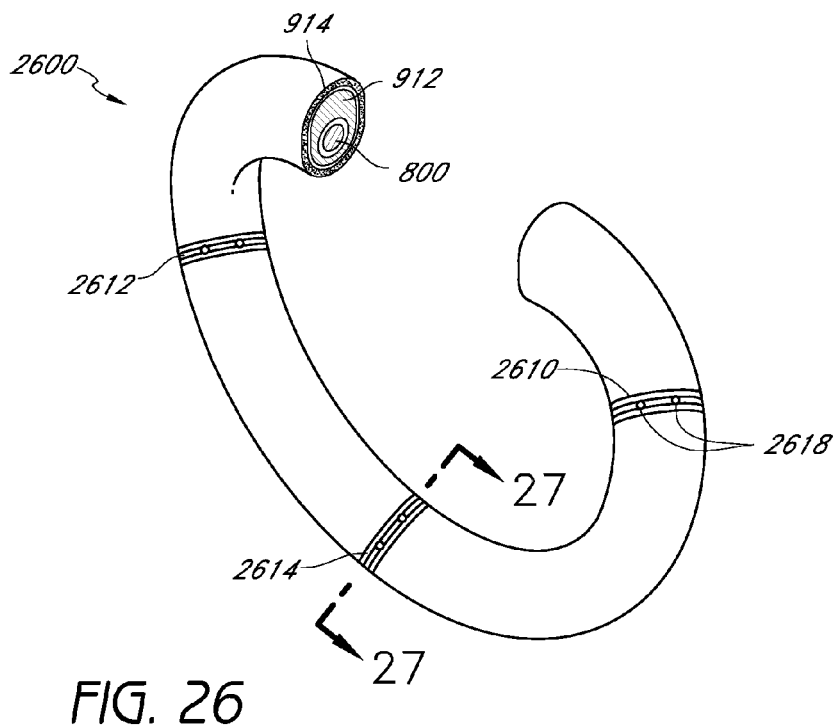
FIG. 26 is a perspective view illustrating an embodiment of an annuloplasty ring comprising one or more thermal conductors.

For example, FIG. 26 is a perspective view illustrating an embodiment of an annuloplasty ring 2600 comprising one or more thermal conductors 2610, 2612, 2614. The annuloplasty ring 2600 further comprises a shape memory wire 800 covered by a flexible material 912 and a suturable material 914, such as the wire 800, the flexible material 912 and the suturable material 914 shown in FIG. 9A. As shown in FIG. 26, in some embodiments, the shape memory wire 800 is offset from the center of the flexible material 912 to allow more room for sutures to pass through the flexible material 912 and suturable material 914 to attach the annuloplasty ring 2600 to a cardiac valve. In some embodiments, the flexible material 912 and/or the suturable material 914 are thermally insulative. In some embodiments, the flexible material 912 comprises a thermally insulative material. Although the annuloplasty ring 2600 is shown in FIG. 26 as substantially C-shaped, an artisan will recognize from the disclosure herein that the one or more thermal conductors 2610, 2612, 2614 can also be used with other configurations including, for example, circular, D-shaped, or other curvilinear configurations.

Figure 27A:
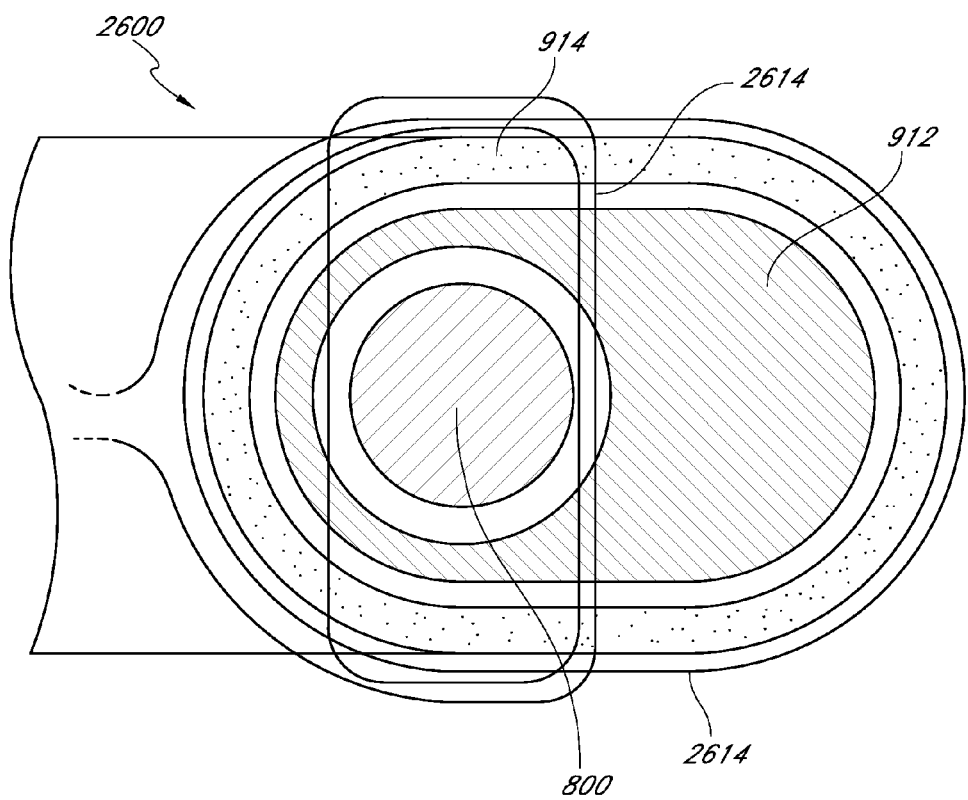
FIGS. 27A-27C are transverse cross-sectional views of the annuloplasty ring of FIG. 26 schematically illustrating exemplary embodiments of the invention for conducting thermal energy to an internal shape memory wire.
Figure 27B:
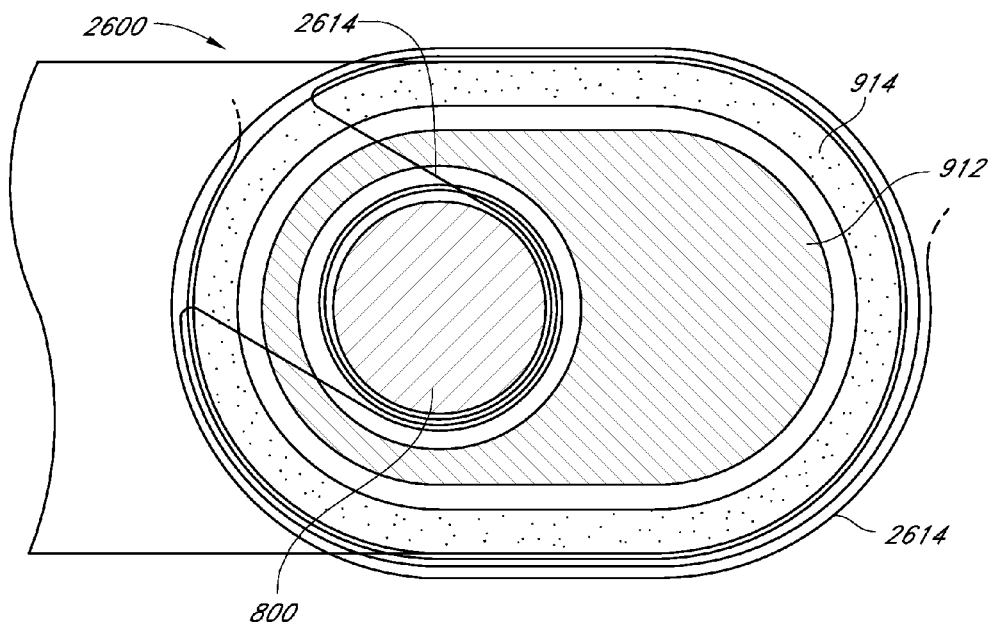
Figure 27C:
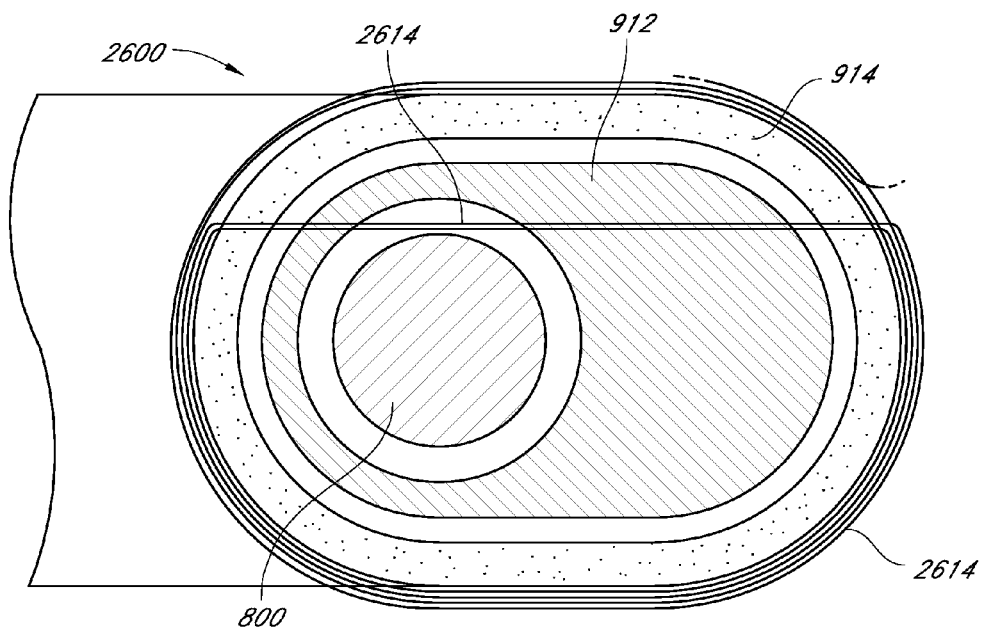

In some embodiments, the thermal conductors 2610, 2612, 2614 comprise a thin (e.g., having a thickness in a range between approximately 0.002 inches and approximately 0.015 inches) wire wrapped around the outside of the suturable material 914 and penetrating the suturable material 914 and the flexible material 912 at one or more locations 2618 so as to transfer externally applied heat energy to the shape memory wire 800. For example, FIGS. 27A-27C are transverse cross-sectional views of the annuloplasty ring 2600 schematically illustrating exemplary embodiments for conducting thermal energy to the shape memory wire 800. In the exemplary embodiment shown in FIG. 27A, the thermal conductor 2614 wraps around the suturable material 914 one or more times, penetrates the suturable material 914 and the flexible material 912, passes around the shape memory wire 800, and exits the flexible material 912 and the suturable material 914. In some embodiments, the thermal conductor 2614 physically contacts the shape memory wire 800. However, in some embodiments, the thermal conductor 2614 does not physically contact the shape memory wire 800 but passes sufficiently close to the shape memory wire 800 so as to decrease the time required to activate the shape memory wire 800. Thus, the potential for thermal damage to surrounding tissue is reduced.

In an exemplary embodiment shown in FIG. 27B, the thermal conductor 2614 wraps around the suturable material 914 one or more times, penetrates the suturable material 914 and the flexible material 912, passes around the shape memory wire 800 two or more times, and exits the flexible material 912 and the suturable material 914. By passing around the shape memory wire 800 two or more times, the thermal conductor 2614 concentrates more energy in the area of the shape memory wire 800 as compared to the exemplary embodiment shown in FIG. 27A. Again, the thermal conductor 2614 may or may not physically contact the shape memory wire 800.

In an exemplary embodiment shown in FIG. 27C, the thermal conductor 2614 wraps around the suturable material 914 one or more times and passes through the suturable material 914 and the flexible material 912 two or more times. Thus, portions of the thermal conductor 2614 are disposed proximate the shape memory wire 800 so as to transfer heat energy thereto. Again, the thermal conductor 2614 may or may not physically contact the shape memory wire 800. An artisan will recognize from the disclosure herein that one or more of the exemplary embodiments shown in FIGS. 27A-27C can be combined and that the thermal conductor 2614 can be configured to penetrate the suturable material 914 and the flexible material 912 in other ways, so as to transfer heat to the shape memory wire 800.

Referring again to FIG. 26, in some embodiments the locations of the thermal conductors 2610, 2612, 2614 are selected based at least in part on areas where energy will be applied to activate the shape memory wire 800. For example, in some embodiments heat energy is applied percutaneously through a balloon catheter and the thermal conductors 2610, 2612, 2614 are disposed on the surface of the suturable material 914 in locations likely to make contact with the inflated balloon.

In some embodiments, the thermal conductors 2610, 2612, 2614 are located so as to mark desired positions on the annuloplasty ring 2600. For example, the thermal conductors 2610, 2612, 2614 may be disposed at locations on the annuloplasty ring 2600 corresponding to commissures of heart valve leaflets, as discussed above with respect to FIG. 18. As another example, the thermal conductors 2610, 2612, 2614 can be used to align a percutaneous energy source, such as a heated balloon inserted through a catheter, with the annuloplasty ring 2600. In some embodiments the thermal conductors 2610, 2612, 2614 comprise radiopaque materials such as gold, copper or other imaging materials, as is known in the art.

Figure 28:
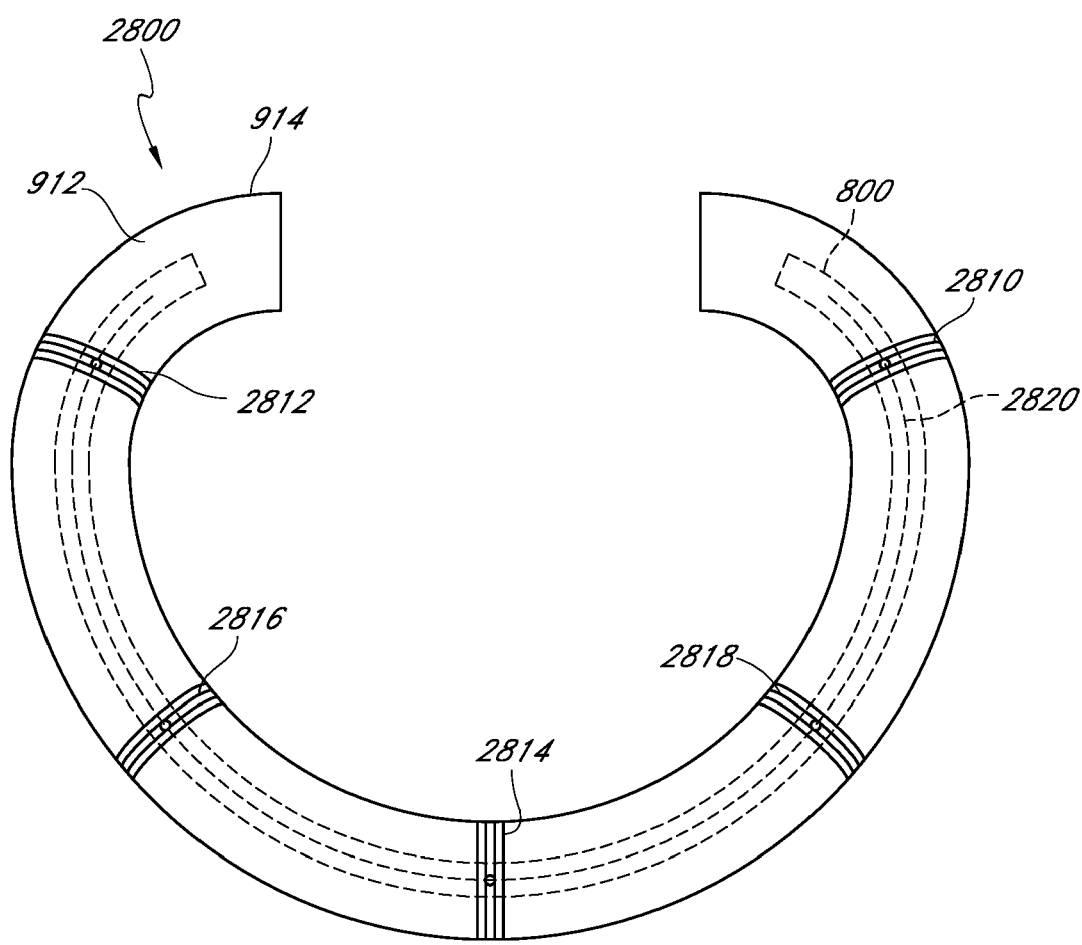
FIG. 28 is a schematic diagram of an embodiment of an annuloplasty ring comprising one or more thermal conductors.

FIG. 28 is a schematic diagram of an embodiment of an annuloplasty ring 2800, comprising one or more thermal conductors 2810, 2812, 2814, 2816, 2818, such as the thermal conductors 2610, 2612, 2614 shown in FIG. 26. As schematically illustrated in FIG. 28, the annuloplasty ring 2800 further comprises a shape memory wire 800 covered by a flexible material 912 and a suturable material 914, such as the wire 800, the flexible material 912 and the suturable material 914 shown in FIG. 9A.

In some embodiments, the shape memory wire 800 is not sufficiently thermally conductive so as to quickly transfer heat applied in the areas of the thermal conductors 2810, 2812, 2814, 2816, 2818. Thus, in some embodiments, the annuloplasty ring 2800 comprises a thermal conductor 2820 that runs along the length of the shape memory wire 800 so as to transfer heat to points of the shape memory wire 800 extending beyond or between the thermal conductors 2810, 2812, 2814, 2816, 2818. In some embodiments, each of the thermal conductors 2810, 2812, 2814, 2816, 2818, comprise a separate thermally conductive wire configured to transfer heat to the thermal conductive wire 2820. However, in some embodiments, at least two of the thermal conductors 2810, 2812, 2814, 2816, 2818 and the thermal conductor 2820 comprise one continuous thermally conductive wire.

Thus, thermal energy can be quickly transferred to the annuloplasty ring 2600 or the annuloplasty ring 2800 to reduce the amount of energy required to activate the shape memory wire 800 and to reduce thermal damage to the patient's surrounding tissue.

The skilled artisan will recognize the interchangeability of various features from different embodiments. Similarly, the various features and steps discussed above, as well as other known equivalents for each such feature or step, can be mixed and matched by one of ordinary skill in this art to perform compositions or methods in accordance with principles described herein. Although the disclosure has been provided in the context of certain embodiments and examples, it will be understood by those skilled in the art that the disclosure extends beyond the specifically described embodiments to other alternative embodiments and/or uses and obvious modifications and equivalents thereof. Accordingly, the disclosure is not intended to be limited by the specific disclosures of embodiments herein.

What is claimed is:

1. An adjustable annuloplasty device comprising:
a body member comprising a shape memory material;
wherein said body member has a first size of a body dimension in a first configuration and a second size of said body dimension in a second configuration;
wherein said body member is configured to be implanted in said first configuration into a heart;
wherein said body member is configured to transform from said first configuration to said second configuration in response to said first activation energy;
a first segment, having a first end and a second end, and a second segment, having a first end and a second end;
wherein said first segment and said second segment have original lengths when said annuloplasty device is in said first configuration;
wherein said second end of said first segment is proximate said first end of said second segment, and said first segment and said second segment are oriented end-to-end with respect to each other;
an energy transfer material configured to absorb energy in response to a first activation energy, said energy transfer material in thermal communication with said shape memory material;
wherein, when said annuloplasty device is in said second configuration, said first segment remains at substantially its original length, and said second segment has a length that is less than its original length;
wherein said second configuration is configured to reduce a dimension of a cardiac valve annulus in said heart;
wherein said first activation energy comprises high intensity focused ultrasound.

2. An adjustable annuloplasty device comprising:
a body member comprising a shape memory material;
wherein said body member has a first size of a body dimension in a first configuration and a second size of said body dimension in a second configuration;
wherein said body member is configured to be implanted in said first configuration into a heart;
wherein said body member is configured to transform from said first configuration to said second configuration in response to said first activation energy;
a first segment, having a first end and a second end, and a second segment, having a first end and a second end;
wherein said first segment and said second segment have original lengths when said annuloplasty device is in said first configuration;
wherein said second end of said first segment is proximate said first end of said second segment, and said first segment and said second segment are oriented end-to-end with respect to each other;
an energy transfer material configured to absorb energy in response to a first activation energy, said energy transfer material in thermal communication with said shape memory material;
wherein, when said annuloplasty device is in said second configuration, said first segment remains at substantially its original length, and said second segment has a length that is less than its original length;
wherein said second configuration is configured to reduce a dimension of a cardiac valve annulus in said heart;
further comprising a ratchet mechanism located on a proximal portion of the body member configured to engage a distal portion of the body member.

3. The device of claim 2, wherein the ratchet is configured to prevent expansion of the device when the distal portion is engaged.

4. The device of claim 2, wherein the distal portion of the body member comprises a plurality of detents configured to permit incremental advancement of the distal portion.

5. An adjustable annuloplasty device comprising:
a body member comprising a shape memory material;
wherein said body member has a first size of a body dimension in a first configuration and a second size of said body dimension in a second configuration;
wherein said body member is configured to be implanted in said first configuration into a heart;
wherein said body member is configured to transform from said first configuration to said second configuration in response to said first activation energy;
a first segment, having a first end and a second end, and a second segment, having a first end and a second end;
wherein said first segment and said second segment have original lengths when said annuloplasty device is in said first configuration;
wherein said second end of said first segment is proximate said first end of said second segment, and said first segment and said second segment are oriented end-to-end with respect to each other;
an energy transfer material configured to absorb energy in response to a first activation energy, said energy transfer material in thermal communication with said shape memory material;
wherein, when said annuloplasty device is in said second configuration, said first segment remains at substantially its original length, and said second segment has a length that is less than its original length;
wherein said second configuration is configured to reduce a dimension of a cardiac valve annulus in said heart;
wherein the body dimension in the first configuration differs from the body dimension in the second configuration by an amount in range from about 6% to about 23%.

* * * * *